United States Patent
Miller et al.

(10) Patent No.: US 11,149,046 B2
(45) Date of Patent: Oct. 19, 2021

(54) ANTIBACTERIAL SIDEROMYCINS

(71) Applicant: Hsiri Therapeutics, Inc., Media, PA (US)

(72) Inventors: Marvin J. Miller, South Bend, IN (US); Yun-Ming Lin, South Bend, IN (US); Manuka Ghosh, Granger, IN (US); Patricia A. Miller, South Bend, IN (US); Ute Möllmann, Jena (DE)

(73) Assignee: HSIRI THERAPEUTICS, INC., Media, PA (US)

( * ) Notice: Subject to any disclaimer, the term of this patent is extended or adjusted under 35 U.S.C. 154(b) by 473 days.

(21) Appl. No.: 15/505,093

(22) PCT Filed: Sep. 10, 2015

(86) PCT No.: PCT/IB2015/056915
§ 371 (c)(1),
(2) Date: Feb. 19, 2017

(87) PCT Pub. No.: WO2016/027262
PCT Pub. Date: Feb. 25, 2016

(65) Prior Publication Data
US 2019/0153010 A1    May 23, 2019

Related U.S. Application Data

(60) Provisional application No. 62/039,405, filed on Aug. 19, 2014.

(51) Int. Cl.
| | |
|---|---|
| *C07K 7/00* | (2006.01) |
| *A61K 38/12* | (2006.01) |
| *A61P 31/00* | (2006.01) |
| *C07F 15/02* | (2006.01) |
| *A61K 47/54* | (2017.01) |

(Continued)

(52) U.S. Cl.
CPC .......... *C07F 15/025* (2013.01); *A61K 31/424* (2013.01); *A61K 31/43* (2013.01); *A61K 31/431* (2013.01); *A61K 45/06* (2013.01); *A61K 47/547* (2017.08); *A61K 47/6903* (2017.08); *A61P 31/04* (2018.01); *C07C 235/60* (2013.01); *C07D 209/18* (2013.01); *C07D 417/12* (2013.01); *C07D 463/22* (2013.01); *C07D 499/78* (2013.01); *C07D 501/59* (2013.01); *C07F 15/03* (2013.01); *A61K 31/39* (2013.01);
(Continued)

(58) Field of Classification Search
CPC ............. C07K 7/54; C07K 7/08; A61K 38/12
USPC ................... 514/2.2, 21.1; 530/317
See application file for complete search history.

(56) References Cited

U.S. PATENT DOCUMENTS

2013/0281424 A1* 10/2013 Miller .................. A61K 31/167
514/197

OTHER PUBLICATIONS

JI et al. "Exploring bacterial iron acquisition: siderophore conjugates," Future Med. Chem. 2012, vol. 4, No. 3, pp. 297-313 (Year: 2012).*

(Continued)

*Primary Examiner* — Shengjun Wang
(74) *Attorney, Agent, or Firm* — Law Office of John K. Pike, PLLC

(57) ABSTRACT

A compound, comprising: an Fe(III)-binding and/or Fe(III)-bound siderophore; one or more optional linker covalently bound to the siderophore; and daptomycin covalently bound to the linker, or, if no linker is present, then to the siderophore; or pharmaceutically acceptable salt or solvate thereof.

11 Claims, 42 Drawing Sheets

Daptomycin.

1, Daptomycin (Cubicin)
Chemical Formula: $C_{72}H_{101}N_{17}O_{26}$
Exact Mass: 1619.71
Molecular Weight: 1620.67

(51) Int. Cl.
*A61K 31/43* (2006.01)
*C07C 235/60* (2006.01)
*C07F 15/03* (2006.01)
*C07D 209/18* (2006.01)
*C07D 501/59* (2006.01)
*C07D 417/12* (2006.01)
*C07D 499/78* (2006.01)
*C07D 463/22* (2006.01)
*A61K 45/06* (2006.01)
*A61K 31/431* (2006.01)
*A61K 31/424* (2006.01)
*A61K 47/69* (2017.01)
*A61P 31/04* (2006.01)
*C07K 7/08* (2006.01)
*A61K 31/39* (2006.01)
*A61K 31/397* (2006.01)
*A61K 31/4192* (2006.01)

(52) U.S. Cl.
CPC ........ *A61K 31/397* (2013.01); *A61K 31/4192* (2013.01); *A61K 38/12* (2013.01); *C07K 7/08* (2013.01)

(56) References Cited

OTHER PUBLICATIONS

Sharma et al. "Spermexatin and spermexatol: new synthetic spermidine-based siderophore analogues," J. Medicinal Chemistry, 1989, vol. 32, No. 2, pp. 357-367. (Year: 1989).*
Ghosh et al. "Iron transport-mediated drug delivery using mixed-ligand siderophore-beta-lactam conjugates," Chemistry & Biology, 1996, vol. 3, No. 12, pp. 1011-1019. (Year: 1996).*

* cited by examiner

Figure 1. Daptomycin.
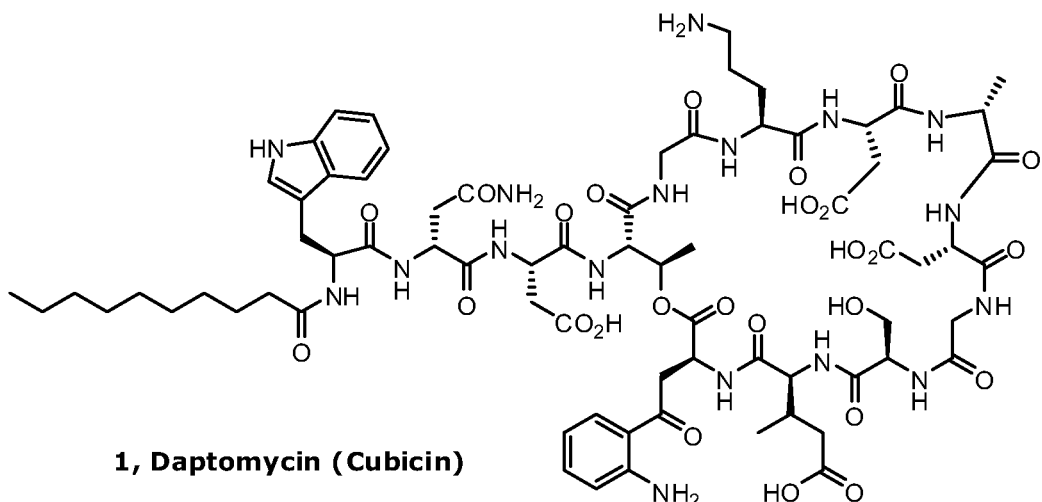
1, Daptomycin (Cubicin)
Chemical Formula: $C_{72}H_{101}N_{17}O_{26}$
Exact Mass: 1619.71
Molecular Weight: 1620.67

Figure 2. Natural and early examples of synthetic siderophore-antibiotic conjugates (sideromycins).
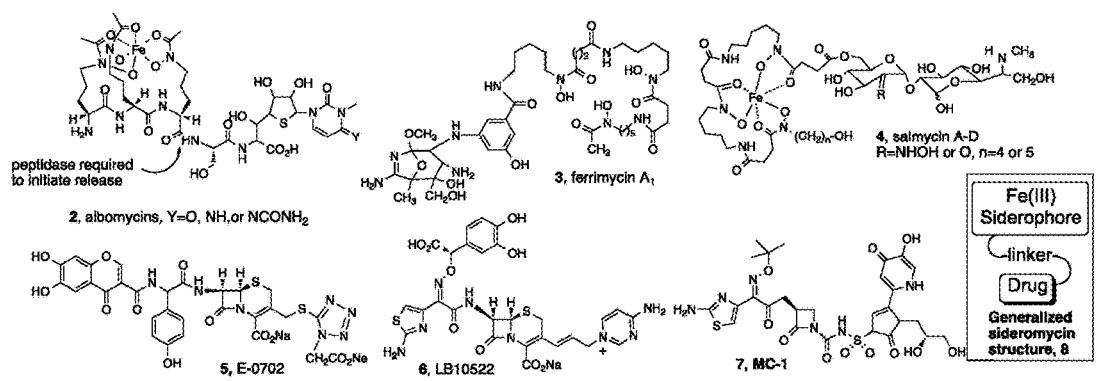

Figure 3A
| Compound | Cpd Type | Structure | Pa01 | Pa KW799/wt | Pa KW799/61 |
|---|---|---|---|---|---|
| loracarbef | | | >200μM | >200μM | 50μM |
| Ampicillin | | | >200μM | >200μM | .39μM |
| cefaclor | | | >50μM | >50μM | >50μM |
| MG-112 | | 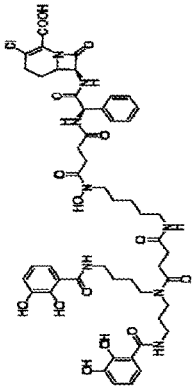 | >70μM | 70μM | .2μM |
| MG-115 | | 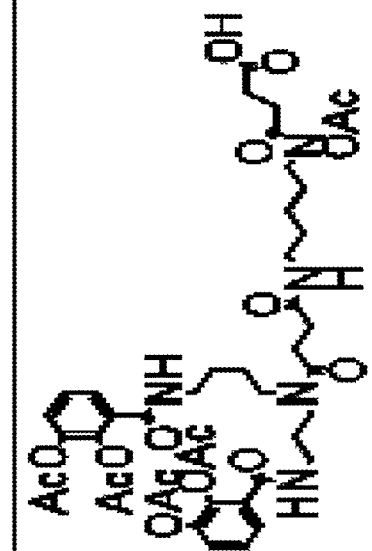 | >200μM | >200μM | >200μM |

Figure 3 B
| Compound | Cpd Type | Structure | Pa01 | Pa KW799/wt | Pa KW799/61 |
|---|---|---|---|---|---|
| MG-117a | | 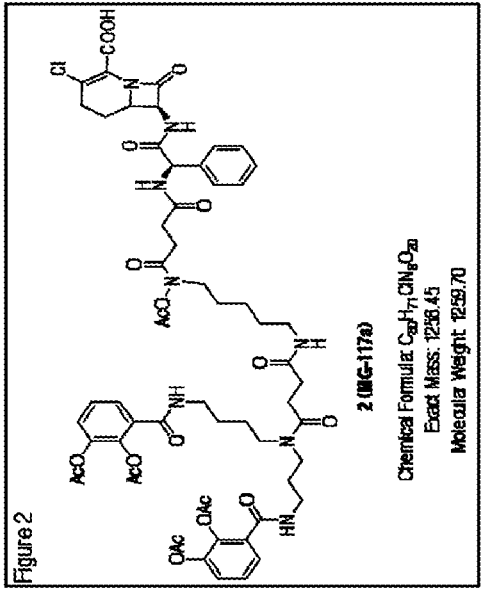 Figure 2<br>2 (MG-117a)<br>Chemical Formula: C₅₈H₇₁ClN₈O₂₀<br>Exact Mass: 1256.45<br>Molecular Weight: 1259.70 | >70μM | 70μM | .08μM |
| MG-121 (impure) | | 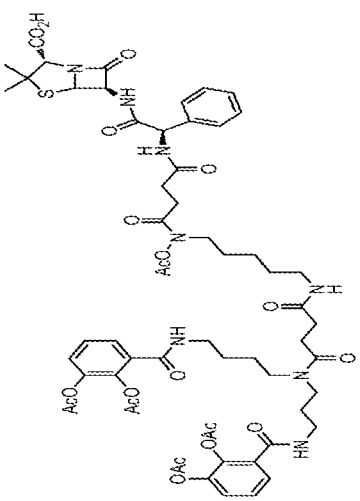 | <12.5μM & > 0.39μM-.55μM | 0.14μM-0.2μM | .025μM |

| Compound | Cpd Type | Structure | Pa01 | Pa KW799/wt | Pa KW799/61 |
|---|---|---|---|---|---|
| MG-127 | | 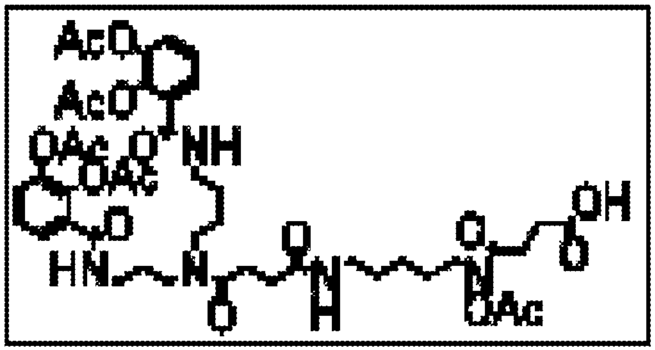 | | >200µM | >200µM |
| MG-185 | | 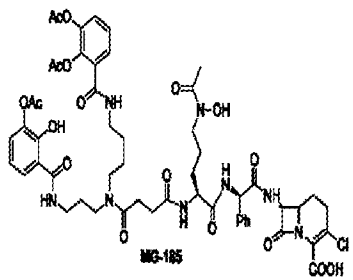 | >50µM | >50µM ??? 1.56M??? | 0.2µM |
| MG-186 | | 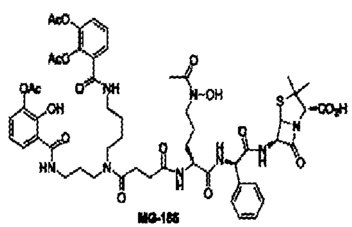 | <25µM and >0.2- 0.4µM | <50µM & >0.1µM | 0.05µM |

Figure 3 D

| Compound | Cpd Type | Structure | PaO1 | Pa KW799/wt | Pa KW799/61 |
|---|---|---|---|---|---|
| MG-188 | | MG-188 (MG-117a) | >50μM | >50μM | 0.39μM |
| MG-189 | | MG-189 (MG-112) | >50μM | >50μM | 0.1μM |

Figure 3 E

| Compound | Cpd Type | Structure | Pa01 | Pa KW799/wt | Pa KW799/61 |
|---|---|---|---|---|---|
| MG-216A | free acid | MG-216-A<br>Chemical Formula: $C_{58}H_{69}ClN_8O_{20}S$<br>Exact Mass: 1276.40<br>Molecular Weight: 1277.75 | >50µM | 0.39µM | |
| MG-216B | | 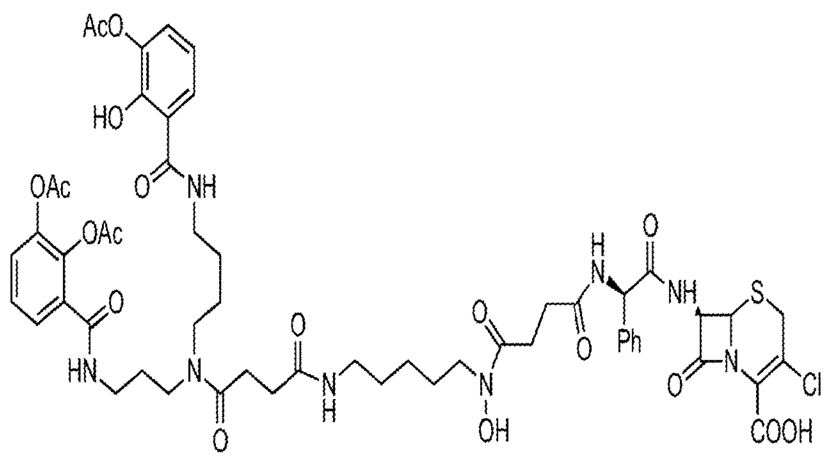 | >50µM | 0.39µM | |

Figure 3 F
| Compound | Cpd Type | Structure | Pa01 | Pa KW799/wt | Pa KW799/61 |
|---|---|---|---|---|---|
| MG-227 | free acid | 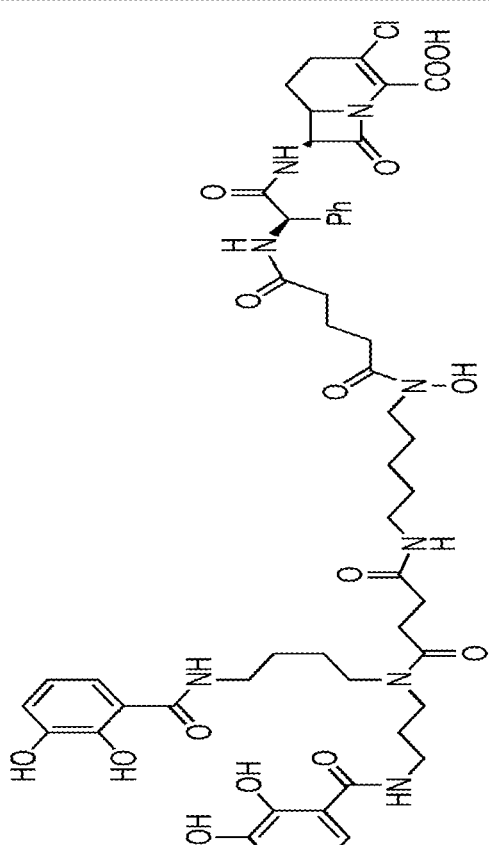 | >50µM | 0.2µM | |
| MG-228 | | 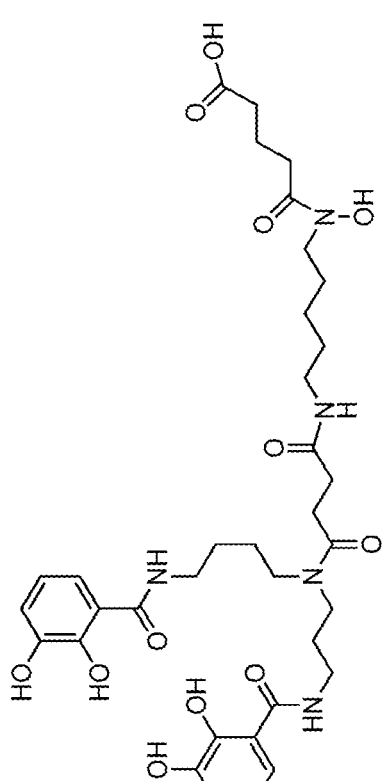 | | | |

Figure 3 G

| Compound | Cpd Type | Structure | PaO1 | Pa KW799/wt | Pa KW799/61 |
|---|---|---|---|---|---|
| MG-233B | Na salt | 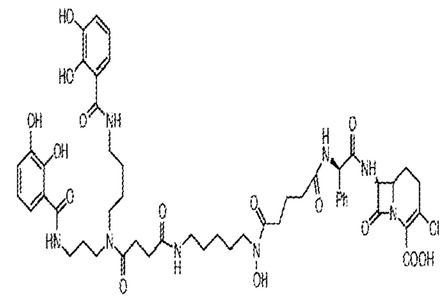 | >50μM | >50μM | |
| MG-237B | Na salt of MG-227 | 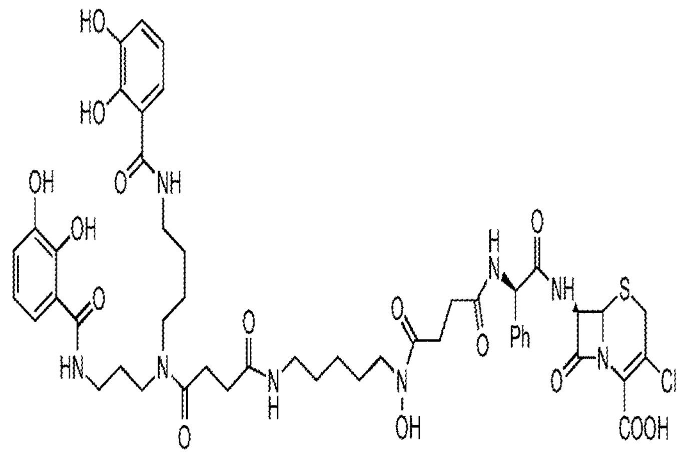 | >50μM | >50μM | |
| MG-121 (pure) | | | 0.2μM | .05μM | |

Figure 3 H
| Compound | Cpd Type | Structure | Pa01 | Pa KW799/wt | Pa KW799/61 |
|---|---|---|---|---|---|
| MG-1-251<br>MG-2-13<br>MG-2-18 | mixed ligand glutaryl ampicillin conjugate | 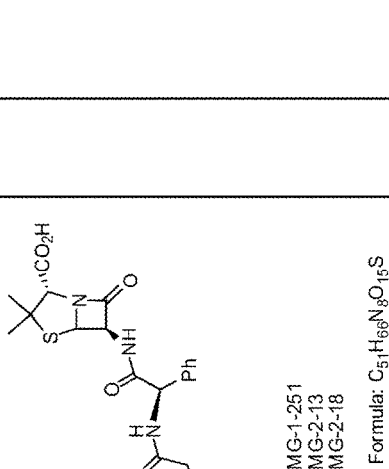 Chemical Formula: $C_{51}H_{66}N_8O_{15}S$<br>Exact Mass: 1062.44 | | | |
| MG-255 | | 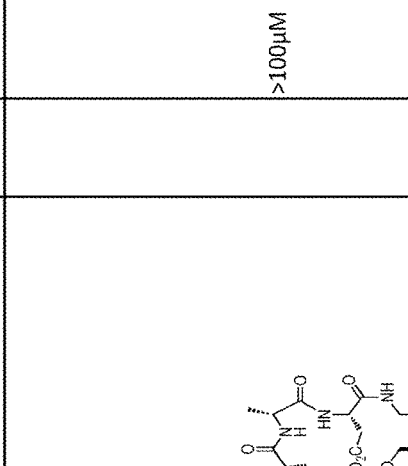 | | >100µM | |

Figure 3 I
| Compound | Cpd Type | Structure | Pa01 | Pa KW799/wt | Pa KW799/61 |
|---|---|---|---|---|---|
| MG-281 (MG-189-lotB) | | 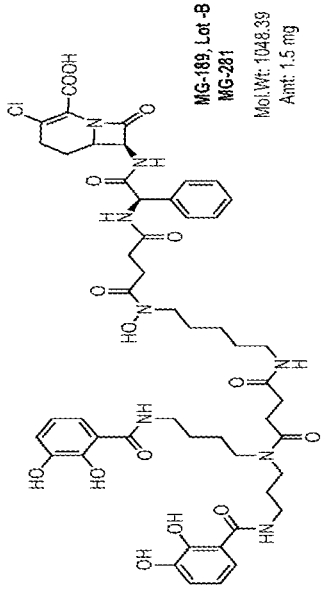 MG-189, Lot-B / MG-281 Mol.Wt: 1048.39 Amt: 1.5 mg | | | |
| MG-285 | | 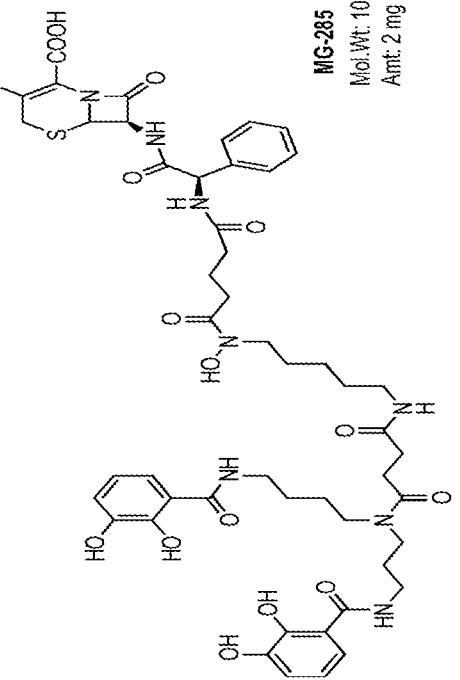 MG-285 Mol.Wt: 1081.59 Amt: 2 mg | | | |

Figure 3 J
| Compound | Cpd Type | Structure | Pa01 | Pa KW799/wt | Pa KW799/61 |
|---|---|---|---|---|---|
| MG-1-288 | | 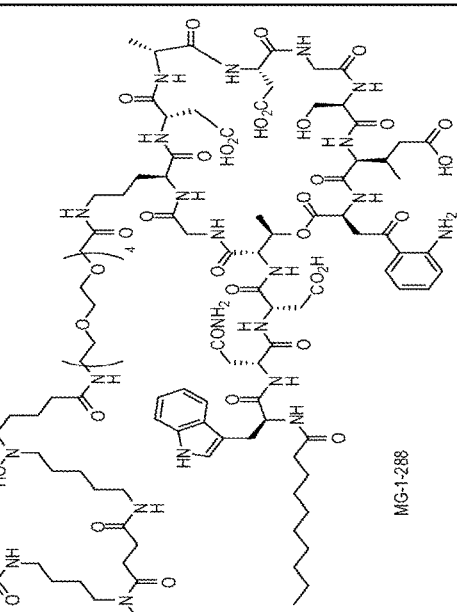 | | | |
| MG-1-294 | | 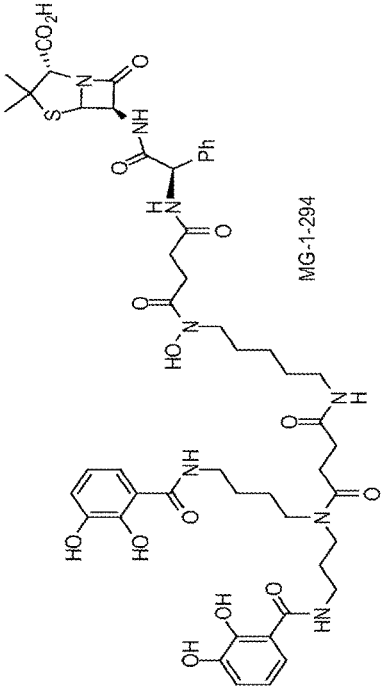 | | | |

Figure 3 K

| Compound | Cpd Type | Structure | Pa01 | Pa KW799/wt | Pa KW799/61 |
|---|---|---|---|---|---|
| MG-2-27 | mixed ligand glutaryl cefaclor conjugate | MG-2-27<br>Chemical Formula: $C_{50}H_{60}ClN_8NaO_{15}S$<br>Exact Mass: 1102.35 | | | |
| MG-1-299<br>MG-2-27a | mixed ligand glutaryl cefaclor conjugate | MG-1-299<br>MG-2-27a<br>Chemical Formula: $C_{50}H_{61}ClN_8O_{15}S$<br>Exact Mass: 1080.37 | | | |
| Sulbactam | | | | | |

Figure 3 L

| Compound | Cpd Type | Structure | Pa01 | Pa KW799/wt |
|---|---|---|---|---|
| YML-I-18 | Acetylated BisCatechol-Ampicillin | 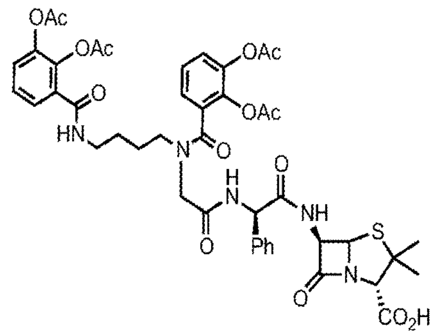 | | 0.0313μM<br>0.0156μM<br>.0156μM |
| YML-I-18cr | Acetylated BisCatechol-Ampicillin | 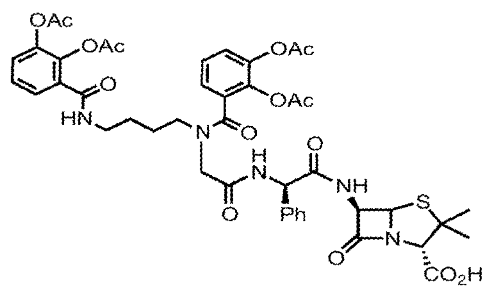 | .004μM<br>.0156μM | |
| YML-I-27 | Boc5 AminoHydroxyl aminoSuccinate-Ampicillin | 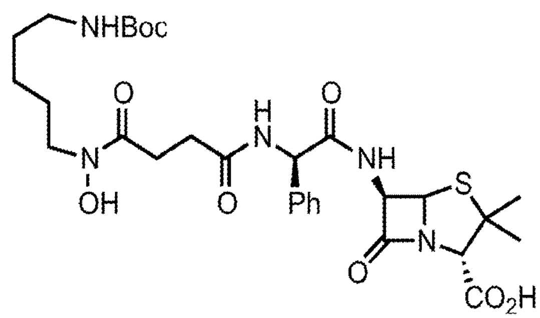 | | AD=0mm<br>AD=16Pmm |

Figure 3 M

| Compound | Cpd Type | Structure | Pa01 | Pa KW799/wt |
|---|---|---|---|---|
| YML-1-34cr | | YML-1-34cr R = H, Ac | | .39 μM |
| YML-1-45cr | | 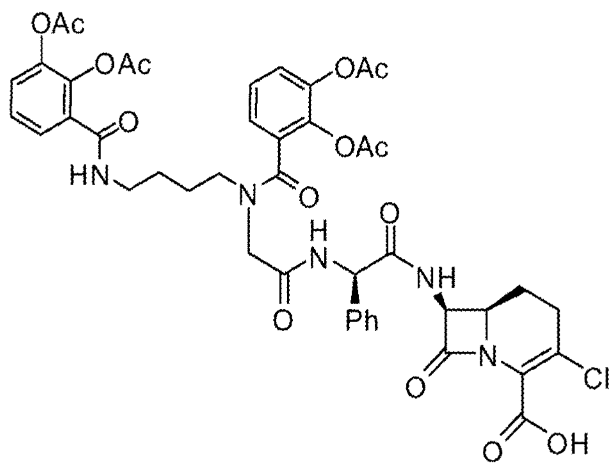 | | AD=18/26Pmm |

Figure 3 N
| Compound | Cpd Type | Structure | Pa01 | Pa KW799/wt |
|---|---|---|---|---|
| YML-1-47 | BisCatechol-Benzylethers free acid | 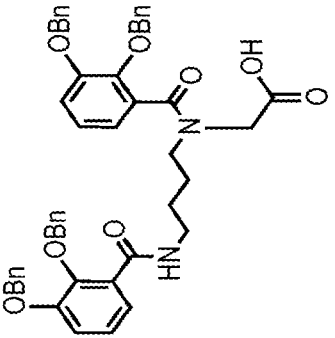 | >200μM | |
| YML-1-50cr | | 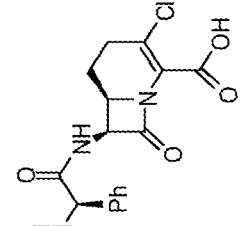  YML-1-50cr  R = H, Ac | | >200μM |

Figure 3 O

| Compound | Cpd Type | Structure | PaO1 | Pa KW799/wt |
|---|---|---|---|---|
| YML-1-54 | BisCatechol-t-Butyl ester | 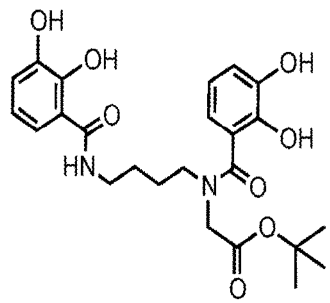 | >200μM | |
| YML-1-57 cr | | | | |
| YML-1-57 | Acetylated BisCatechol-loracarbef | 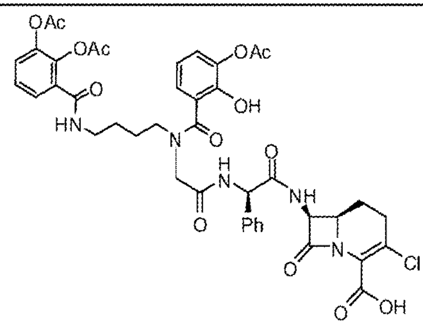 | .78μM 1.0μM | .025μM .033 |
| YML-1-58 | BisCatechol free acid | 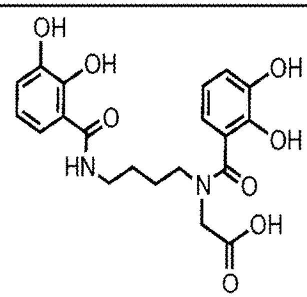 | >200μM | >200μM |

Figure 3 P
| Compound | Cpd Type | Structure | PaO1 | Pa KW799/wt |
|---|---|---|---|---|
| YML-1-60 | BisCatechol-loracarbef | 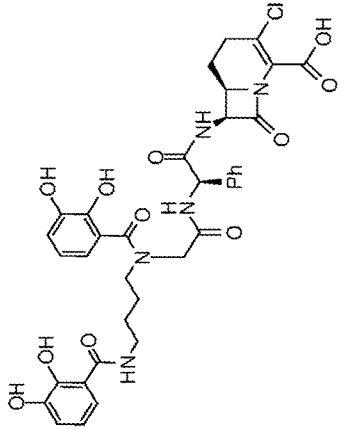 | 1.5 µM | .025 µM |
| YML-1-62 | BisCatechol-Ampicillin | 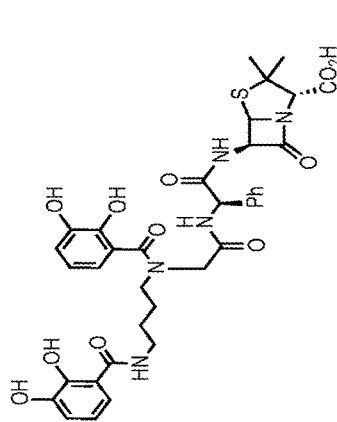 | .0156 µM | .0156 µM<br>0.025 µM |
| YML-1-77 | BisCatechol-aztreonam Hunig's Base salt | 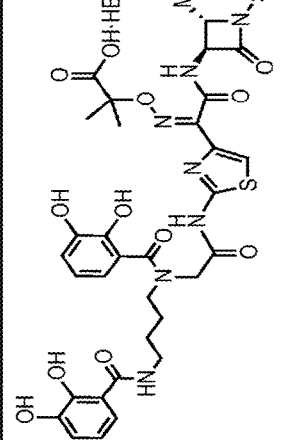 | 1.56 µM | 0.2 µM |

Figure 3 Q
| Compound | Cpd Type | Structure | Pa01 | Pa KW799/wt |
|---|---|---|---|---|
| Aztreonam | antibiotic | 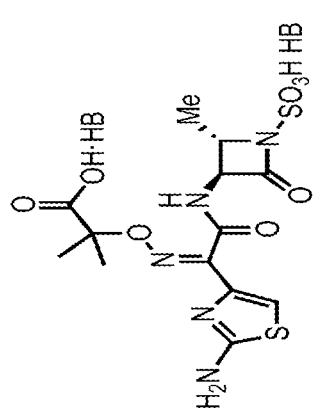 | 6.25µM | 1.56µM |
| YML-1-78 | BisCatechol-aztreonam K salt | 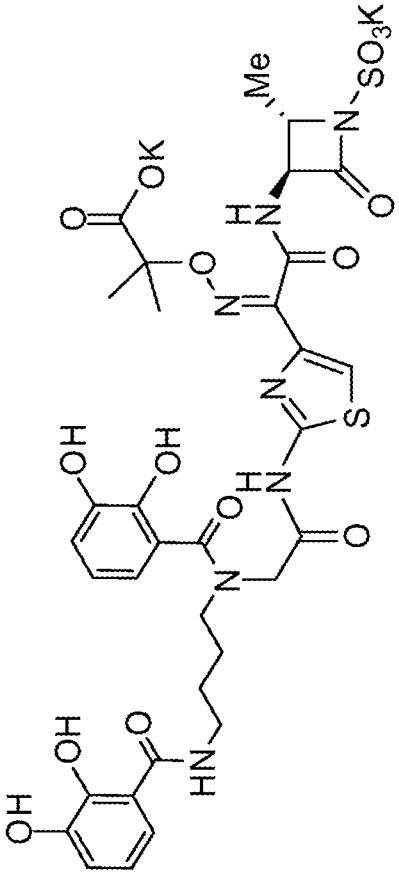 | >50µM | 0.78µM |

Figure 3 R
| Compound | Cpd Type | Structure | Pa01 | Pa KW799/wt |
|---|---|---|---|---|
| YML-1-80 | BisCatechol-pleuromutilin | 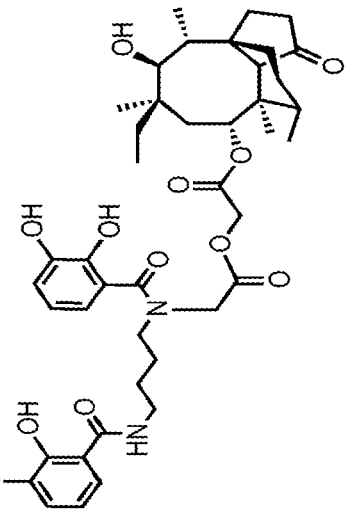 | | |
| Pleuromutilin | antibiotic | 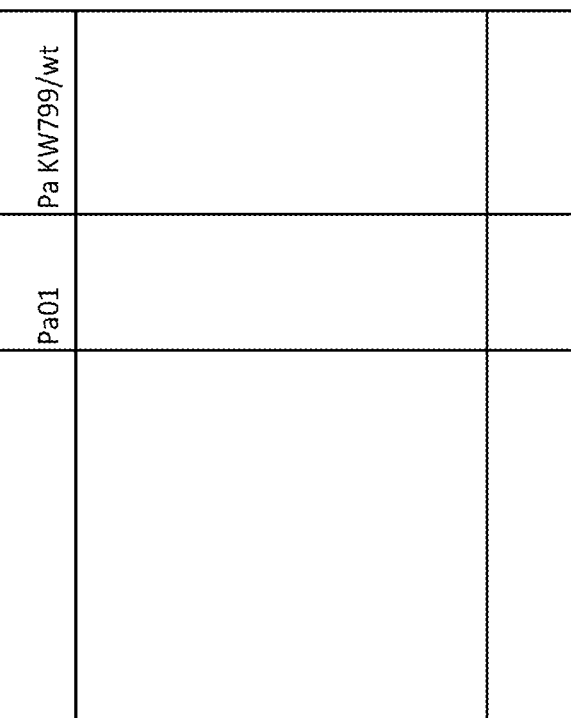 | | 200μM |

Figure 3 S

| Compound | Cpd Type | Structure | Pa01 | Pa KW799/wt |
|---|---|---|---|---|
| YML-1-91 | | 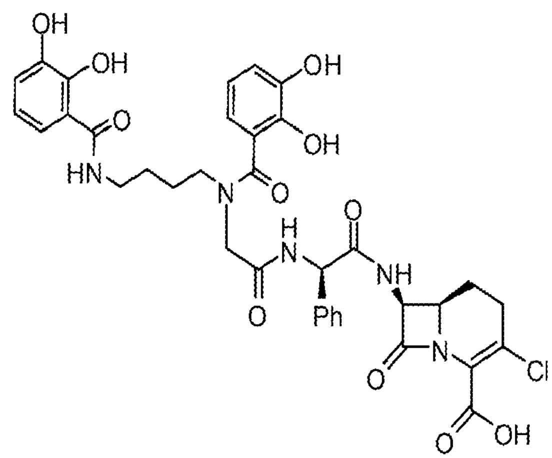 | .25μM | 0.05μM |
| YML-1-93 | | 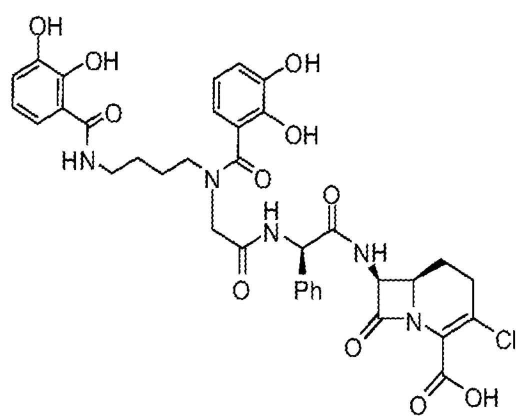 | .25-.5μM | 0.05μM |

Figure 3 T

| Compound | Cpd Type | Structure | Pa01 | Pa KW799/wt |
|---|---|---|---|---|
| YML-1-96 | | (structure: benzimidazole with 5-nitrofuran and tert-butyl carbamate-ethoxy substituent) | | |
| loracarbef | antibiotic | | >200μM | >200μM |
| Ampicillin | antibiotic | | >200μM | >200μM |
| cefaclor | antibiotic | | | >50μM |
| YML-1-104 | | (structure: bis-catechol cephalosporin conjugate with sodium carboxylate) | | |

Figure 3 U
| Compound | Cpd Type | Structure | | Pa01 | Pa KW799/wt |
|---|---|---|---|---|---|
| YML-1-105 Sulbactam | | 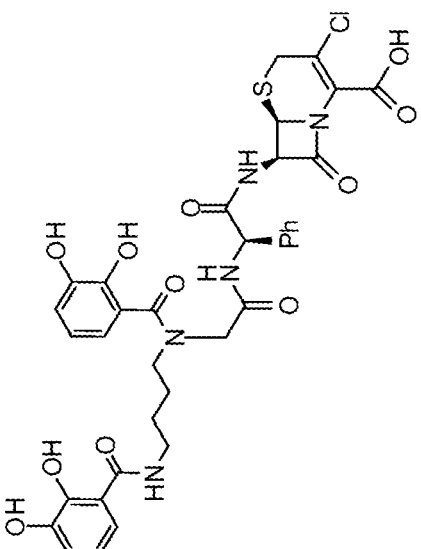 | | 6.25µM >80ug/ml | 0.78µM-1.56µM >80ug/ml zone @ .5mM=17.5P |
| YML-1-96 | | 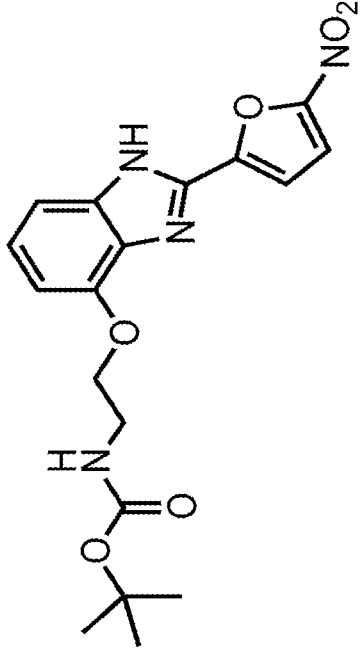 | | | |

Figure 3 V
| Compound | Cpd Type | Structure | Pa01 | Pa KW799/wt |
|---|---|---|---|---|
| YML-1-104 (not pure) | | 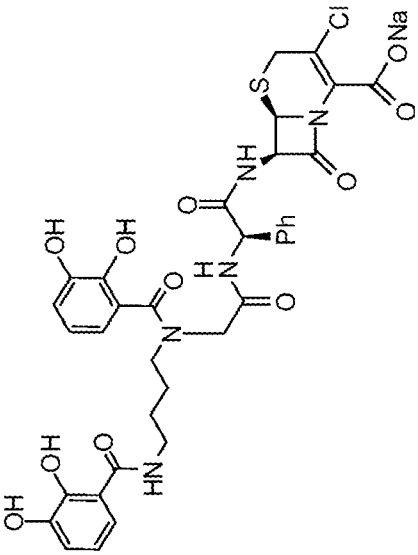 | 1.56μM | 0.233μM |
| YML-1-105 (not pure) | | 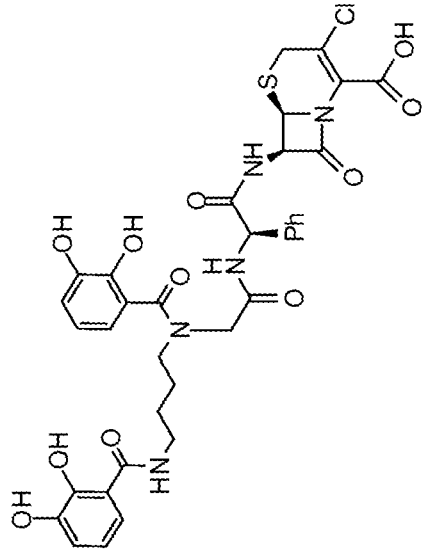 | 3.13μM 6.25μM | .78-1.56μM |
| cefaclor | | | >50μM | >50μM |

Figure 3 W
| Compound | Cpd Type | Structure | | Pa01 | Pa KW799/wt |
|---|---|---|---|---|---|
| YML-1-109 | | 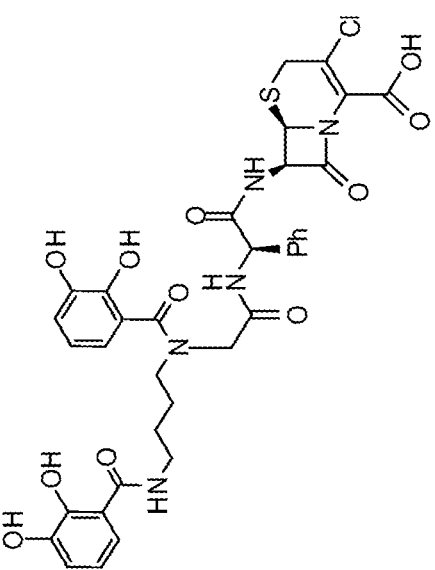 | | 1.56µM | 0.05µM |
| YML-1-115 (sodium salt of YML-1-60) | | 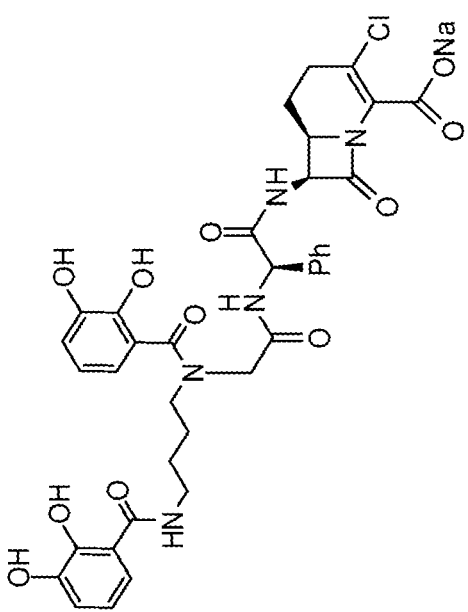 | | | |

Figure 3 X

| Compound | Cpd Type | Structure | Pa01 | Pa KW799/wt |
|---|---|---|---|---|
| YML-1-117 | | 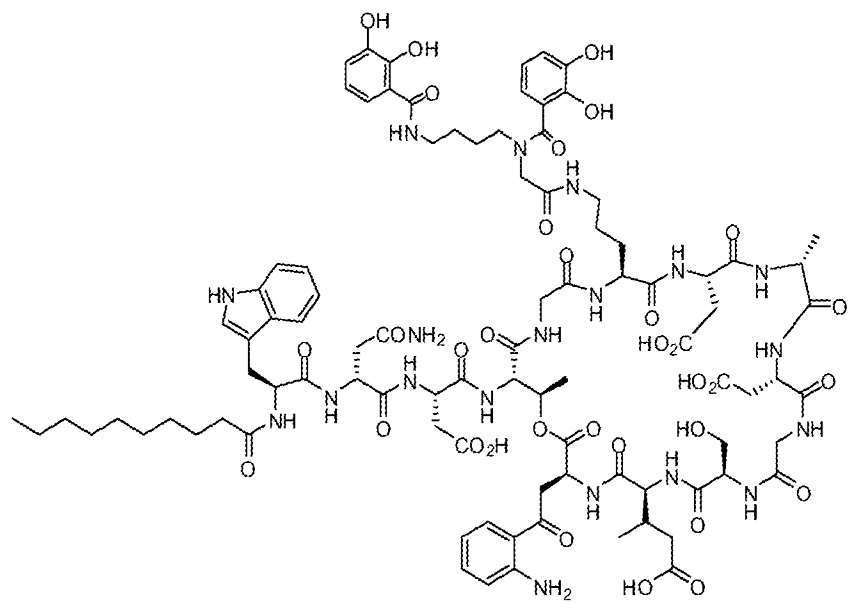 | | >100µM |

| Compound | Cpd Type | Structure | Pa01 | Pa KW799/wt |
|---|---|---|---|---|
| YML-1-119 (crude) | | 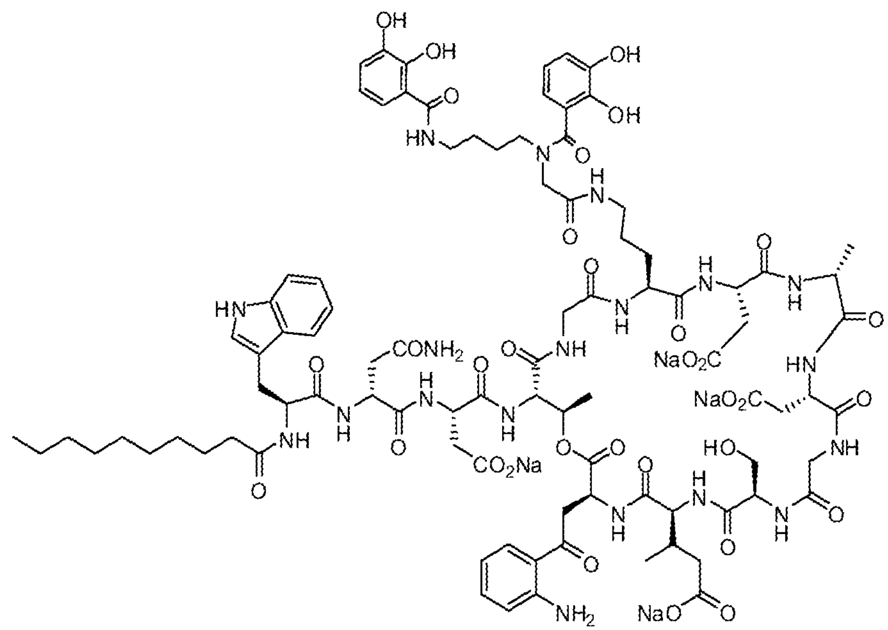 | | >200µM |

| Compound | Cpd Type | Structure | Pa01 | Pa KW799/wt |
|---|---|---|---|---|
| YML-1-120 (crude) | | 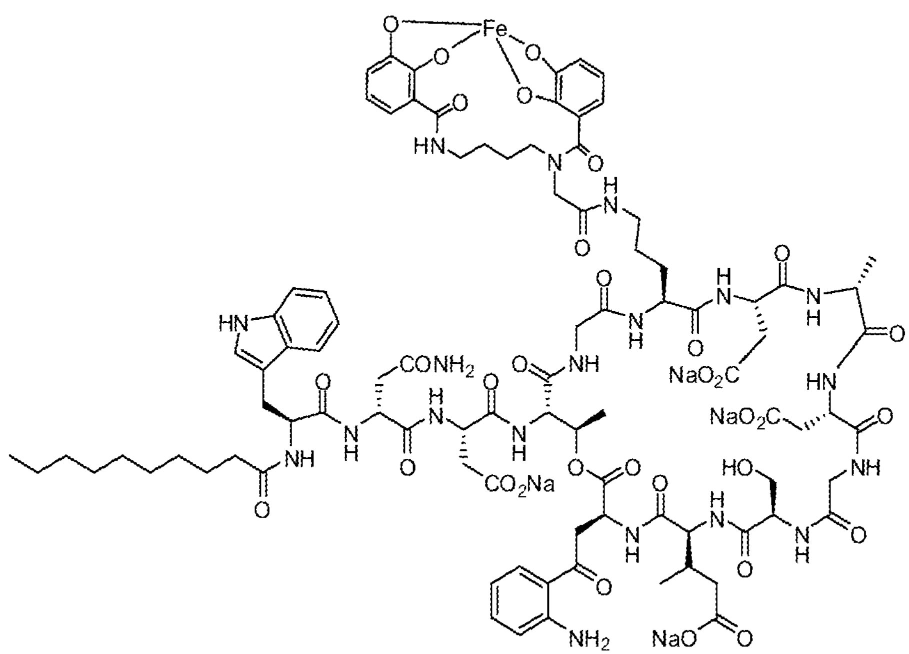 | | >200µM |

Figure 4. Agar diffusion assay demonstrating growth inhibitory activity of daptomycin sideromycins against multi-drug resistant *A. baumannii* 1710.
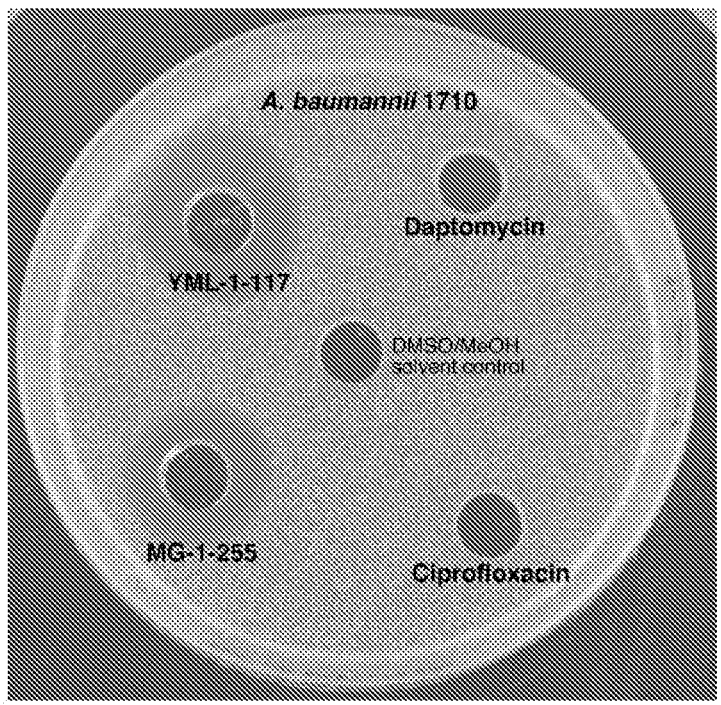

Figure 5 shows *in vitro* activity of daptomycin sideromycins HT-10 (tetrasodium salt of MG-255) against multi-drug resistant Acinetobacter (dose dependent agar diffusion). Note Daptomycin is not active (arrow).
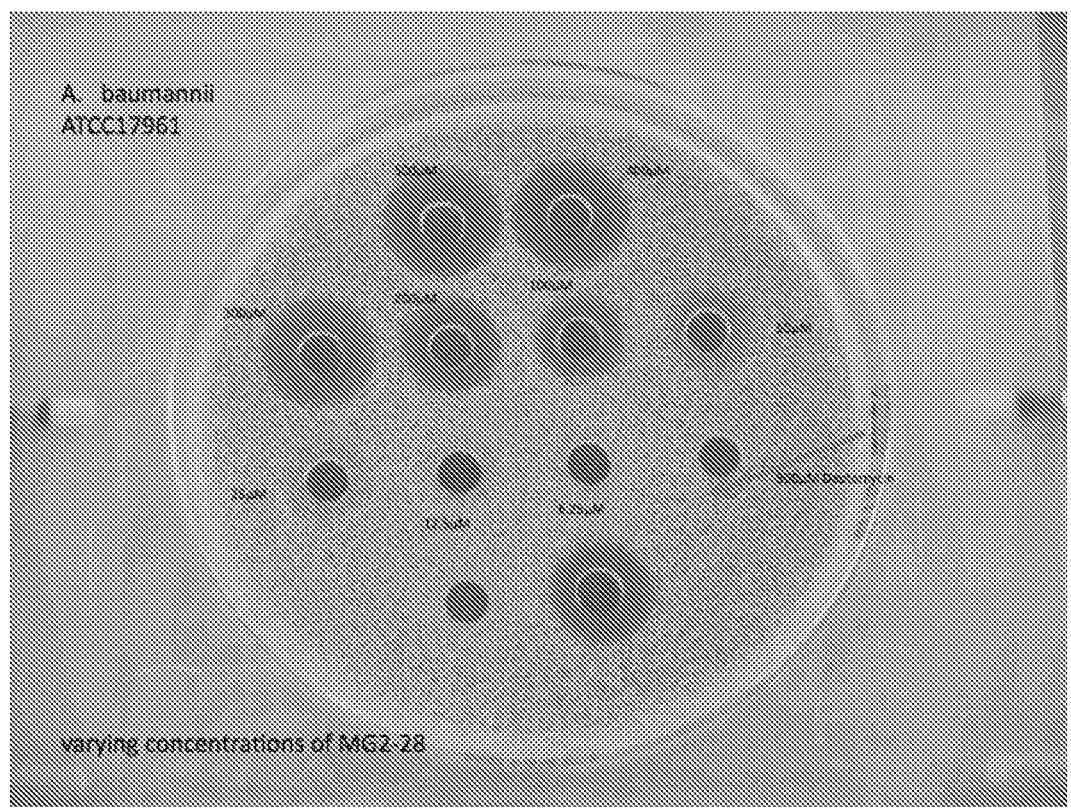

Figure 6 shows in vitro activity of HT-10 (tetrasodium salt of MG-255) against multi-drug resistant *Acinetobacter* (Raw MIC data).
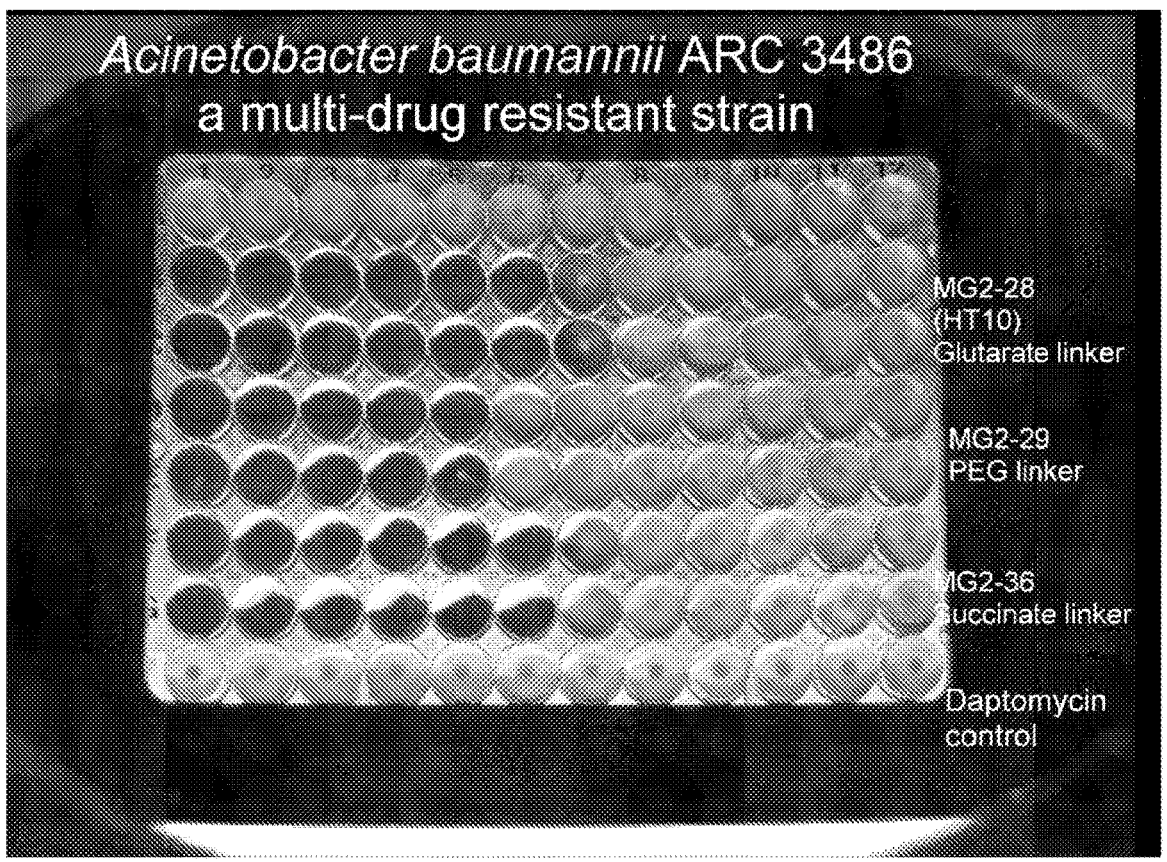

Figure 7 shows *in vivo* activity of HT-10 (tetrasodium salt of MG-255) against *Acinetobacter baumannii* in mice.
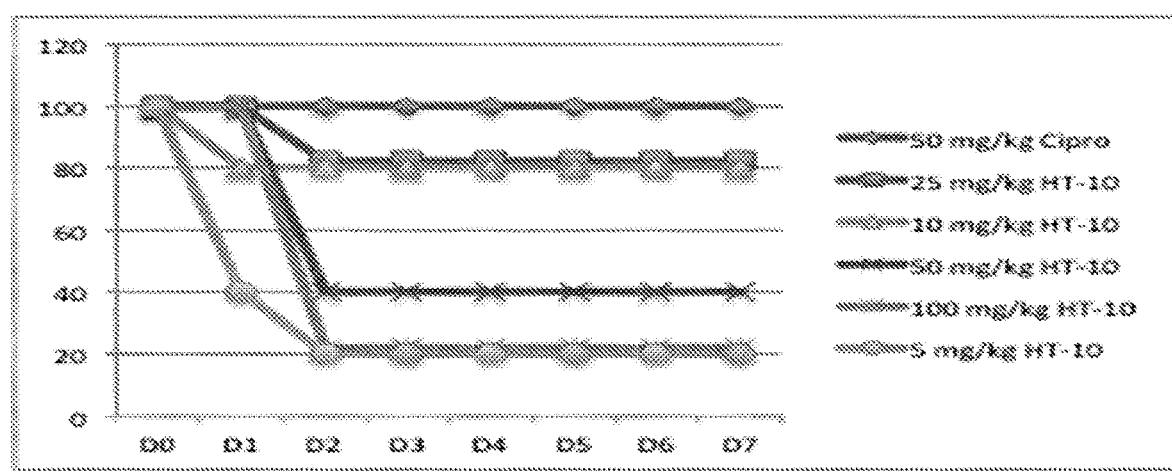

Figure 8 presents preliminary biological analysis of YML-1-45. (See also Scheme 6)
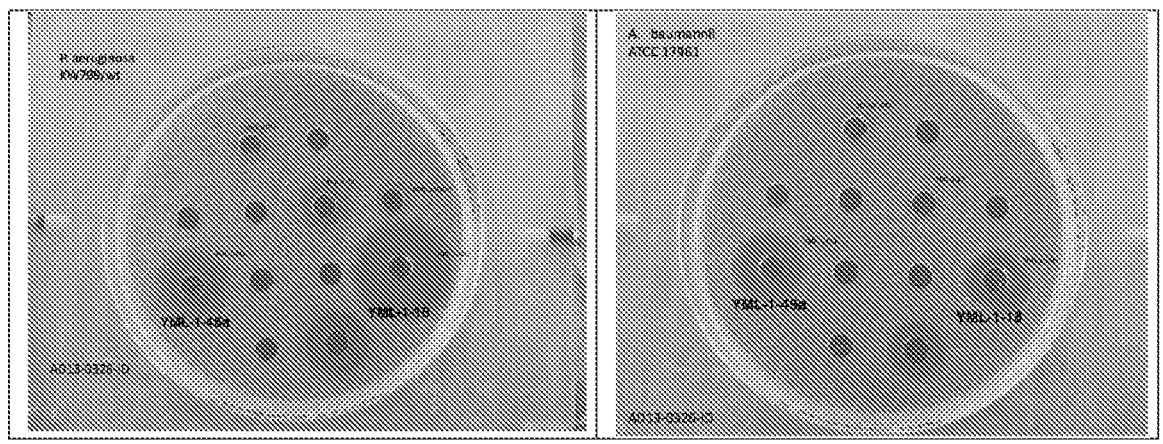

Figure 9 shows zones of inhibition against wild type *Pseudomonas* (Figure 9 left panel) and *Acinetobacter* (Figure 9 right panel).
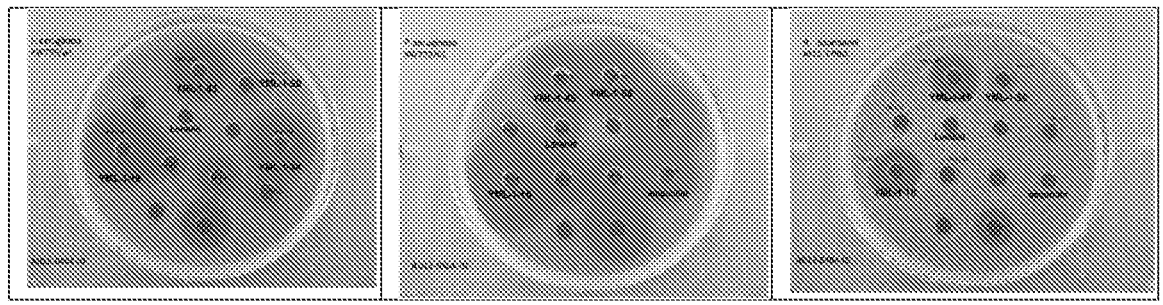

Figure 10 presents gel studies.
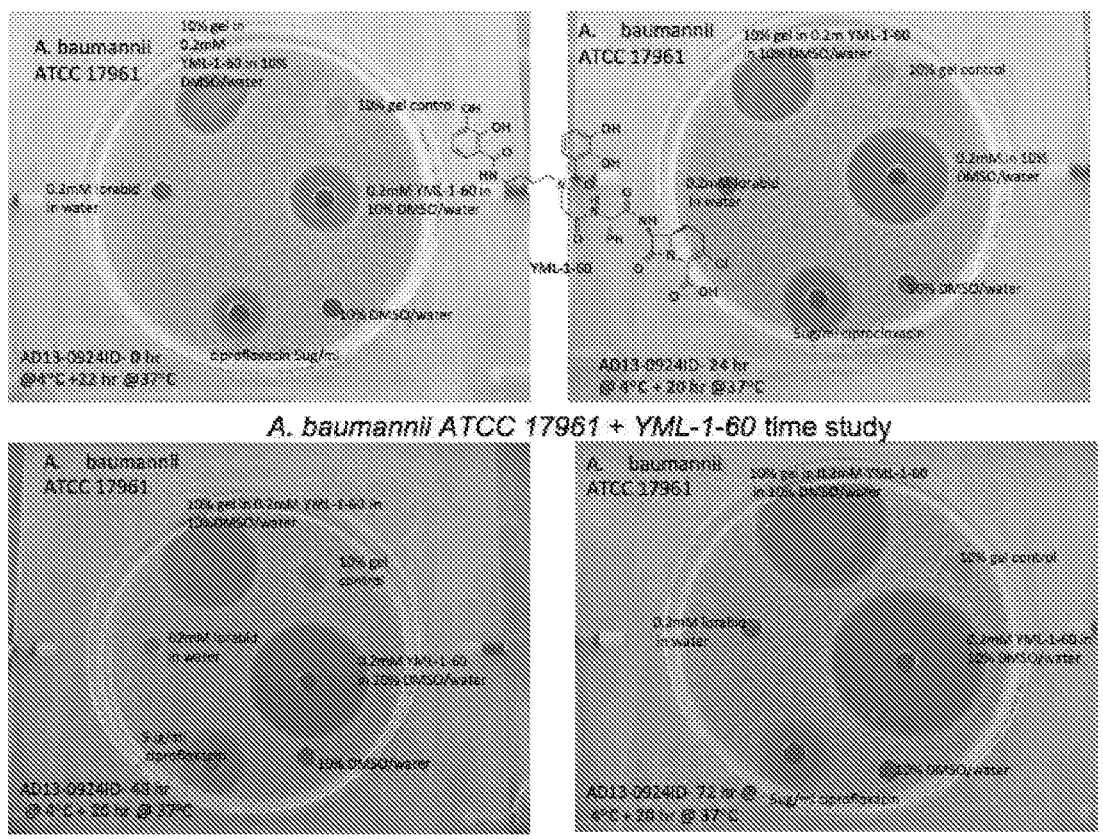
*A. baumannii ATCC 17961 + YML-1-60 time study*

Figure 11 presents structure and gel studies.
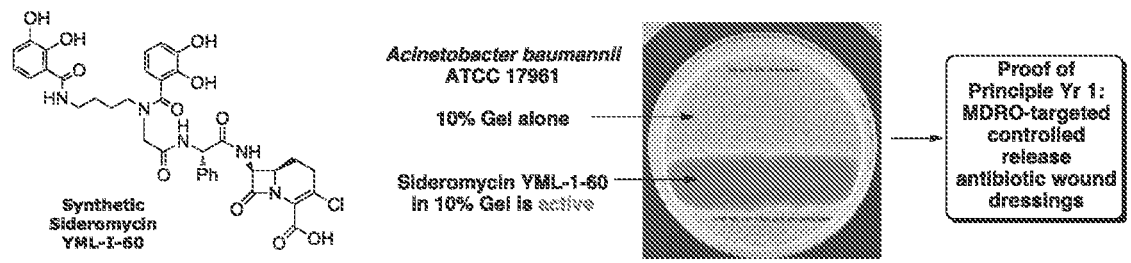

Figure 12 shows multi-day studies
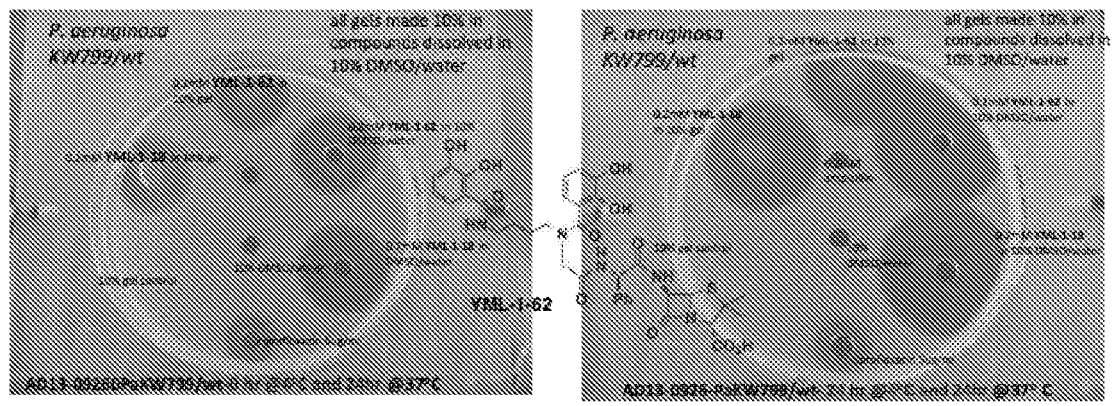
P. aeruginosa KW799/wt + YML-1-18 & YML-1-62 time study for 96 hr
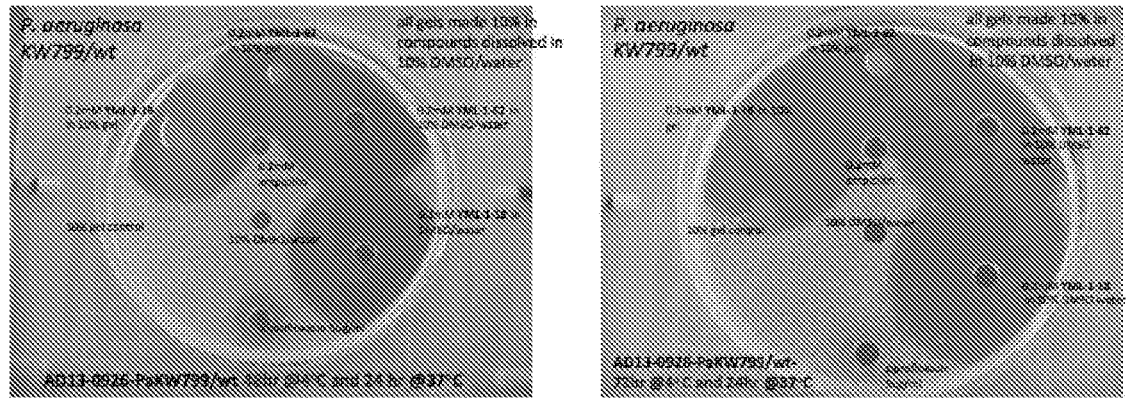

Figure 13-1. Peak overlay for both YML-1-60 and YML-1-90
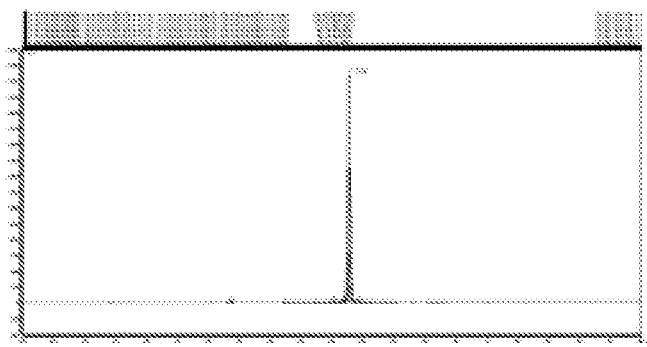
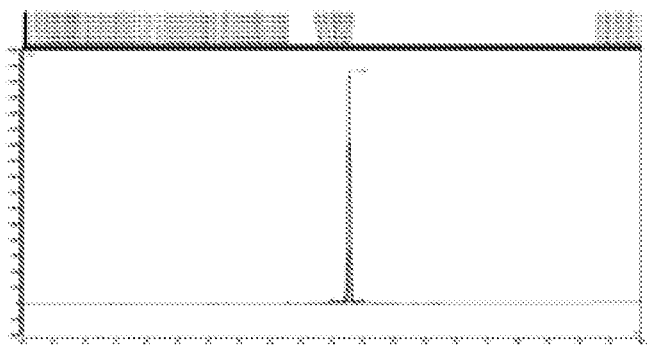

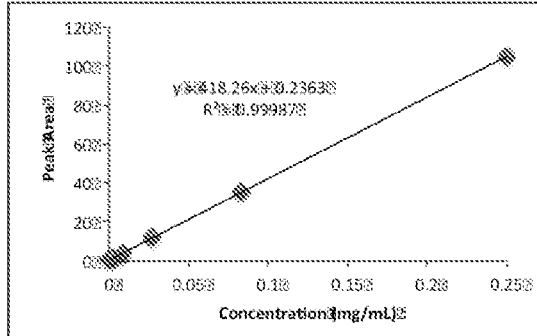# Figure 13-2. Standard curve for YML-1-60
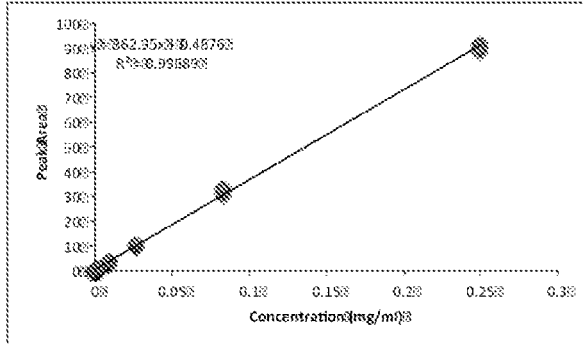# Figure 13-3. Standard curve for YML-1-90

Figure 13-4. Retention of potassium clavulanate in YML-1-60
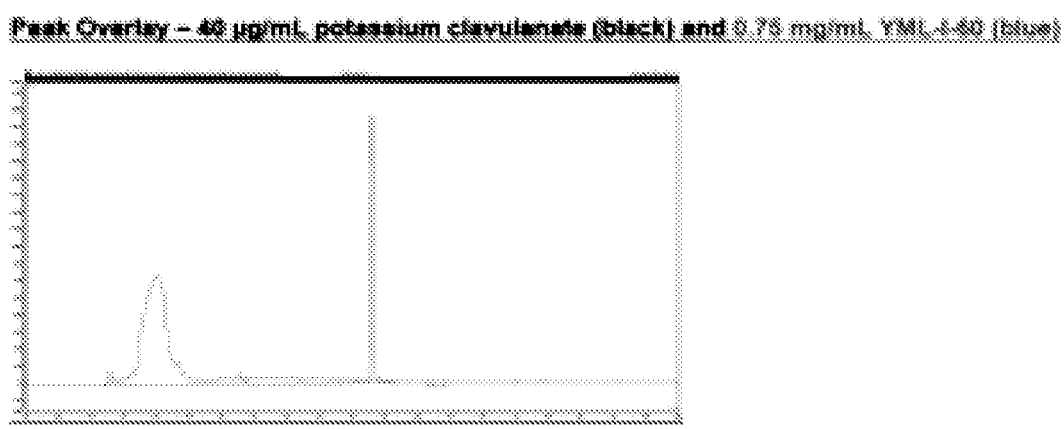

Figure 13-5. *A. baumannii ATCC 17961* + MG-1-189 time study for 96 h. Interestingly, MG-1-189 did not show any toxicity in Cytotoxicity assay: PC3 ; MCF7; Hela: IC50 >20 µM.
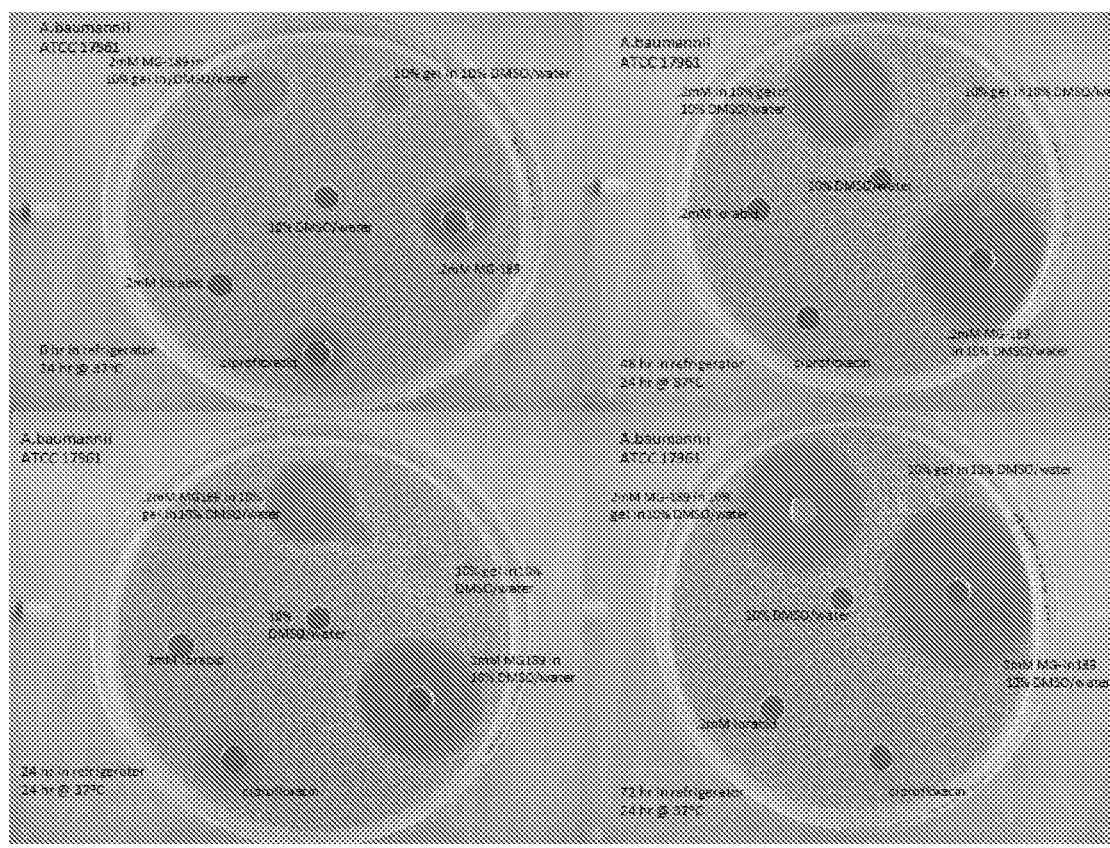

Figure 14 shows graphically the *in-vivo* data for murine survival experiments with *acinetobacter* (See also Table 9).
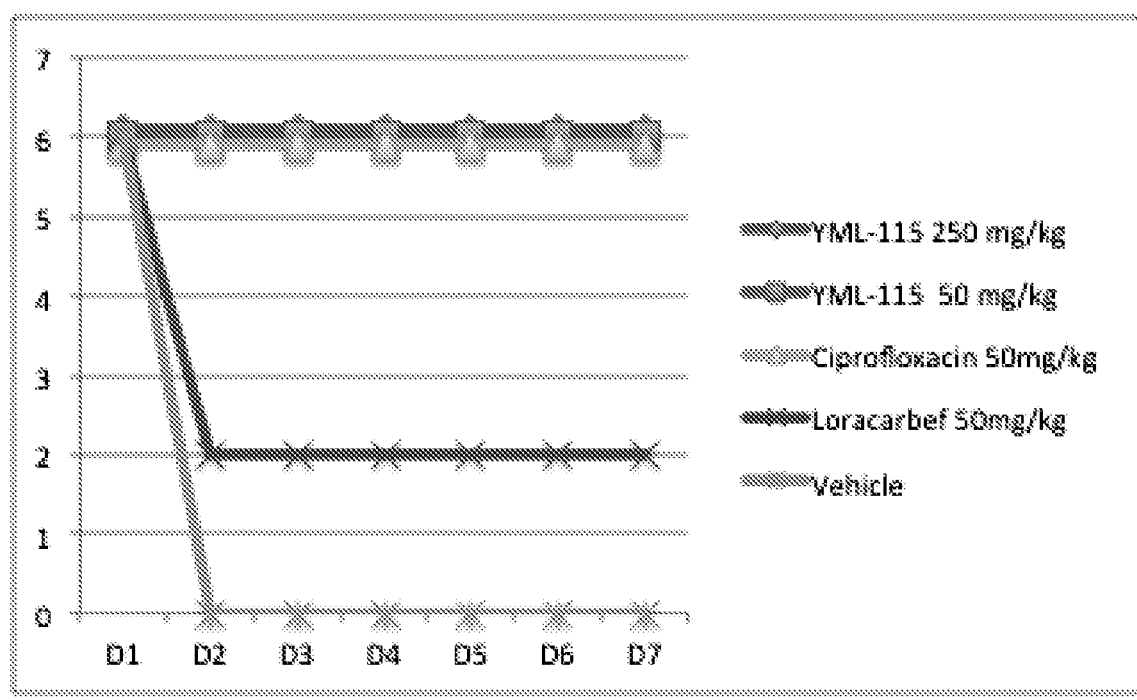

ANTIBACTERIAL SIDEROMYCINS

This application claims priority to U.S. Provisional Application No. 62/039,405 filed Aug. 19, 2014

This invention was made with government support under Contract No. W81XWH-12-2-0115 awarded by US Medical Research Acquisition Activity & US Army Medical Research and Materiel Command. The government has certain rights in the invention.

BACKGROUND

The need for new antibiotics is dire. Since 1920, the average life span of people living in the US has increased more than 50%. Nothing in human history can compare to such a change in only three generations. Over half of that remarkable change is due to the advent of modern antibiotic therapy. During the 1940s-1970s (the "golden era of antibiotics), several classes of antibacterial agents were discovered and developed, including beta-lactams (penicillins, cephalosporins, carbapenems), macrolides (erythromycins), am inoglycosides, streptomycins and vancomycin. Unfortunately, therapeutic advantages are being compromised by the development of microbial resistance to every known antibiotic. Hospital-borne infections are of special concern in that over 2 million patients acquire nosocomial infection annually, accounting for over 90,000 deaths. Over 70% of these cases are caused by drug resistant bacteria. Resistance occurred rapidly to each type of antibiotic and was exacerbated by extensive overuse of antibiotics. Bacterial adaptation results in changes of membrane permeability through porin modification, evolution of enzymes that deactivate antibiotics, and use of efflux pumps to decrease intracellular drug concentration.

Despite considerable effort over the 35 years prior to the end of the 20th century, no new class of antibiotics was introduced to the clinic until the development of the oxazolidinones.

Daptomycin (1) (shown in FIG. 1) is a lipopepide that was first discovered in the late 1980s and was referred to as LY 146032. Despite its complex structure and, concerns about lability of the peptide, it showed efficacy in clinical trials for treatment of Gram-positive bacterial infections. The antibiotic was approved in 2003 and is marketed as Cubicin for selected intravenous treatment of Gram-positive infections. Daptomycin works by disrupting bacterial membrane function. It inserts into and aggregates in the cell membrane and induces changes that induce depolarization and eventual inhibition of protein, DNA, and RNA biosynthesis.

While it is bactericidal against Gram-positive bacteria, daptomycin alone is not active against Gram-negative bacteria. The molecular weight of daptomycin is about 1620 g/mol. Most Gram-negative antibacterial agents must passively diffuse through porins in the additional outer membrane. Porin size and function restrict passive diffusion of compounds, including antibiotics, to relatively small compounds having molecular weights of typically less than 700 g/mol. Thus, despite being a potential target for daptomycin, Gram-negative bacteria are protected from its action by its inability to permeate the outer cell wall.

Despite porin restriction, bacteria must assimilate nutrients. One nutrient that is absolutely essential for growth of virtually all forms of life, including bacteria, is iron. Competition for iron between a host and pathogenic bacteria is one of the most important factors in determining the course of a bacterial infection. Due to the extreme insolubility of ionic forms of iron, bacteria and fungi have evolved highly specific iron sequestration processes that involve energy-dependent-active transport of relatively low-molecular-weight iron chelators called siderophores. Siderophores produced by invading bacteria are able to steal iron from the host's iron storage proteins, lactoferrin or transferrin during the course of an infection. Over 500 structurally distinct microbial siderophores have been identified to date. Their structural variation is often attributed to selective bacterial virulence in the severe competition for iron. In Gram-negative bacteria, iron-siderophore complexes are recognized and are bound by specific outer-membrane receptors (OMR) at the cell surface. Binding of the siderophore-iron complexes initiates the active transport process that translocates the iron complex, to the periplasm. This is followed by active transport through the inner membrane, mediated by periplasmic binding protein dependent ABC permeases, which exploit the electrochemical potential difference of the cytoplasmic membrane that is transduced to the outer membrane by the TonB-ExbB-ExbD complex. In Gram-positive bacteria, the iron-siderophore complexes are recognized by specific binding proteins anchored to the inner membrane and then transported by the ABC permeases. In all cases, recognition is followed by initiation of specific energy-dependent active transport processes. Nature has provided examples of iron transporters used to deliver toxic substances to bacteria, such as the albomycins (2), ferrimycin A1, (3) and the salmycins (4). Whereas siderophores are iron sequestering growth promoters for, bacteria, the albomycins, salmycins, and other natural siderophore-antibiotic conjugates are often referred to as sideromycins since they kill competitive bacteria using the so-called "Trojan Horse" concept, That is, competing bacteria take up the sideromycins in an attempt to assimilate pre-complexed iron but in so doing also ingest and actively transport the attached lethal agent and, in a sense, commit "bacterial suicide". The albomycins enter bacteria via the ferric hydroxamate transport-systems. The ferrichrome-like siderophore portion of the albomycins is recognized as the iron complex and transported by the ferrichrome associated proteins FhuA and FhuD. Once internalized, the toxic thionucleoside is enzymatically released by a serine protease to exert its toxic effect. The overall result was natural evolution of a siderophore-drug conjugate with outstanding microbial selectivity and activity (MIC=0.01 µg/mL) against Staphylococci and Streptococci, including multidrug resistant strains.

Natural and early examples of synthetic siderophore-antibiotic conjugates (sideromycins) are shown in Figure Z.

The salmycin class of naturally occurring sideromycins, isolated from *Streptomyces violaceus* DSM 8286, also exhibits potent antibacterial activity (MIC of 0.01 µg/mL against Staphylococci and Streptococci, including resistant strains). Similar to the albomycins, the salmycins appear to enter cells via ferric hydroxamate transport systems.

E-0702 (5) was proposed to enter into bacteria by the tonB-dependent iron-transport system. Subsequently, another catechol (e.g. L1310522, 6) and hydroxypyridone-substituted cephalosporin derivatives were prepared and shown to have significant antipseudomonal activity, presumably because iron chelation facilitated uptake by the otherwise antibiotic-resistant bacteria. Recently, the synthesis and detailed mode of action were described for MC-1 (7), a siderophore-monocarbam conjugate.

Despite the aforementioned advances, the need for antibiotics remains dire.

BRIEF DESCRIPTION OF THE SEVERAL EMBODIMENTS

This aforementioned specific and unique iron transport process has no mammalian counterpart, and we have found that it can be exploited to develop bacteria/fungi-selective antibiotic drug delivery systems. In one embodiment, such systems enable the targeting of infections including, but not limited to, *Pseudomonas aeruginosa*, strains of *Acinetobacter*, and other pathogenic bacteria. In one embodiment, iron transport-mediated (Trojan Horse) delivery circumvents certain types of common bacterial resistance mechanisms, especially resistance due to reduced cell wall permeability and efflux.

BRIEF DESCRIPTION OF THE FIGURES

FIG. 1 shows the structure of Daptomycin.

FIG. 2 presents natural and early examples of synthetic siderophore-antibiotic conjugates (sideromycins).

FIG. 4 presents agar diffusion assay demonstrating growth inhibitory activity of daptomycin sideromycins against multi-drug resistant *A. baumannii* 1710.

FIG. 5 presents in vitro activity of daptomycin sideromycins HT-10 (tetrasodium salt of MG-255) against multi-drug resistant *Acinetobacter* (dose dependent agar diffusion). Note Daptomycin is not active (arrow).

FIG. 6 presents in vitro activity of HT-10 (tetrasodium salt of MG-255) against multi-drug resistant *Acinetobacter*. (Raw MIC data).

FIG. 7 presents in vivo activity of HT-10 (tetrasodium salt of MG-255) against *Acinetobacter baumannii* in mice.

FIG. 8 presents preliminary biological analysis of YML-1-45. (See also Scheme 6).

FIG. 9 presents of inhibition against wild type *Pseudomonas* (FIG. 9 left panel) and *Acinetobacter* (FIG. 9 right panel).

FIG. 10 presents gel studies.

FIG. 11 presents structure and gel studies.

FIG. 12 presents multi-day studies

FIG. 13-1 presents peak overlay for both YML-1-60 and YML-1-90.

FIG. 13-2 presents standard curve for YML-1-60.

FIG. 13-3 presents standard curve for YML-1-90.

FIG. 13-4 presents retention of potassium clavulanate in YML-1-60.

FIG. 13-5 presents *A. baumannii* ATCC 17961+MG-1-189 time study for 96 h.

FIG. 14 presents graphically the in-viva data for murine survival experiments with *acinetobacter*.

DETAILED DESCRIPTION OF THE SEVERAL EMBODIMENTS

Figure 3:
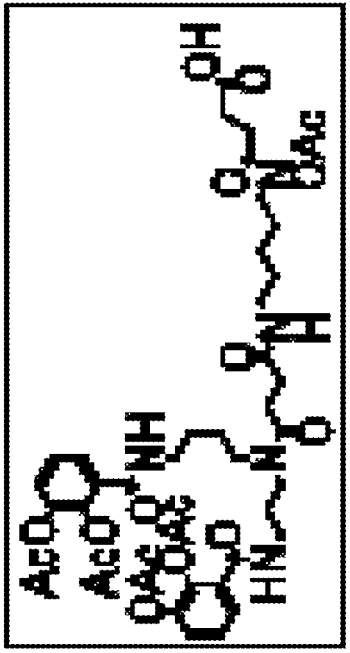
FIG. 3 presents various combinations of siderophores, linkers, and conjugates.
Figure 3:
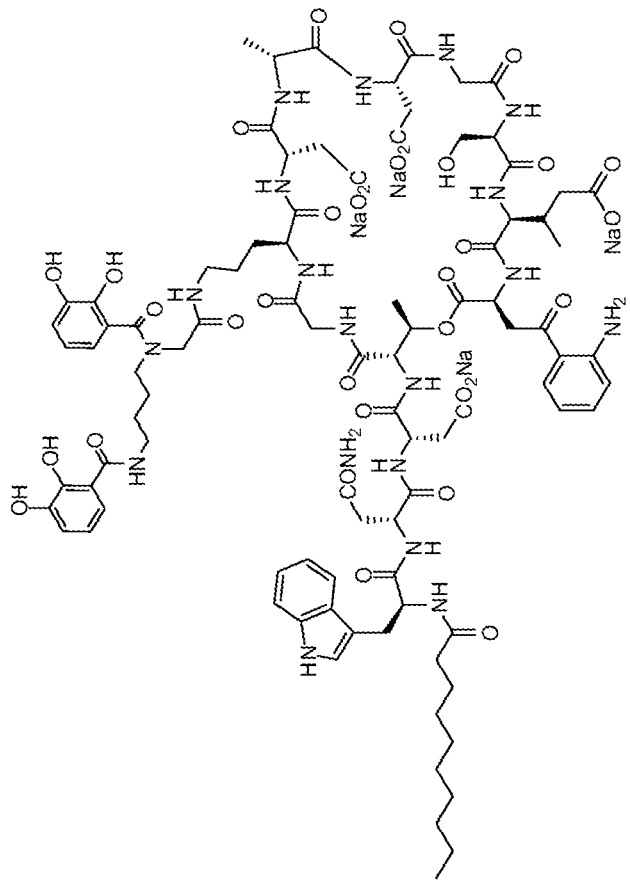
Figure 3:
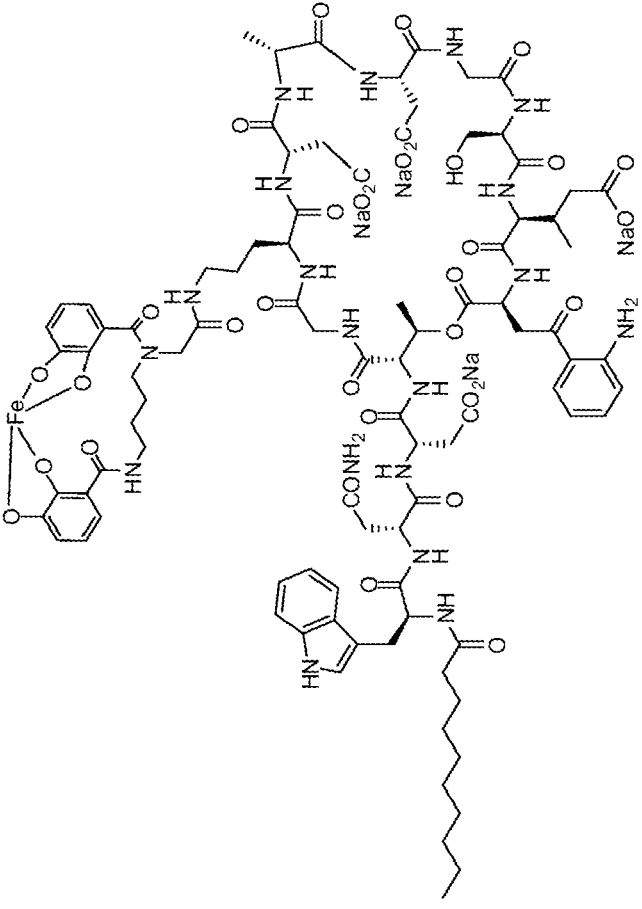

One embodiment provides a compound, comprising;
an Fe(III)-binding siderophore;
one or more optional linker covalently bound to the siderophore; and
daptomycin covalently bound to the linker, or, if no linker is present, then to the siderophore;
or pharmaceutically acceptable sailor solvate thereof.

Another embodiment provides a compound, comprising:
an Fe(III)-bound siderophore;
one or more optional linker covalently bound to the siderophore; and
daptomycin covalently bound to the linker, or, if no linker is present, then to the siderophore;
or pharmaceutically acceptable salt or solvate thereof.

3. The compound of claims 1 or 2, wherein the siderophore comprises a natural siderophore, semi-synthetic siderophore, synthetic siderophore, or combination thereof.

4. The compound of claims 1 or 2, wherein the siderophore comprises one or more iron(III)-binding ligand.

5. The compound of claims 1 or 2, wherein the siderphore comprises one or more iron(III)-binding catechol, hydroxamic acid, beta-hydroxy acid, heteroaromatic ligand, or combination thereof.

6. The compound of claims 1 or 2, having one of the following formulas:

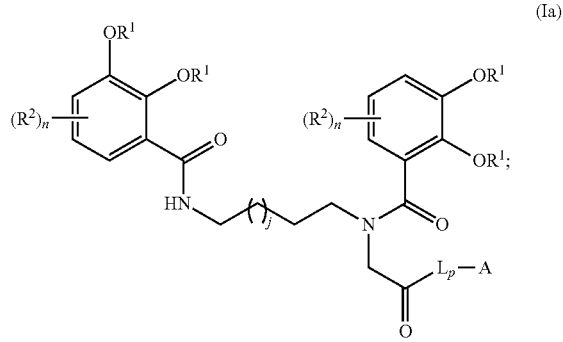

(Ia)

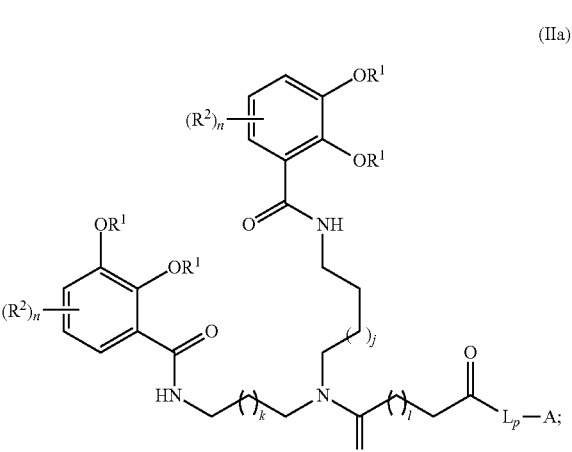

(IIa)

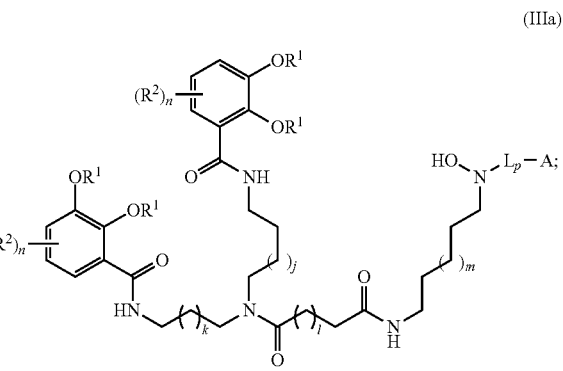

(IIIa)

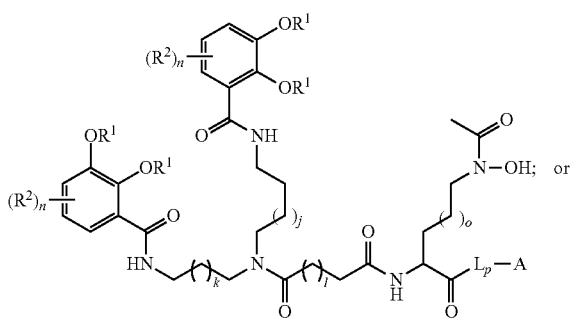

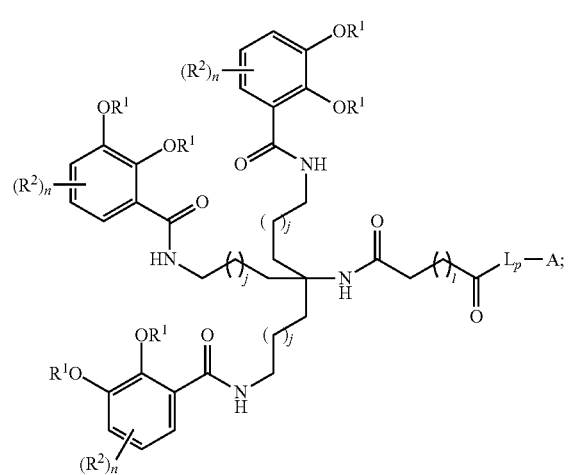

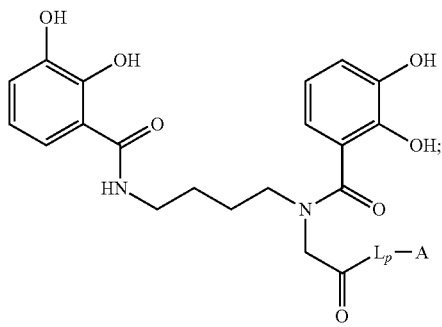

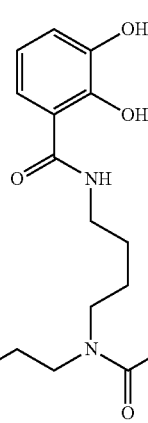

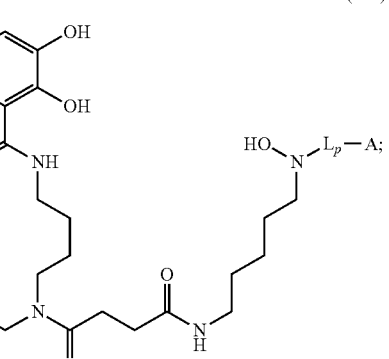

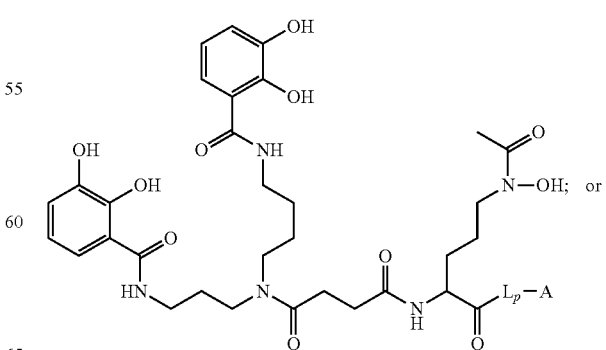

wherein

A is daptomycin;

each L is independently a linker;

each $R^1$ is independently H, —C(=O)alkyl, —C(=O)aryl, or —C(=O)O-alkyl;

each $R^2$ is independently H, alkyl, alkoxy, hydroxy, carboxy, halo, nitro, amino, or cyano;

each n is independently 1, 2, or 3;

each p is independently 0-11;

each j is independently 0-11;

each k is independently 1-11;

each l is independently 1-11;

each o is independently 0-11; and each m is independently 0-11;

Fe(III)-bound form thereof, pharmaceutically acceptable salt thereof, solvate thereof, or combination thereof.

7. The compound of claims 1 or 2, having one of the following formulas:

(Vb)

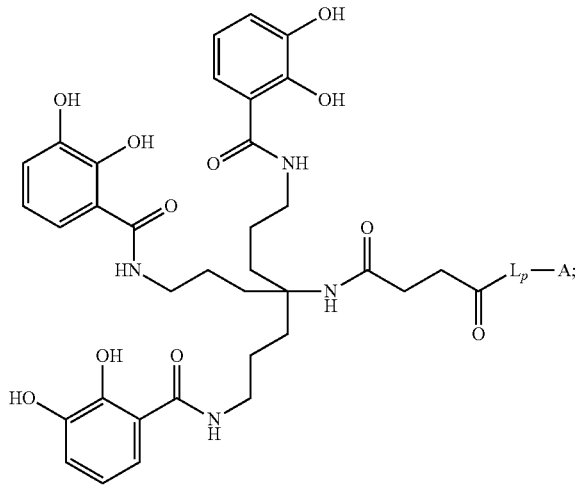

wherein
A is daptomycin;
each L is independently a linker; and
each p is independently 0-11;
Fe(III)-bound form thereof, pharmaceutically acceptable salt thereof, solvate thereof, or combination thereof.

8. The compound of claims 1 or 2, wherein one or more than one linker is present.

9. The compound of claims 1 or 2, wherein more than one type of linker is present.

10. The compound of claims 1 or 2, wherein no linker is present.

Another embodiment provides a pharmaceutical composition, comprising the compound(s) or mixture thereof and a pharmaceutically acceptable diluent or carrier.

Another embodiment provides a composition, further comprising a hydrogel.

Another embodiment provides a composition, further comprising a beta-lactamase inhibitor.

Another embodiment provides a composition, further comprising a beta-lactamase inhibitor, wherein the beta-lactamase inhibitor is sulbactam, tazobactam, potassium clavulanate, or combination thereof.

Another embodiment provides a method for treating a bacterial infection in a subject, comprising administering the compound to the subject.

Another embodiment provides a method for treating a bacterial infection in a subject, comprising administering the composition to the subject.

Another embodiment provides a method for killing or inhibiting the growth of a bacterium, comprising contacting the bacterium with the compound or composition Another embodiment provides a compound, comprising:
an Fe(III)-binding siderophore;
one or more optional linker covalently bound to the siderophore; and
an antibiotic covalently bound to the linker, or, if no linker is present, then to the siderophore;
or pharmaceutically acceptable salt or solvate thereof.

Another embodiment provides a compound, comprising;
an Fe(III)-bound siderophore;
one or more optional linker covalently bound to the siderophore; and
an antibiotic covalently bound to the linker, or, if no linker is present, then to the siderophore;
or pharmaceutically acceptable salt or solvate thereof.

In some embodiments, the antibiotic is amikacin, aminoglycoside, amoxicillin, amphotericin, ampicillin, ansamycin, azithromycin, aztreonam, bacillomycin, BAL30072, beta-lactam, biapenem, carbacephalosporins, carbapenem, carbomycin, carbomycin A, carumonam, cefaclor, cefalotin, cephalosporin, cethromycin, chloramphenicol, chlortetracycline, ciprofloxacin, clarithromycin, clindamycin, cycloserine, daptomycin, demeclocycline, dirithromycin, doripenem, doxorubicin, doxycycline, ertapeneme, erythromycin, ethambutol, fluoroquinolone, gentamicin, imipenem, isoniazid, josamycin, kanamycin, kitasamycin, lincomycin, linezolid, loracarbef, macrolide, meropenem, methacycline, midecamycin, monobactam, mupirocin, neomycin, nystatin, oleandomycin, oleandomycin, oxazolidinones, oxytetracycline, panipenem, penem, penicillin, peptide antibiotic, polymixin, pyrrolnitrin, quinolone, rifampin, rifamycins, rolitetracycline, roxithromycin, solithromycin, spiramycin, streptomycin, sulfabenzamide, sulfacetamide, sulfadiazine, sulfadoxine, sulfamerazine, sulfamethazine, sulfamethizole, sulfamethoxazole, sulfisoxazole, sulfonamide, telithromycin, tetracycline, tigimonam, troleandomycin, tylosin, tylocine, vancomycin, or zyvox.

In some embodiments, the siderophore comprises a natural siderophore, semi-synthetic siderophore, synthetic siderophore, or combination thereof.

In some embodiments, the siderophore comprises one or more iron(III)-binding ligand.

In some embodiments, the siderphore comprises one or more iron(III)-binding catechol, hydroxamic acid, beta-hydroxy acid, heteroaromatic ligand, or combination thereof.

In some embodiments, the siderophore-linker-antibiotic has one of the following formulas:

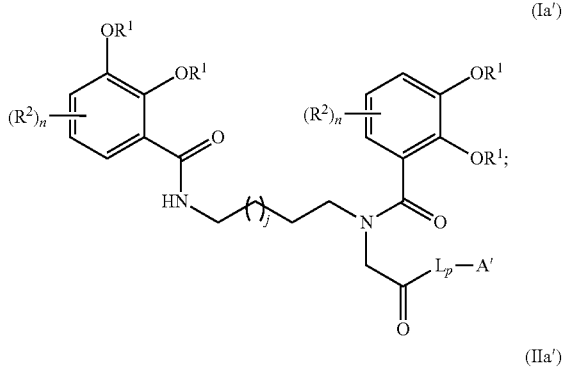
(Ia')

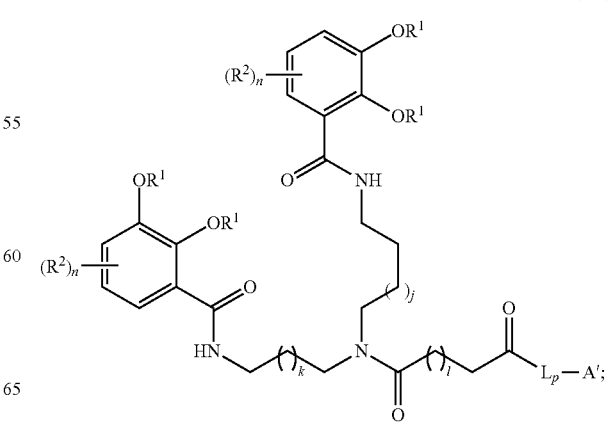
(IIa')

-continued

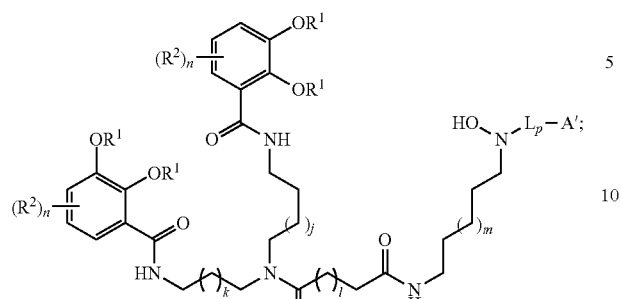
(IIIa')

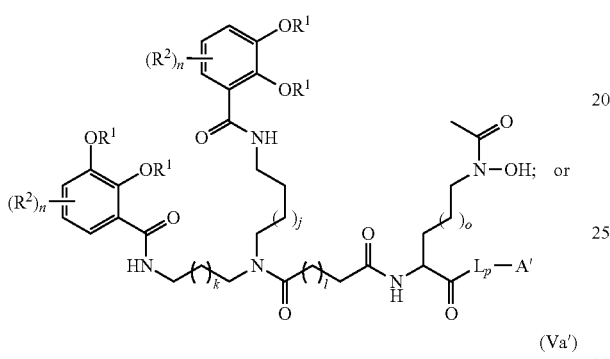
(IVa')

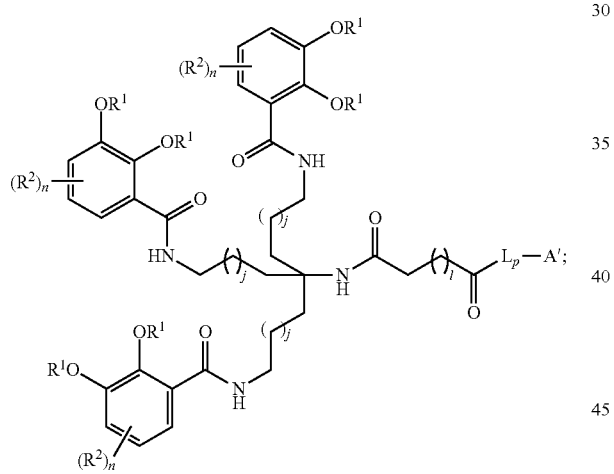
(Va')

wherein
A' is antibiotic;
each L is independently a linker;
each $R^1$ is independently H, —C(═O)alkyl, —C(═O)aryl, or —C(═O)O-alkyl;
each $R^2$ is independently H, alkyl, alkoxy, hydroxy, carboxy, halo, nitro, amino, or cyano;
each n is independently 1, 2, or 3;
each p is independently 0-11;
each j is independently 0-11;
each k is independently 1-11;
each l is independently 1-11;
each o is independently 0-11; and
each m is independently 0-11;
Fe(III)-bound form thereof, pharmaceutically acceptable salt thereof, solvate thereof, or combination thereof.

In some embodiments, the siderophore-linker-antibiotic has one of the following formulas:

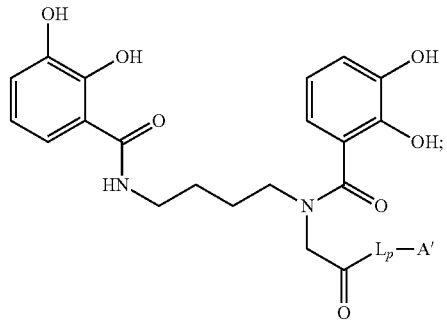
(Ib')

(IIb')

(IIIb')

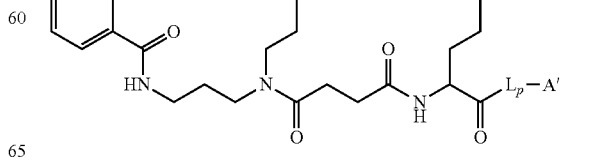
(IVb')

-continued (Vb')

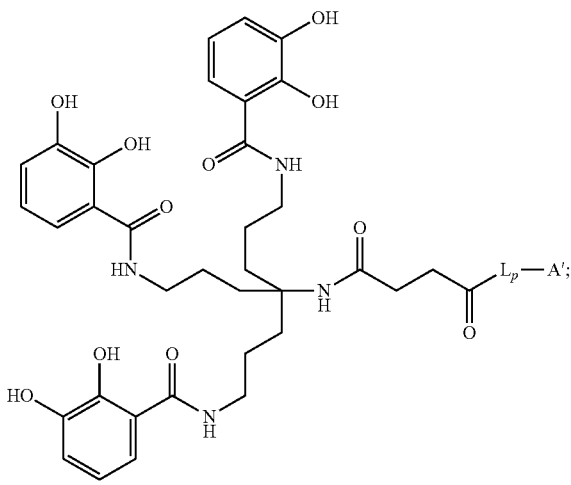

wherein

A' is antibiotic;

each L is independently a linker; and each p is independently 0-11;

Fe(III)-bound form thereof, pharmaceutically acceptable salt thereof, solvate thereof, or combination thereof.

In some embodiments, one or more than one linker is present.

In some embodiments, more than one type of linker is present.

In some embodiments, no linker is present.

One embodiment provides a compound, comprising:

an Fe(III)-binding siderophore;

one or more optional linker covalently bound to the siderophore; and daptomycin covalently bound to the linker, or, if no linker is present, then to the siderophore;

or pharmaceutically acceptable salt or solvate thereof.

Another embodiment provides a compound, comprising:

an Fe(III)-bound siderophore;

one or more optional linker covalently bound to the siderophore; and daptomycin covalently bound to the linker, or, if no linker is present, then to the siderophore;

or pharmaceutically acceptable salt or solvate thereof.

In one embodiment, the siderophore comprises a natural siderophore, semi-synthetic siderophore, synthetic siderophore, or combination thereof.

In one embodiment, the siderophore comprises one or more iron(III)-binding ligand.

In one embodiment, the siderphore comprises one or more iron(III)-binding catechol, hydroxamic acid, beta-hydroxy acid, heteroaromatic ligand, or combination thereof.

In one embodiment, the compound has one of the following formulas:

(Ia)
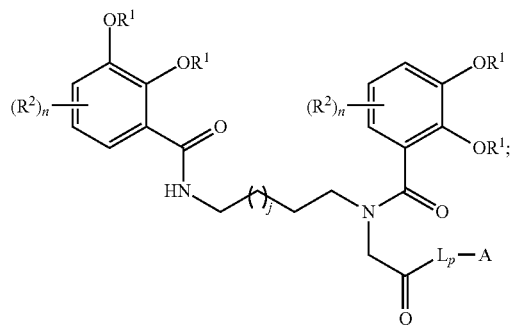

(IIa)
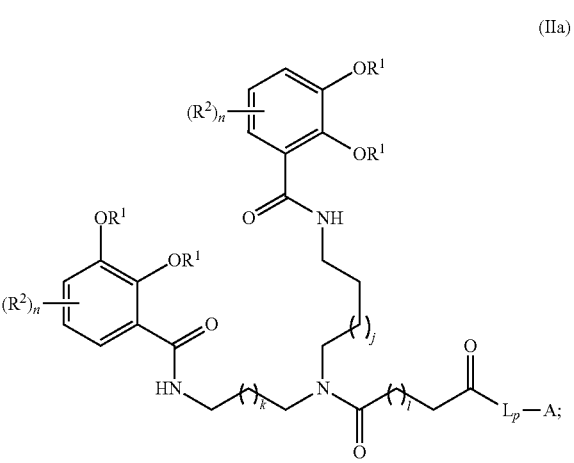

(IIIa)
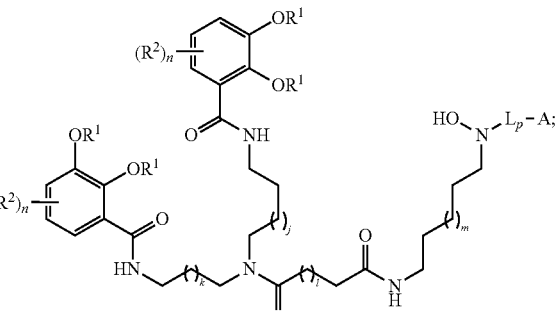

(IVa)
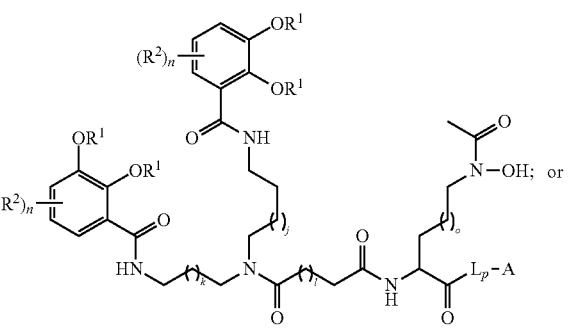

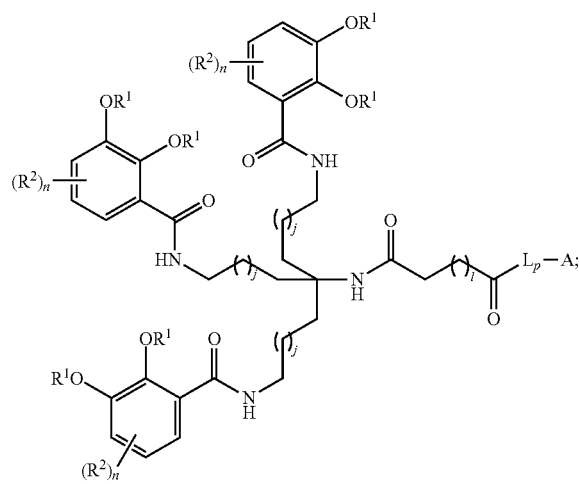
(Va)

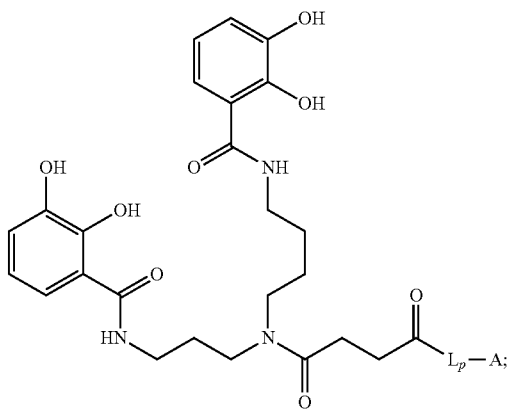
(IIb)

wherein

A is daptomycin;

each L is independently a linker;

each $R^1$ is independently H, —C(=O)alkyl, —C(=O)aryl, or —C(=O)O-alkyl;

each $R^2$ is independently H, alkyl, alkoxy, hydroxy, carboxy, halo, nitro, amino, or cyano;

each n is independently 1, 2, or 3;

each p is independently 0-11;

each j is independently 0-11;

each k is independently 1-11;

each l is independently 1-11;

each o is independently 0-11; and each m is independently 0-11;

Fe(III)-bound form thereof, pharmaceutically acceptable salt thereof, solvate thereof, or combination thereof.

In one embodiment, the compound has one of the following formulas:

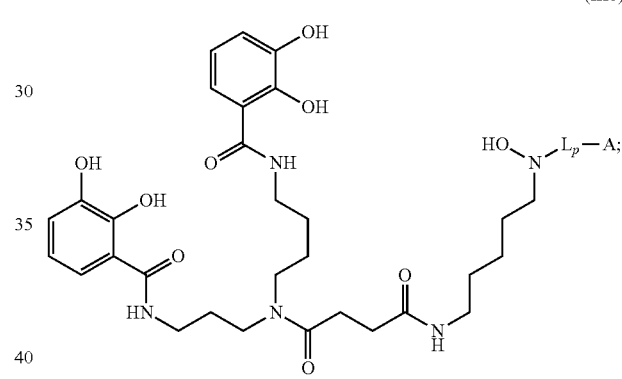
(IIIb)

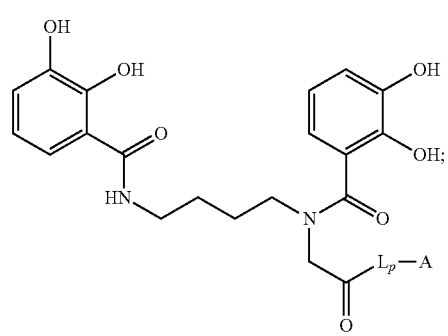
(Ib)

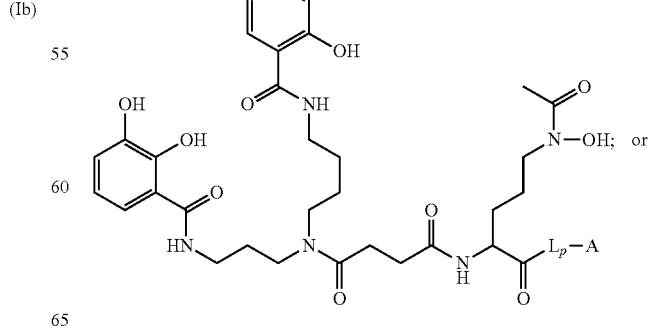
(IVb)

-continued (Vb)

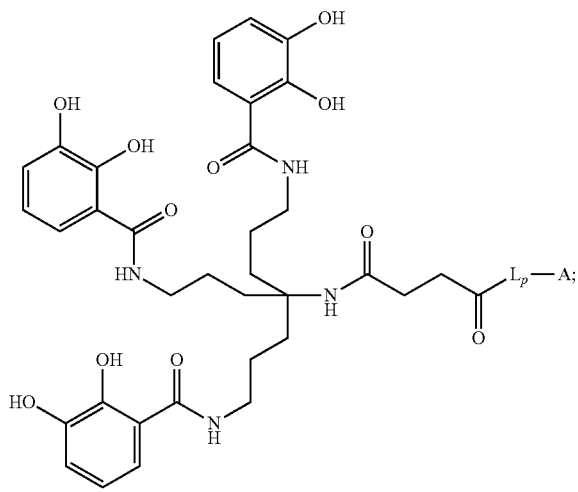

wherein
A is daptomycin;
each L is independently a linker; and
each p is independently 0-11;
Fe(III)-bound form thereof, pharmaceutically acceptable salt thereof, solvate thereof, or combination thereof.

In one embodiment, one or more than one linker is present.

In one embodiment, more than one type of linker is present.

In one embodiment, no linker is present.

One embodiment provides a pharmaceutical composition, comprising the compound or mixture thereof and a pharmaceutically acceptable diluent or carrier.

Another embodiment provides a method for treating a bacterial infection in a subject, comprising administering the compound to a subject.

One embodiment provides a method for treating a bacterial infection in a subject, comprising administering the pharmaceutical composition to a subject.

In one embodiment, the bacterial infection is caused by an antibiotic-resistant bacterium.

In another embodiment, the bacterial infection is caused by a Gram-positive or Gram-negative bacterium.

One embodiment provides a method for killing or inhibiting the growth of a bacterium, comprising contacting the bacterium with the compound.

Another embodiment provides a method for killing or inhibiting the growth of a bacterium, comprising contacting the bacterium with the pharmaceutical composition.

One embodiment provides a pharmaceutical composition, comprising:
an Fe(III)-binding siderophore;
one or more optional linker covalently bound to the siderophore;
antibiotic covalently bound to the linker, or, if no linker is present, then to the siderophore;
or pharmaceutically acceptable salt or solvate thereof; and
a pharmaceutical composition, comprising:
an Fe(III)-bound siderophore;
one or more optional linker covalently bound to the siderophore;
antibiotic covalently bound to the linker, or, if no linker is present, then to the siderophore;
or pharmaceutically acceptable salt or solvate thereof; and
a pharmaceutically acceptable hydrogel.

In one embodiment, the antibiotic is amikacin, aminoglycoside, amoxicillin, amphotericin, ampicillin, ansamycin, azithromycin, aztreonam, bacillomycin, BAL30072, beta-lactam, biapenem, carbacephalosporins, carbapenem, carbomycin, carbomycin A, carumonam, cefaclor, cefalotin, cephalosporin, cethromycin, chloramphenicol, chlortetracycline, ciprofloxacin, clarithromycin, clindamycin, cycloserine, daptomycin, demeclocycline, dirithromycin, doripenem, doxorubicin, doxycycline, ertapeneme, erythromycin, ethambutol, fluoroquinolone, gentamicin, imipenem, isoniazid, josamycin, kanamycin, kitasamycin, lincomycin, linezolid, loracarbef, macrolide, meropenem, methacycline, midecamycin, monobactam, mupirocin, neomycin, nystatin, oleandomycin, oleandomycin, oxazolidinones, oxytetracycline, panipenem, penem, penicillin; peptide antibiotic, polymixin, pyrrolnitrin, quinolone, rifampin, rifamycins, rolitetracycline, roxithromycin, solithromycin, spiramycin, streptomycin, sulfabenzamide, sulfacetamide, sulfadiazine, sulfamerazine, sulfamethazine, sulfamethizole, sulfamethoxazole, sulfisoxazole, sulfonamide, telithromycin, tetracycline, tigimonam, troleandomycin, tylosin, tylocine, vancomycin, or zyvox.

In one embodiment, the first syntheses of conjugates of daptomycin with siderophore analogs are described, which have demonstrated activity against representative Gram-negative bacteria, including Pseusomonas and *Acinetobacter*.

While daptomycin heretofore has been used only for Gram-positive infections and, by itself, is completely inactive against Gram-negative bacteria, siderophore/iron-mediated active transport surprisingly and unexpectedly expands the efficacy of daptomycin to allow treatment of infections caused by pathogenic strains of Gram-negative bacteria.

In one embodiment, the siderophore-linker-antibiotic has one of the following formulas:

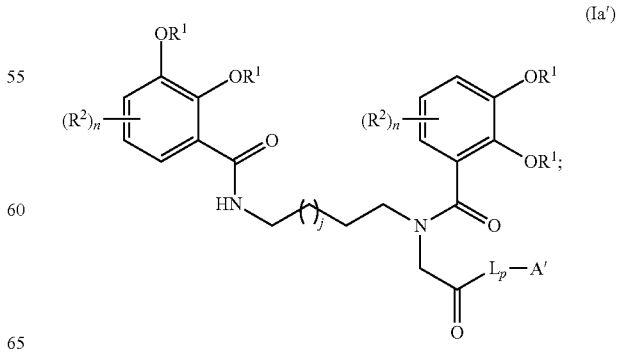

(Ia')

-continued

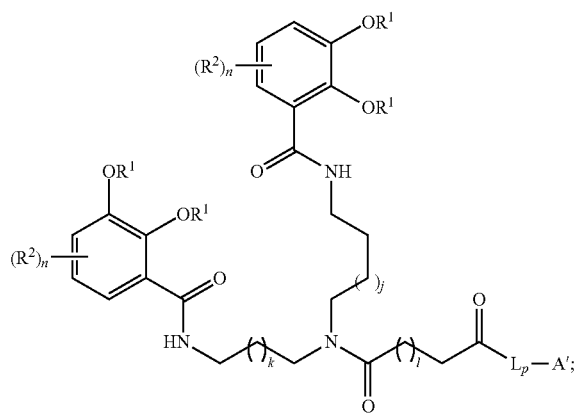
(IIa′)

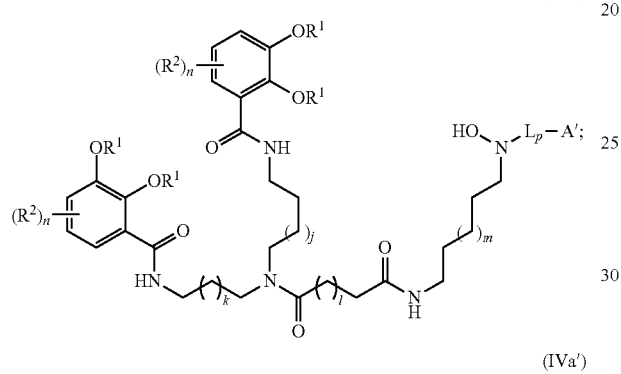
(IIIa′)

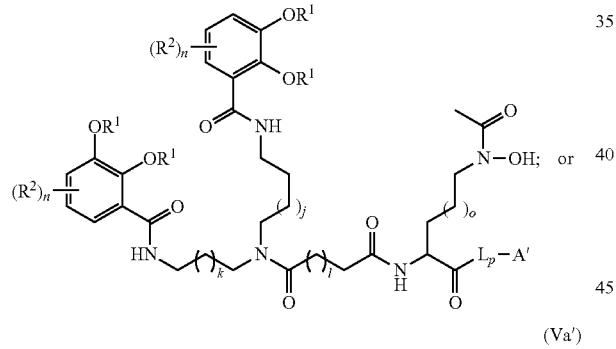
(IVa′)

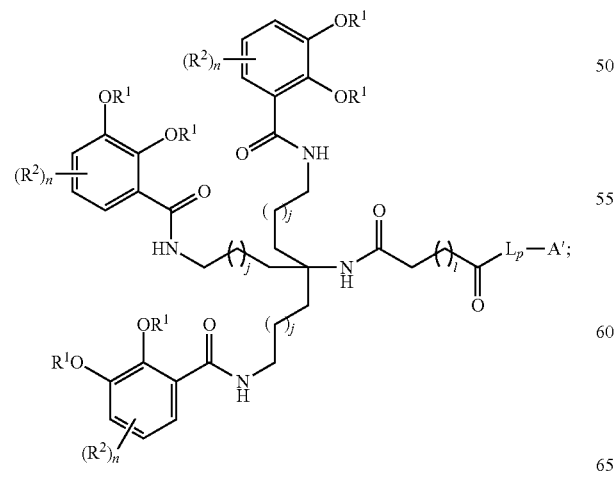
(Va′)

wherein
A′ is antibiotic;
each L is independently a linker;
each $R^1$ is independently H, —C(=O)alkyl, —C(=O)aryl, or —C(=O)O-alkyl;
each $R^2$ is independently H, alkyl, alkoxy, hydroxy, carboxy, halo, nitro, amino, or cyano;
each n is independently 1, 2, or 3;
each p is independently 0-11;
each j is independently 0-11;
each k is independently 1-11;
each l is independently 1-11;
each o is independently 0-11; and
each m is independently 0-11;
Fe(III)-bound form thereof, pharmaceutically acceptable salt thereof, solvate thereof, or combination thereof.

In one embodiment, the siderophore-linker-antibiotic has one of the following formulas:

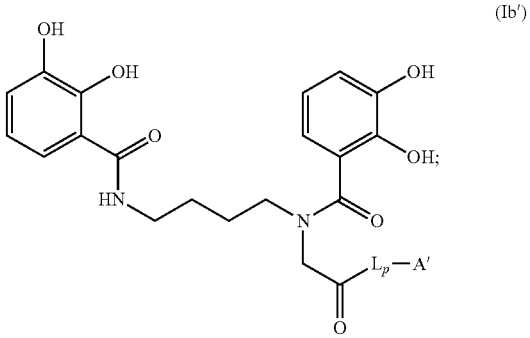
(Ib′)

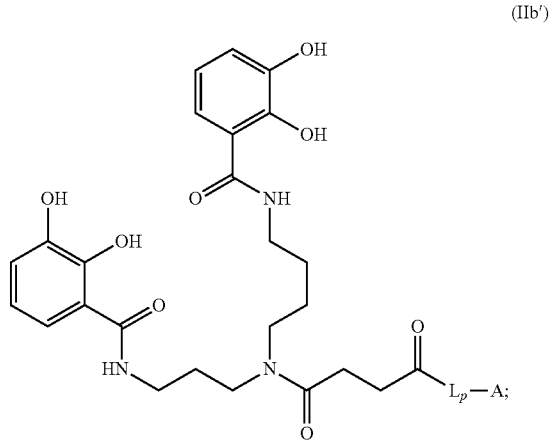
(IIb′)

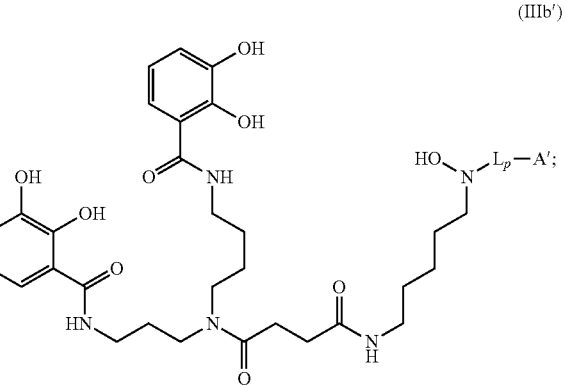
(IIIb′)

-continued

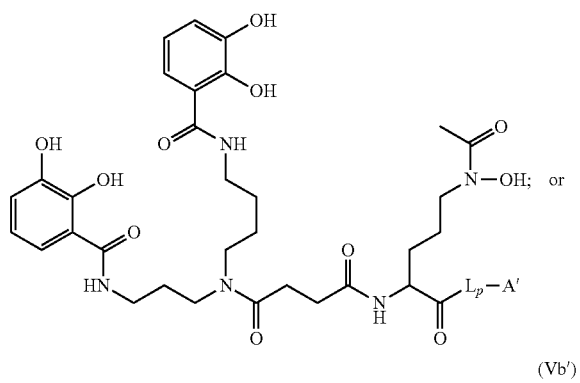

(IVb')

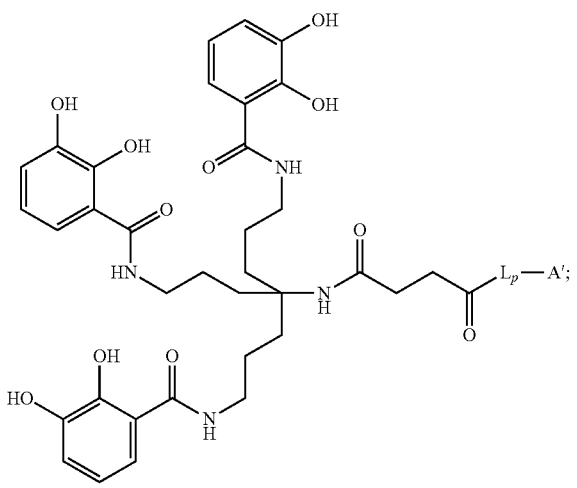

(Vb')

wherein
A' is antibiotic;
each L is independently a linker; and
each p is independently 0-11;
Fe(III)-bound form thereof, pharmaceutically acceptable salt thereof, solvate thereof, or combination thereof.

One embodiment provides a siderophore—linker—daptomycin conjugate in which the siderophore includes one or more bi-dentate, tetra-dentate or hexadentate iron binding groups (catechols, ortho-hydroxy phenyl oxazolines, oxazoles, thiazolines, thiazoles, hydroxamic acids, alpha-hydroxy carboxylic acids or amides, pyridines, hydroxyl pyridones and combinations thereof). In one embodiment, the linker may include direct attachment of the siderophore component to daptomycin either through a carboxylic acid of the siderophore attached to one of the amine components of daptomycin or coupling of one of the carboxylic acid groups of daptomycin to amino or hydroxyl groups of natural siderophores or semi-synthetic derivatives or analogs. Alternatively, the linker may include spacer groups commonly used in bioconjugation chemistry, including PEGylated groups of various lengths. Other attachment methods may suitably include "click chemistry", carbohydrate linkages or other ligation.

In one embodiment, siderophores contain multiple bidentate iron binding ligands, including, for example, but not limited to catechols, hydroxamic acids, beta-hydroxy acids, heteroaromatic ligands, or combinations thereof. In another embodiment, two or three of the bidentate ligands are attached to a core that allows effective stoichiometric iron binding. In another embodiment, the siderophores are based on bis-catechol-containing siderophore analogs or mixed ligand (bis-catechol, monohydroxamate) siderophores with a functionality that can be coupled either directly to daptomycin or allow incorporation of a linker between the siderophore component. In another embodiment, conjugates are formed between daptomycin and either natural siderophores, synthetic siderophores, or semi-synthetic siderophores. The synthetic and semi-synthetic siderophores can be easily prepared using conventional methods or easily derived from modification of natural siderophores. The natural, semi-synthetic, and synthetic siderophores may also be easily bound to an optional linker (bound in-turn to the antibiotic) or, if the linker is omitted, then directly to the antibiotic. In one embodiment, the generalized structures of these new sideromycins (siderophore-optional linker-antibiotic conjugate) may be either the iron-free or iron-bound conjugates. In another embodiment, the sideromycin has the generalized structures siderophore-optional linker-daptomycin or siderophore(Fe(III))-optional linker-daptomycin.

In one embodiment, the siderophore is a natural siderophore, semi-synthetic siderophore, synthetic siderophore, or combination thereof. In one embodiment, the siderophore is a natural siderophore. In one embodiment, the siderophore is a semi-synthetic siderophore. In one embodiment, the siderophore is a synthetic siderophore.

Natural siderophores are known, and are not particularly limiting. Any natural siderophore with pendant functionality (amine, alcohol, carboxylic acid) may be suitably used. Non-limiting examples of natural siderophores include Desferrioxamine A1, Desferrioxamine A2, Desferrioxamine B, Desferrioxamine D1, Desferrioxamine D2, Desferrioxamine E, Desferrioxamine G1, Desferrioxamine G2A, Desferrioxamine G2B, Desferrioxamine G2C, Desferrioxamine H, Desferrioxamine T1, Desferrioxamine T2, Desferrioxamine T3, Desferrioxamine T7, Desferrioxamine T8, Desferrioxamine X1, Desferrioxamine X2, Desferrioxamine X3, Desferrioxamine X4, Desferrioxamine Et1, Desferrioxamine Et2, Desferrioxamine Et3, Desferrioxamine Tel, Desferrioxamine Tet, Desferrioxamine Te3, Desferrioxamine P1, Ferrichrome, Ferrichrome C, Ferricrocin, Sake Colorant A, Ferrichrysin, Ferrichrome A, Ferrirubin, Ferrirhodin, Fimsbactin, Malonichrome, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome Asperchrome F3, Tetraglycine ferrichrome, Des(diserylglycyl)-ferrirhodin, Basidiochrome, Triacetylfusarinine, Fusarinine C, Fusarinine B, Neurosporin, Coprogen, Coprogen B (Desacetylcoprogen), Triornicin (Isoneocoprogen I), Isotriornicin (Neocoprogen I), Neocoprogen II, Dimethylcoprogen, Dimethylneocoprogen I, Dimethyltriornicin, Hydroxycopropen, Hydroxy-neocoprogen I, Hydroxyisoneocoprogen I, Palmitoylcoprogen, Amphibactin B, Amphibactin C, Amphibactin D, Amphibactin E, Amphibactin F, Amphibactin G, Amphibactin H, Amphibactin I, Ferrocin A, Coelichelin, Exochelin MS, Vicibactin, Enterobactin (Enterochelin), Agrobactin, Parabactin, Fluvibactin, Agrobactin A, Parabactin A, Vibriobactin, Vulnibactin, Protochelin, Corynebactin, Bacillibactin, Salmochelin S4, Salmochelin S2, Rhizoferrin, Rhizoferrin analogues, Enantio Rhizoferrin, Staphyloferrin A, Vibrioferrin, Achromobactin, Mycobactin P, Mycobactin A, Mycobactin F, Mycobactin H, Mycobactin M, Mycobactin N, Mycobactin R, Mycobactin S, Mycobactin T, Mycobactin Av, Mycobactin NA (Nocobactin), Mycobactin J, Formobactin, Nocobactin NA, Carboxymycobactin, Ca rboxymycobactin 1, Carboxymycobactin 2, Carboxymycobactin 3, Carboxymycobactin 4, Pyoverdin 6.1 (Pseudobactin), Pyoverdin 6.2, Pyoverdin 6.3 (Pyoverdin Thai), Pyoverdin 6.4 (Pyoverdin 9AW), Pyoverdin 6.5, Pyoverdin 6.6, Isopyoverdin 6.7, (Isopyoverdin BTP1), Pyoverdin 6.8, Pyoverdin 7.1, Pyoverdin 7.2, (Pyoverdin BTP2), Pyoverdin 7.3, (Pyoverdin G+R), Pyoverdin 7.4, (Pyoverdin PVD), Pyoverdin 7.5, (Pyoverdin TH), Pyoverdin 7.6, Pyoverdin 7.7, Pyoverdin 7.8, (Pyoverdin PL8), Pyoverdin 7.9, (Pyoverdin 11370), Pyoverdin, Pyoverdin 7.11, (Pyoverdin 19310), Pyoverdin 7.12, (Pyoverdin 13525), Isopyoverdin 7.13, (Isopyoverdin 90-33), Pyoverdin 7.14, (Pyoverdin R'), Pyoverdin 7.15, Pyoverdin 7.16, (Pyoverdin 96-312), Pyoverdin 7.17, Pyoverdin 7.18, Pyoverdin 7.19, Pyoverdin 8.1, (Pyoverdin A214), Pyoverdin 8.2, (Pyoverdin P19), Pyoverdin 8.3, (Pyoverdin D-TR133), Pyoverdin 8.4, (Pyoverdin 90-51). Pyoverdin 8.5, Pyoverdin 8.6, (Pyoverdin 96-318), Pyoverdin 8.7, (Pyoverdin I-III), Pyoverdin 8.8, (Pyoverdin CHAO), Pyoverdin 8.9, (Pyoverdin E), Pyoverdin 9.1, Pyoverdin 9.2, (Pyoverdin Pau), Pyoverdin 9.3, Pyoverdin 9.4, Pyoverdin 9.5, (Pyoverdin 2392), Pyoverdin 9.6, Pyoverdin 9.7, (Pseudobactin 589A), Pyoverdin (Pyoverdin 2461), Pyoverdin 9.9, Pyoverdin 9.10, (Pyoverdin 95-275), Pyoverdin 9.11, (Pyoverdin C), Pyoverdin 9.12, Pyoverdin 10.1, (Pyoverdin 2798), Pyoverdin 10.2, Pyoverdin 10.3, (Pyoverdin 17400), Pyoverdin 10.4, Pyoverdin 10.5, (Pyoverdin 18-1), Pyoverdin 10.6, (Pyoverdin 1, 2), Isopyoverdin 10.7, (Isopyoverdin 90-44), Pyoverdin 10.8, Pyoverdin 10.9, (Pyoverdin 2192), Pyoverdin 10.10, Pyoverdin 11.1, (Pyoverdin 51W), Pyoverdin 11.2, (pyoverdin 12), Pyoverdin 12.1, (Pyoverdin GM), Pyoverdin 12.2, (Pyoverdin 1547), Azoverdin, Azotobactin 87, Azotobactin D, Heterobactin A, Ornibactin, Ornibactin—C4, Ornibactin—C6, Ornibactin—C8, Aquachelin A, Aquachelin B, Aquachelin C, Aquachelin D, Malleobactin, Marinobactin A, Marinobactin B, Marinobactin C, Marinobactin D1, Marinobactin D2, Marinobactin E, Loihichelin A, Loihichelin B, Loihichelin C, Loihichelin D, Loihichelin E, Loihichelin F, Schizokinen, Aerobactin, Arthrobactin, Rhizobactin 1021, Nannochelin A, Nannochelin B, Nannochelin C, Acineloferrin, Ochrobactin A, Ochrobactin B, Ochrobactin C, Snychobactin A, Snychobactin B, nychobactin C, Mugineic acid, 3-Hydroxymugineic acid, 2'-Deoxymugineic acid, Avenic acid, Distichonic acid, Deoxydistichonic acid, Rhizobactin, Staphyloferrin B, Alterobactin A, Alterobactin B, Pseudoalterobactin A, Pseuoloalterobactin B, Petrobactin, Petrobactin sulphonate, Petrobactin disulphonate, Fusarinine A, Exochelin MN, Ornicorrugatin, Maduraferrin, Alcaligin, Putrebactin, Bisucaberin, Rhodotrulic acid, Dimerum acid, Amycolachrome, Azotochelin, (Azotobactin), Myxochelin, Amonabactin T789, Amonabactin P750, Amonabactin T732, Amonabactin P693, Salmochelin S1, Serratiochelin, Anachelin 1, Anachelin 2, Pistillarin, Anguibactin, Acinetobactin, Yersiniabactin, Micacocidin, Deoxyschizokinen, Heterobactin B, Desferrithiocin, Pyochelin, Thiazostatin, Enantio-Pyochelin, 2,3-Dihydroxybenzoylserine, Salmochelin SX, Citrate, Chrysobactin, Aminochelin, Siderochelin A, Aspergillic acid, Itoic acid, Cepabactin, Pyridoxatin, Quinolobactin, Ferrimycin A, Salmycin A, Albomycin, or combination thereof.

Other natural siderophores may be found in Robert C. Hider and Xiaole Kong Nat. Prod. Rep., 2010, 27.637-657, and the appendices thereof, the entire contents of which are hereby incorporated by reference.

In one embodiment, the siderophore is a semi-synthetic or synthetic siderophore. Non-limiting examples of these siderophores may be found in the table in FIG. 3. In the figure, some siderophores have linkers and/or antibiotics attached, which linkers and/or antibiotics in some embodiments are not to be considered part of the siderophore. In such embodiments, the siderophore—without the linker and/or antibiotic shown in the table—may be suitably used in the compounds described, herein. Obviously, some of the embodied structures show the whole conjugate.

Preferred embodiments include direct conjugation as in MG-1-255 and YML-1-117 and incorporation of extended linkers as in MG-1-288.

Preferred siderophores include bis-catechols as in YML-1-117, tris-catechols as described by Cheng, et al (j. Am. Chem. Soc. 2012, 134, 9898-9901) or derivatives of natural siderophores including entrobactin and derivatives as described by Nolan, et al (J. Am. Chem. Soc., 2012, 134, 18388) and mixed ligand siderophores as in MG-1-255 and natural siderophores including mycobactins as described by Miller et al (J. Am. Chem. Soc. 2011, 133, 2076-2079).

In some embodiments, formulations of sideromycins include those compatible with injection using common vehicles, including those used for daptomycin itself for systemic infections due to Gram-positive and Gram-negative bacteria and formulation in creams and gels, including hydrogels, for treatment of topical infections due to Gram-positive and Gram-negative bacteria.

In one embodiment, the invention provides conjugates of siderophores, optional linkers, and various antibiotics. The conjugates can demonstrate selectively potent anti-bacterial activity, including anti-pseudomonal activity; while the parent antibiotics, themselves, are inactive. In one embodiment, the invention provides iron transport-mediated drug delivery systems comprising the compounds described herein.

In one embodiment, conjugates described herein exhibit significantly enhanced, antibacterial activities against Gram-negative species compared to the parent drugs, especially against *P. aeruginosa*. The conjugates can be assimilated by an induced bacterial iron transport process and their activities may be inversely related to iron concentration, or the conjugates may be administered as the iron(III)-bound complex. The easily synthesized tris-catecholate siderophores can be used to prepare various drug conjugates to target antibiotic-resistant Gram-negative bacteria.

In one embodiment, each $R^1$ is acetyl, propanoyl, or benzoyl. In one embodiment, each $R^1$ is acetyl. In another specific embodiment, each $R^1$ is H.

In one embodiment, each $R^2$ is H, alkyl, alkoxy, or hydroxy. In one specific embodiment, each $R^2$ is H. $R^2$ can also be a substituent as described herein.

In some embodiments, each $R^1$ is the same, while in other embodiments, $R^1$ groups can be different. Likewise, in various embodiments, each $R^2$ can be the same, while in other embodiments, $R^2$ groups can be different from each other, for example, depending on the starting material selected to prepare the compounds.

In one embodiment, the invention further provides methods of treating a, Gram-negative bacterial infection. The methods can include administering to a subject in need thereof an effective therapeutic amount of a compound described herein, thereby treating the bacterial infection. The invention yet further provides methods of killing or inhibiting the growth of a Gram-negative bacterium where the methods include contacting the bacterium with an effective lethal or inhibitory amount of a compound described herein. The bacterial infection can be caused by an antibiotic-resistant bacterium. In some embodiments, the bacterial infection is caused by a Pseudomonal bacterium. In some specific embodiments, the bacterial infection can be caused by *Pseudomonas aeruginosa*, *Escherichia call*, *Acinetobacter baumannii*, or *Salmonella* typhimurium.

The invention also provides a method of increasing the permeability of a Gram-negative bacterium cell membrane to an antibiotic comprising conjugating an antibiotic to the siderophore and/or linker described herein and administering the compound to the bacterium cell membrane, thereby increasing the permeability of the Gram-negative bacterium cell membrane to the antibiotic as a result of its conjugation to the siderophore.

The invention additionally provides novel compounds of the formula described herein, intermediates for the synthesis of the compounds, as well as methods of preparing the compounds. The invention also provides compounds of the formulas described herein that are useful as intermediates for the synthesis of other useful compounds.

As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and, so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more, of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term. "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched, unbranched, saturated or unsaturated, linear or cyclic hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, cyclopropyl, cyclobutyl, cyclopentyl, cyclohexyl, cycloheptyl, and the like. The alkyl can be unsubstituted or optionally substituted, for example, with a substituent described herein. The alkyl can also be optionally partially or fully unsaturated. As such, the recitation of an alkyl group can optionally include both alkenyl or alkynyl groups, linear or cyclic, in certain embodiments. The alkyl can be a monovalent hydrocarbon radical, as described herein, or it can be a divalent hydrocarbon radical (i.e., an alkylene), depending on the context of its use. In one embodiment, one or more carbons in the alkyl group may be replaced with one or more heteroatoms, e.g., O, N, S, P, combination thereof, and the like.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups. In one embodiment, one or more carbons in the aryl group may be replaced with one or more heteroatoms, e.g., O, N, S, P, combination thereof, and the like.

The term "amino acid" refers to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, divalent radicals thereof, salts thereof, or combination thereof.

The term "carboxy" group refers to a univalent —CR"(=O) radical or a —CR"(=O)-containing substituent group. In one embodiment, the carboxy group suitably includes carboxylic acids, aldehydes, ketones, and combinations thereof. The R" group is suitably chosen from any of the substituent groups. In one embodiment, the carboxy group may be attached to the parent structure through one or more independent divalent intervening substituent groups.

The term "amino" group refers to a univalent —NR"R" radical or an —NR"R"-containing substituent group. The R" groups may be the same or different and, are suitably and independently chosen from any of the substituent groups. In one embodiment, the amino group may be attached to the parent structure through one or more independent divalent intervening substituent groups.

The term "nitro" group refers to a univalent —NO$_2$ radical or an —NO$_2$-containing substituent group. In one embodiment, the amino group may be attached to the parent structure through one or more independent divalent intervening substituent groups.

The term "cyano" group refers to a univalent —CN radical or a —CN-containing substituent group. In one embodiment the cyano group may be attached to the parent structure through one or more independent divalent intervening substituent groups.

The term "peptide" refers to polypeptide, protein, oligopeptide, monopeptide, dipeptide, tripeptide, tetrapeptide; pentapeptide, hexapeptide, heptapentide, octapeptide, nonapeptide, decapeptide, undecapeptide, divalent radicals thereof, salts thereof, or combination thereof. In some embodiments, the term peptide may refer to a peptide bond, amide bond, or the like. For example, a peptide or amide bond is a covalent chemical bond formed between two molecules when the carboxyl group of one molecule reacts with the amino group of the other molecule forming a —C(O)NH— bond or peptide link.

A "linker" or "linking group" refers to an organic or inorganic chain or moiety that connects the siderophore to the antibiotic. The linker may be a molecule having end groups respectively tailored to covalently bond with the siderophore and the antibiotic. In one embodiment, the linker may be covalently attached to the siderophore and antibiotic by an ester or amide bond. Nonlimiting examples of linkers include a group L where L is or is derived from one or more optionally substituted amino acid, peptide, alkylene, alkenylene, arylene, polyethylene glycol, polypropylene glycol, or combination thereof. Other nonlimiting examples of linkers include a group L where L is or is derived from a divalent radical of the formula —(W)$_a$—(Z)$_b$—(W)$_c$—; wherein a, b, and c are each independently 0-11; wherein each W is independently —N(R')C(=O)—, —C(=O)N(R')—, —OC(=O)—, —C(=O)O—, —O—, —S—, —S(O)—, —S(O)$_2$—, —N(W)—, —C(=O)—, —(CR'$_2$)$_x$—, —(CX$_2$)$_y$—, —(CR'$_2$)$_n$—(CX$_2$)$_y$—, —(CR'$_2$CR'$_2$O)$_x$—, —(OCR'$_2$CR'$_2$)$_x$—, —N$^+$(R')$_2$(CR'$_2$)$_y$—, (C$_1$-C$_{12}$)alkylene, (C$_2$-C$_{12}$)alkenylene, (C$_2$-C$_{12}$) alkynylene, combination thereof, or a direct bond; and Z is a divalent moiety selected from $(C_1-C_{12})$alkylene, $(C_2-C_{12})$alkenylene, $(C_2-C_{12})$alkynylene, $(C_3-C_5)$cycloalkylene, $(C_6-C_{10})$arylene, —N(R')C(=O)—, —C(=O)N(R')—, —OC(=O)—, —C(=O)O—, —N(R')—, —C(=O)—, —(CY$_2$)—, —(CR'$_2$)$_x$—(CY$_2$)$_y$—, —(OCR'$_2$—CR'$_2$)$_x$—, —(CR'$_2$CR'$_2$O)$_x$—, —C(O)NR' (CR'$_2$)$_y$—, —OP(O)(OR)O—, —OP(O)(OR')O(CR'$_2$)$_y$—, —OP(O)(OR')OCR'$_2$CR'(OR')CR'$_2$—, —N$^+$(R')$_2$(CR'$_2$)$_x$—, or $(C_1-C_{12})$alkylene, $(C_2-C_{12})$alkenylene, or $(C_2-C_{12})$alkynylene, optionally interrupted between two carbons, or between a carbon and an oxygen, with a $(C_3-C_8)$cycloalkyl, heteroaryl, heterocycle, or $(C_6-C_{10})$aryl group, divalent amino acid, divalent peptide, combination thereof, or Z is a direct bond; wherein x and y are each independently 0-11; wherein each X is independently a halogen ("halo"): F, Cl, Br, or I; and each R' is independently H, alkyl, aryl, (aryl)alkyl (e.g., benzyl), heteroaryl, (heteroaryl)alkyl, heterocycle, heterocycle(alkyl), or a protecting group; wherein each of W, Z and R' may be optionally substituted with one or more substituent groups; and each of W, Z, and R' may have one or more carbons replaced with one or more heteroatoms, e.g., N, O, S, P, and the like.

In one embodiment, one or more of the W and/or Z groups can form or originate from a part of the siderophore and/or linker The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent".

The substituent can be one of a selection of the indicated group(s), or it can be a suitable group known to those of skill in the art, provided that the substituted atom's normal valency is not exceeded, and that the substitution results in a stable compound. Nonlimiting examples of substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure, and combinations thereof. Other nonlimiting examples of the substituent group include, e.g., —X, —R", —O—, —OR", —SR, —S—, —NR"$_2$, —NR"$_3$+, =NR", —CX$_3$, —CN, —OCN, —SCN, —N=C=O, —NCS, NO, —NO$_2$, =N$_2$, —N$_3$, —NC(=O)R", —C(=O)R", —C(=O)NR"R", —S(=O)$_2$O—, —S(=O)$_2$OH, —S(=O)$_2$R", —OS(=O)$_2$OR", —S(=O)$_2$NHR", —S(=O)R", —OP(=O)(OR")$_2$, —P(=O)(OR")$_2$, —OP(=O)(OH)(OR"), —P(=O)(OH)(OR"), —P(=O)(O$^-$)$_2$, —P(=O)(OH)$_2$, —C(=O)R", —C(=O)X, —C(S)R", —C(O)OR", —C(O)O$^-$, —C(S)OR", —C(O)SR", —C(S)SR", —C(O)NR"R", —C(=S)NR"R", —C(=NR")NR"R", wherein each X is independently a halogen ("halo"): F, Cl, Br, or I; and each R" is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

An antibiotic is an agent that inhibits bacterial or fungal growth or kills bacteria or fungi. Antibiotics can be linked to the linker and/or the siderophore. Accordingly, any antibiotic that has an available functional group, e.g., hydroxyl or amino group, can be used. Nonlimiting examples of antibiotics that may be useful include but are not limited to those found in http://en.wikipedia.org/wiki/Antibacterial. Other examples include lincomycins, beta-lactams, macrolides, ketolides, tetracyclines, sulfur-based antibiotics, oxazolidinones, peptide antibiotics, quinolones, fluoroquinolones, and rifamycins. Other nonlimiting examples of suitable antibiotics include amikacin, aminoglycoside, amoxicillin, amphotericin, ampicillin, ansamycin, azithromycin, aztreonam, bacillomycin, BAL30072, beta-lactam, biapenem, carbacephalosporins, carbapenem, carbomycin, carbomycin A, carumonam, cefaclor, cefalotin, cephalosporin, cethromycin, chloramphenicol, chlortetracycline, ciprofloxacin, clarithromycin, clindamycin, colistin, cycloserine, daptomycin, demeclocycline, dirithromycin, doripenem, doxorubicin, doxycycline, ertapeneme, erythromycin, ethambutol, fluoroquinolone, gentamicin, imipenem, isoniazid, josamycin, kanamycin, kitasamycin, lincomycin, linezolid, loracarbef, macrolide, meropenem, methacycline, midecamycin, monobactam, mupirocin, neomycin, nystatin, oleandomycin, oleandomycin, oxazolidinones, oxytetracycline, panipenem, penem, penicillin, peptide antibiotic, polymixin, polymyxin B, pyrrolnitrin, quinolone, rifampin, rifamycins, rolitetracycline, roxithromycin, solithromycin, spiramycin, streptomycin, sulfabenzamide, sulfacetamide, sulfadiazine, sulfadoxine; sulfamerazine, sulfamethazine, sulfamethizole, sulfamethoxazole, sulfisoxazole, sulfonamide, telithromycin, tetracycline, tigecycline, tigimonam, troleandomycin, tylosin, tylocine, vancomycin, or zyvox.

The compounds described herein can be prepared according to the methods in the Examples below, or may be prepared according to known techniques in the art of organic synthesis. Many linking groups for conjugating antibiotics to the siderophore and/or linker are commercially available, and/or can be prepared as described in the art. Information regarding general synthetic methods that may be used to prepare the compounds described herein, particularly with respect employing linking groups, may be found in Greg T. Hermanson, Bioconjugate Techniques, Academic Press, San Diego, Calif. (1996). Useful linkers and conjugation techniques that can be used to link antibiotics to Formula (A) are further described by Roosenberg et al., Curr. Med. Chem. 2000, 7, 159; Wittmann et al., Bioorg. Med Chem. 2002, 10, 1659; and Heinisch et al., J. Med. Chem. 2002, 45, 3032. Additional useful reactions well known to those of skill in the art are referenced in March's Advanced. Organic Chemistry Reactions, Mechanisms, and Structure, 5th Ed. by Michael B. Smith and Jerry March, John Wiley & Sons, Publishers; and Wuts a al. (1999), Protective Groups in Organic Synthesis, $3^{rd}$ Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be, appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% by weight of active compound, e.g., the conjugate and/or antibiotic as appropriate. The percentage of the compositions and preparations, can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like, A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in water, DMSO, methanol, ethanol, saline, glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can, include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, methanol, DMSO, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it may be desirable to administer the active agent to the skin as a composition or formulation, for example, in combination with a dermatologically acceptable carrier, which may be a solid, a liquid, a gel, hydrogel (e.g., keratin hydrogel), mixtures thereof, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Other examples of dermatological compositions for delivering active agents to the skin are known to the art; for example, see U.S. Pat. No. 4,992,478 (Geria), 4,820,508 (Wortzman), 4,608,392 (Jacquet-et al.), and 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 1 ng/ml to 5 g/ml, which may include 1, 2, 3, 4, 5, 6, 7, 8, 9, 10, 50, 100, 500 ng, 1, 2, 3, 4, 5, 6, 7, 8, 9, 10, 50, 100, 500n, 1, 2, 3, 4, 5, 6, 7, 8, 9, 10, 50, 100, 500 mg, 1, 2, 3, 4, 5, 6, 7, 8, 9, 10, 50, 100, 500 cg, 1, 2, 3, 4, 5, 6, 7, 8, 9, 10, 50, 100, 500 dg, 1, 2, 3, 4, and 5 g/ml or any combination thereof as appropriate.

Alternatively, the compound may be conveniently administered in a unit dosage form, foe example, containing 5 to 1000 mg/m$^2$, conveniently 10 to 750 mg/m$^2$, most conveniently, 50 to 500 mg/m$^2$ of active ingredient per unit dosage form.

Alternatively, the unit dosage may range from 0.1 mg/kg to 1000 mg/kg, which may include 0.1, 0.5, 1, 2, 3, 4, 5, 10, 20, 50, 75, 100, 200, 250, 300, 350, 400, 500, 700, and 1000 mg/kg, or any combination thereof.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like. The infection Can be a bacterial infection, for example, one caused by a bacterium described herein.

The ability of a compound of the invention to treat a bacterial infection may be determined by using assays well known to the art. For example, the design of treatment protocols, toxicity evaluation, data analysis, quantification of cell kill, and the biological significance of the use of antibacterial screens are known. In addition, ability of a compound to treat a bacterial infection or kill or inhibit bacteria may be determined using the assays as described herein.

EXAMPLES

Syntheses of mixed ligand-daptomycin. Conjugates with a glutaryl linker (MG-1-255) and Glutaryl-PEG linker (MG-1-288).

Two conjugates were synthesized. The first (11, MG-1-255) consisted of a direct linkage by formation of an amide bond between the terminal carboxylic acid of the siderophore 9 and natural pendant primary amine of daptomycin. The second (15, MG-1-286) incorporated an extended PEG linker.

Example 1. Mixed ligand Daptomycin conjugate 11 (MG-1-255) was obtained as a white fluffy solid (40 mg) by a two-step sequence, 1) coupling of mixed anhydride of 9a with daptomycin, and 2) hydrogenolytic deprotecton and reverse phase chromatography. The $Fe^{3+}$ complex 12 (MG-1-275) was also prepared by treatment of 11 with ferric acac to give the dark blue iron complex 12.

Scheme 1. Syntheses of mixed ligand daptomycin conjugate MG-1-255 and the iron complex MG-1-275.

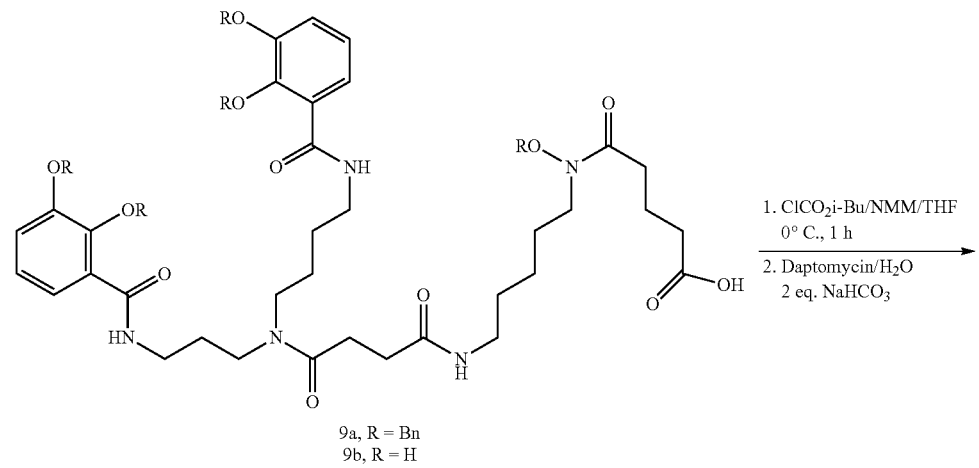

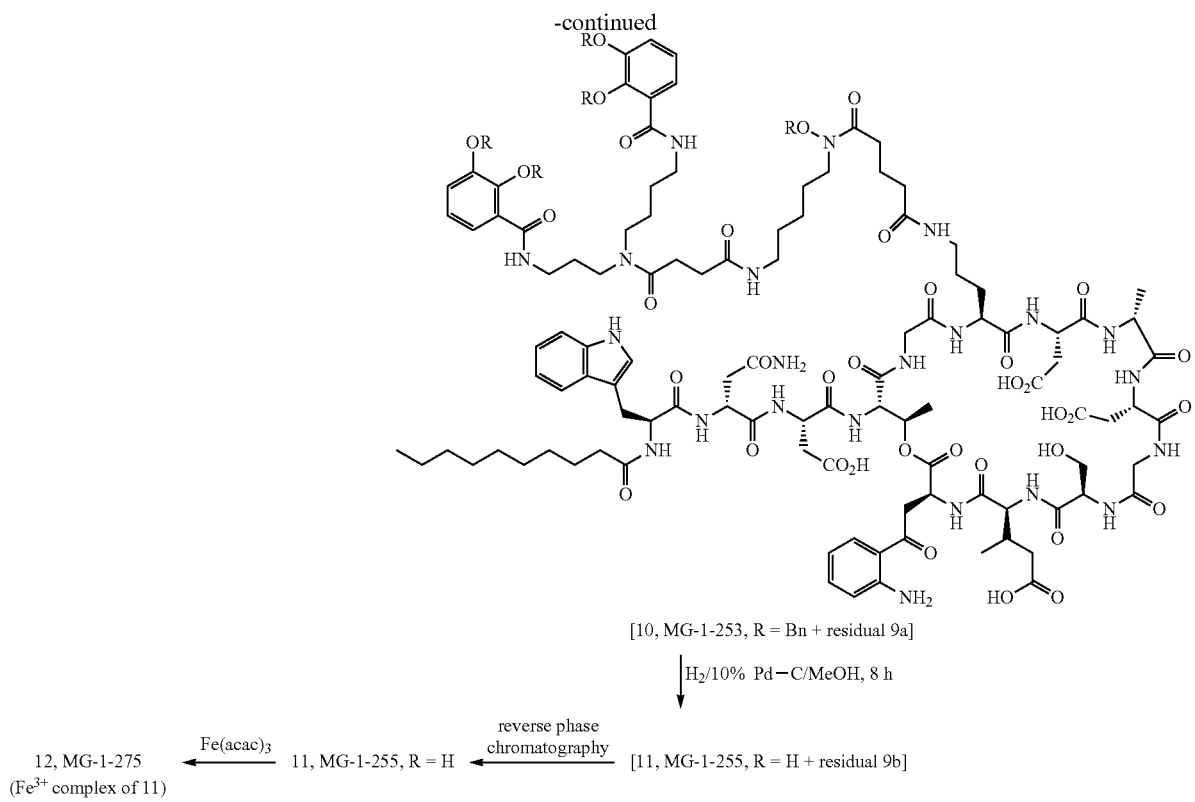

[10, MG-1-253, R = Bn + residual 9a]

H₂/10% Pd—C/MeOH, 8 h

12, MG-1-275 ←—Fe(acac)₃— 11, MG-1-255, R = H ←—reverse phase chromatography— [11, MG-1-255, R = H + residual 9b]
(Fe³⁺ complex of 11)

Zones of growth inhibitions were determined on conjugate 11 (MG-1-255). *Pseudomonas aeruginosa*: Pa KW799/Wt zones of inhibition (15/19 p); Pa KW799/61 zones of growth inhibition in mm (22/28 p). *Acinetobacter* baumanni ATCC 17961: Zones of growth inhibition in mm (17/22 P). No difference in activity was noted with either the iron free or iron bound form.

Example 2. The synthesis of the conjugate 16 (MG-1-288) is shown below. Thus, the benzyl-protected, glutaryl siderophore 9a was synthesized according to the literature used for the corresponding succinate analog (j. Med. Chem. 2013, 56, 4044-4052). After chloformate activation (ClCO₂i-Bu, NMM, THF, 0° C., 1 h) the intermediate active, ester was reacted with amino-carboxyl PEG 13 after in-situ silylation of the carboxyl terminal (PEG, BSA, CH₃CN) to obtain the fully protected, PEG-linked siderophore component 14 (MG-1-282), Further activation of the carboxyl terminal of the siderophore 14 under the same conditions (ClCO₂i-Bu, NMM, THF, 0° C., 1 h), followed by treatment with the free amine-containing Daptomycin provided the fully protected conjugate 15a (MG-1-283), which was subjected to hydrogenolysis (H₂, 10% Pd—C, MeOH, 6 h) to obtain the PEG-containing conjugate 15b (MG-1-286), and some deprotected siderophore 14. The crude conjugate 15b (MG-1-286) was purified by reverse phase chromatography and lyophilized to provide 16 (MG-1-288) as a pure white, fluffy solid (50 mg) that was subjected to biological screening.

Scheme 2. Synthesis of mixed ligand-PEG-linked-daptomycin conjugate MG-1-288.

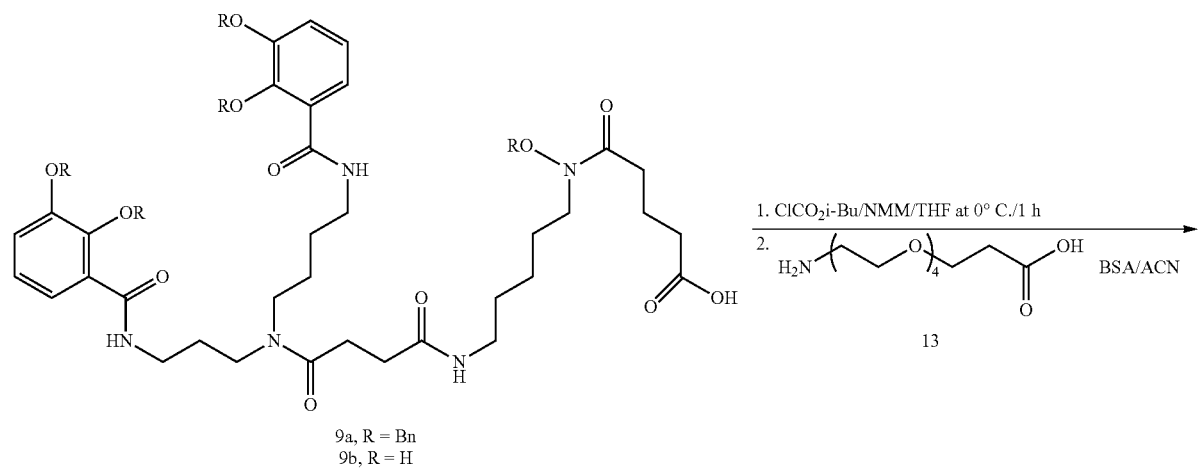

9a, R = Bn
9b, R = H

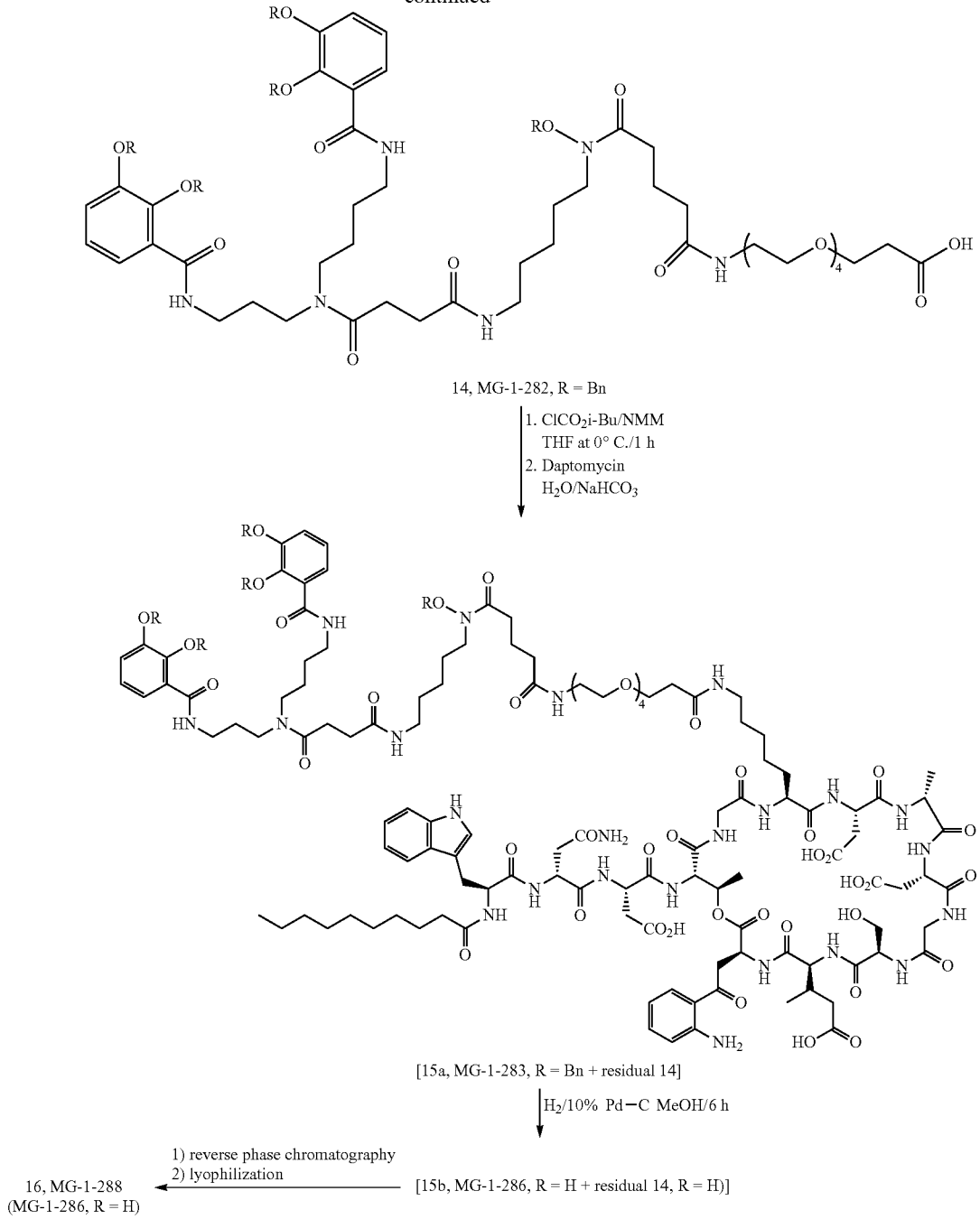

Synthesis of MG-1-255 and MG-1-275:

To a solution of compound 9a (100 mg, 0.079 mmol) in THF (9.6 mL) at 0° C. was added NMM (10 μL, 0.094 mmol) followed by ClCO$_2$i-Bu (12 μL, 0.094 mmol), and the solution was stirred for 1 h at 0° C. The resulting mixed anhydride was filtered into a solution of Daptomycin (128 mg, 0.079 mmol) and NaHCO$_3$ (13 mg, 0.158 mmol) in H$_2$O (2.4 mL). The reaction mixture was stirred in the resulting mixed solvent system (THF/H$_2$O, 4:1, 12 mL) at 0° C. (1 h) and then at room temperature (overnight) under argon atmosphere. Next day, the reaction mixture, was adjusted to pH 3 using 1N HCl, concentrated to remove THF, and lyophilized to provide the benzyl-protected mixed ligand Daptomycin conjugate 10 (MG-1-253); LCMS Calcd for C$_{142}$H$_{178}$N$_{22}$O$_{37}$ 2783.27, found 1393.1271 (MH$^+$/2), Rt 16.0 min; along with some unreacted starting siderophore 9a; LCMS Calcd for C$_{70}$H$_{79}$N$_5$O$_{12}$: 1181.57, found 1181.57, Rt 15.8 min (Scheme 1).

A solution of the above mixture (10, MG-1-253) in MeOH (10 mL) was charged with 10% Pd—C(50 mg). The resulting suspension was subjected to hydrogenolysis at room temperature under 1 atm of hydrogen for 8 h. The reaction mixture was filtered and concentrated and the residue was purified by reverse phase column chromatography using a CH$_3$CN/H$_2$O gradient to obtain fractions (50% Water in CH$_3$CN) containing the mixed ligand Daptomycin conjugate 11 (MG-1-255) as a white fluffy solid (40 mg); LCMS Calcd for $C_{107}H_{148}N_{22}O_{37}$ : 2333.04, found 2334.037 (MH+), Rt 12.4 min.

A portion of 10 (MG-1-255, 10 mg) was treated with a Fe(acac)$_3$ solution to obtain the corresponding dark blue $Fe^{3+}$ complex MG-1-275; LCMS Calcd for $C_{107}H_{148}N_{22}O_{37}$ : 2333.04, found 1194.4904 (MFe$^{3+}$/2), Rt 10.8 min, and 1168.0379 (MH+/2), Rt 11.1 min.

Synthesis of MG-1-288;

To a solution of compound 9a (200 mg, 0.158 mmol) in THF (10 mL) at 0° C. was added NMM (20 μL, 0.188 mmol) followed by ClCO$_2$i-Bu (24 μL, 0.188 mmol), and the solution was stirred for 1 h at 0° C. to form the mixed anhydride. In a separate flask, a solution of PEG 13 (50 mg, 0.188 mmol) in CH$_3$CN (5 mL) and BSA (1 mL) was stirred at room temperature for 1 h. The resulting silylated PEG was then treated with the filtered solution of the above mixed anhydride and stirred overnight at room temperature. Next day, the reaction mixture was diluted with water (10 mL), adjusted to pH 3 with 1N HCl and extracted with EtOAc (5×3 mL) to obtain the PEG-modified protected siderophore 14 (MG-1-282, 284 mg); LCMS Calcd for $C_{81}H_{100}N_6O_{17}$ 1428.71, found 1429.72 (MH+), Rt 14.8 min.; $^1$H NMR (600 MHz, CD3OD) d To a solution of compound 14 (MG-1-282, 284 mg, 0.198 mmol) in THF (12 mL) at 0° C. was added NMM (20 μL, 0.198 mmol) followed by ClCO$_2$i-Bu (24 μL, 0.198 mmol), and the solution was stirred for 1 h at 0° C. The resulting mixed anhydride was filtered into a solution of Daptomycin (320 mg, 0.198 mmol) and NaHCO$_3$ (30 mg, 0.396 mmol) in H$_2$O (3 mL). The reaction mixture in the mixed solvent system, THF/H$_2$O (4:1.15 mL), was stirred at 0° C. (1 h) and then at room temperature (overnight) under argon atmosphere. Next day, the reaction mixture was adjusted to pH 2.5 using 1N HCl, and concentrated to remove THF. An attempt to dissolve the residue in EtOAc and water resulted in the precipitation of the protected conjugate 15a (MG-1-283) as a gummy solid that was soluble in MeOH (285 mg, 48%); LCMS Calcd for $C_{153}H_{199}N_{23}O_{42}$ 3030.41, found 1516.7032 (MH$^+$/2), Rt 15.2 min; along with some unreacted starting siderophore 14 (MG-1-282).

A solution of the conjugate 15a (MG-1-283) in MeOH (10 mL) was charged with 10% Pd—C(30 mg). The resulting suspension was subjected to hydrogenolysis at room temperature under 1 atm of hydrogen for 6 h. The reaction mixture was filtered and concentrated to obtain 120 mg of the crude conjugate. The crude residue was purified by reverse phase column chromatography using a CH$_3$CN/H$_2$O gradient to obtain a fraction containing the mixed ligand Daptomycin conjugate MG-1-288 as a white fluffy solid (50 mg); LCMS Calcd for $C_{118}H_{169}N_{23}O_{42}$: 2580.18, found 2581.16 (MH+) 1291.59 (MH$^4$/2), Rt 12.4 min. (Peak 2), along with some unprotected siderophore 14 (R=H); LCMS Calcd for $C_{46}H_{70}N_6O_{17}$: 978.48, found 979.48 (MH+), Rt 9.4 min. (peak 1).

MG-1-288 also showed activity against strains of Pseudomonus and *Acinetobacter* that was similar to that of MG-1-255 (FIG. 4).

Example 3. Synthesis of a bis-catechol daptomycin conjugate. Synthetic Procedure for the daptomycin conjugate YML-I-117.

Scheme 3. Synthesis of bis-catechol daptomycin conjugate YML-1-117.

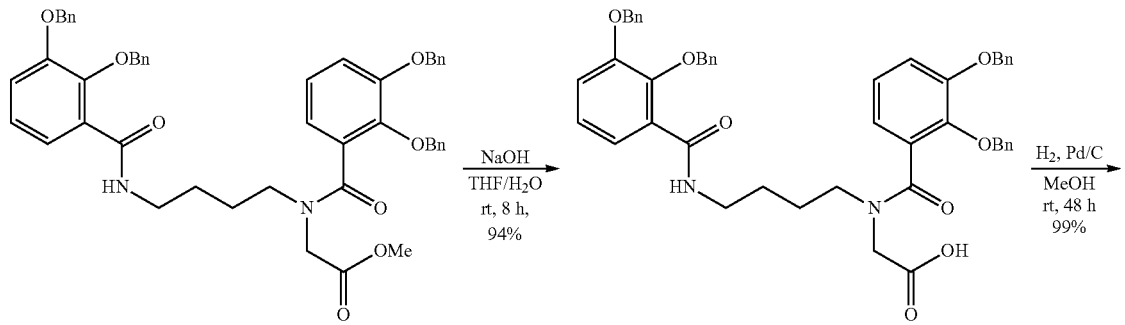

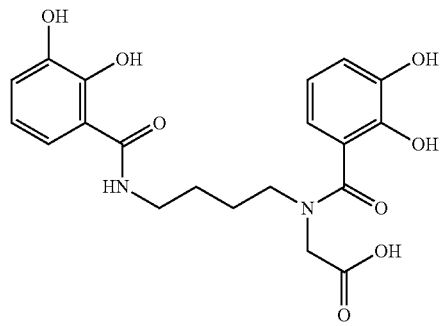

A

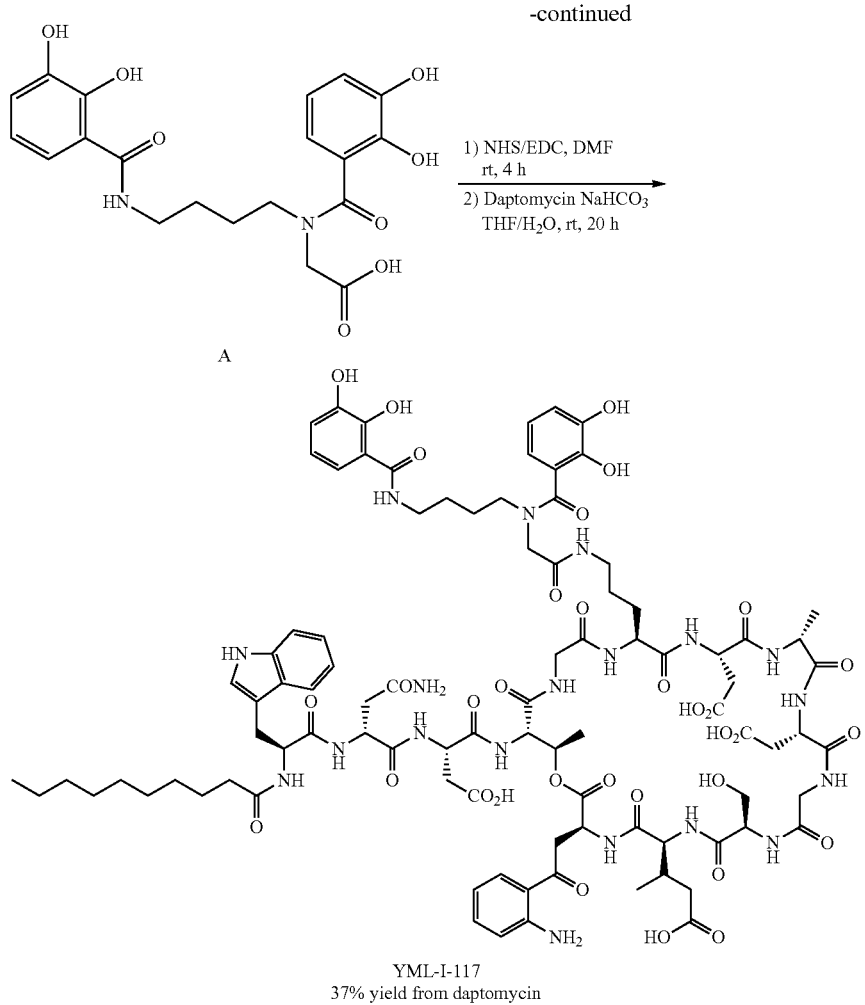

YML-I-117
37% yield from daptomycin

Synthesis of carboxylic acid A:

To a solution of commercially available methyl ester (PracticaChem, 21.0 g, 26.5 mmol) in THF (200 mL) at room temperature, was added sodium hydroxide (1.48 g, 37.0 mmol) and water (100 mL). The reaction was stirred at room temperature for 8 h, and the volatiles were evaporated under reduced pressure. The residue was participated between water and ethyl acetate. The aqueous phase was separated, acidified with 1N HCl and extracted with ethyl acetate. The ethyl acetate extracts were washed with brine, dried ($Na_2SO_4$), filtered and concentrated to give 19.5 g (94%) of the benzyl protected acid.

$^1$H NMR (500 MHz, $CDCl_3$) ▯ 7.91-7.77 (m, br, 1H), 7.40-6.78 (m, 26H), 5.08-4.84 (m, 8H), 4.20 and 3.90 (m, 1H), 3.84, 3.70, and 3.58 (m, 1H), 3.10-2.94 (m, 4H), 1.38-0.98 (m, 4H).

A solution of the benzyl protected acid (6.0 g, 7.70 mmol) in methanol (400 mL) was hydrogenated with hydrogen gas (1 atm) in the presence of Pd/C (10% wt, 1.6 g) at room temperature for 48 h. The catalyst was filtered off and rinsed with methanol. The filtrates were concentrated to give 3.2 g (99%) of the desired carboxylic acid A.

$^1$H NMR (500 MHz, $CD_3OD$) ▯ 7.20, 6.91, and 6.81 (m, 3H), 6.70-6.62 (m, 3H), 4.24 and 4.04 (m, br, 2H), 3.62, 3.44, 3.36, and 3.22 (m, br, 411), 1.74-1.42 (m, br, 4H).

Synthesis of YML-I-117:

To a solution of acid A (500 mg, 1.20 mmol) and NHS (180 mg, 1.56 mmol) in DMF (6 mL) at room temperature, was added EDC·HCl (300 mg, 1.56 mmol). The reaction was stirred at room temperature for 4 h. The resulting NHS active ester solution was used in the subsequent coupling reaction. To a solution of daptomycin. (300 mg, 0.185 mmol) and sodium bicarbonate (78 mg, 0.928 mmol) in tetrahydrofuran (3 mL) and water (3 mL) at room temperature, was added the freshly prepared NHS active ester. The resulting reaction was stirred at room temperature for 20 h. The volatiles were evaporated under reduced pressure. The residue was acidified and separated from a column to give the desired daptomycin conjugate YML-1-117 (140 mg, 37% yield from daptomycin). The structure of YML-I-117 is confirmed by $^1$H NMR spectrum and LC-MS data (not shown).

To improve solubility, YML-1-117, was treated with aqueous sodium bicarbonate to produce YML-1-119, in which all of the carboxylic acid groups of the daptomycin component were converted to the corresponding sodium salts. Treatment of YML-1-117 with ferric acac gave the corresponding iron complex.

Determination of Gram-negative antibiotic activity of daptomycin sideromycins.

Antibiotic activity was determined using agar diffusion assays against representative Gram-negative bacteria, including *Pseudomonas aeruginosa* (Pa6), and several multidrug resistant forms of *Acinetobacter baumannii*. Representative results are shown in Table 1 and a corresponding picture of an actual petri dish showing the agar diffusion results (FIG. 4). The results clearly indicate that siderophore conjugates of daptomycin are active against multi-drug resistant Gram-negative bacteria, while daptomycin and the gold standard, ciprofloxacin, are completely inactive. These results verify the hypothesis that the siderophores facilitate active transport of antibiotics into Gram-negative bacteria and thus extend the spectrum of activity of the antibiotic component.

inoculation with $10^8$ *Acinetobacter baumannii* ATCC 17961; Treatment administered IV at 30 min and 24 hr post inoculation; Treatments—Ciprofloxacin 50 mg/kg, HT-10 100 mg/kg, HT-10 50 mg/kg, HT-10 25 mg/kg, HT-10 10 mg/kg, HT-10 5 mg/kg, daptomycin 50 mg/kg, Vehicle.

Example 4 (Sections 1-7):

In this example, the design, synthesis, and studies of novel siderophore-antibiotic conjugates (new sideromycins) and their effects of sideromycins released from a keratin hydrogel on the drug resistant strains of *S. aureus* (MRSA), *A. baumannii* and *P. aeruginosa* are described.

TABLE 1

Spectrum of antimicrobial activity of daptomycin-sideromycins in agar diffusion assays.

| | | | | | Zone of Growth Inhibition (mm) | | | |
| | | | | | | A. baumannii | | |
| Well | Compound | Conc. | Solvent | P. aeruginosa Pa6 | BAA 1710 | BAA 1793 | BAA 1797 | BAA 1800 |
|---|---|---|---|---|---|---|---|---|
| 1 | YML-1-117 | 0.5 mM | DMSO/MeOH | 15P/27V | 23 × 21* | 20/23P* | 19/23P* | 23 × 28 |
| 2 | daptomycin | 0.5 mM | water | 0 | 0 | 0 | 0 | 0 |
| 3 | DMSOMeOH | 1:10 | DMSO/MeOH | 0 | 0 | 0 | 0 | 0 |
| 4 | MG-255 | 0.5 mM | DMSO/MeOH | 15V [(1)] | 17/20P* | 16/19P* | 15/20P | 17 × 20 |
| 5 | ciprofloxacin | 5 μg/ml | water | 0 | 0 | 0 | 0 | 0 |

Notes:
M-HII media Conditions
Samples were diluted 1:5 in MeOH. 50 uL added to wells. Plates were incubated at 37° C. for 20 hrs. Pictures were taken after 1 day.
h: Indicates only a hint of growth inhibition detectable, s: Indicates single colonies in the inhibition zone, p: Indicates unclear inhibition zone.
V: Indicates a very unclear inhibition zone
*Indicates a slightly misshapen zone most likely due to solubility issues
[(1)] production of pyroveridine, the native siderophore for this strain of *Pseudomonas*.

FIG. 4 presents agar diffusion assay demonstrating growth inhibitory activity of daptomycin sideromycins against multi-drug resistant *A. baumannii* 1710.

FIG. 5 shows in vitro activity of daptomycin sideromycins HT-10 (tetrasodium salt of MG-255) against multi-drug resistant *Acinetobacter* (dose dependent agar diffusion). Note Daptomycin is not active (arrow), FIG. 6 shows in vitro activity of HT-10 (tetrasodium salt of MG-255) against multi-drug resistant *Acinetobacter* (Raw MIC data).

Syntheses and Biological Studies:

Example 4 Section 1: This section highlights the synthetic work and successful re-synthesis of sideromycin 21 as summarized in Scheme 4. Briefly, deprotection of all the benzyl groups in resynthesized t-butyl ester A13 (an advanced intermediate prepared in the PracticaChem-China laboratory) afforded catechol A14 quantitatively. Acetylation of all the phenol hydroxyl groups (78% yield), followed by deprotection of the t-butyl ester with TFA (trifluoroacetic acid) gave the desired diamine core 22 in 62% yield. The diamine core 22 is a key advanced intermediate

TABLE 2 shows in vitro activity against multi-drug resistant *Acinetobacter* of HT-10 (tetrasodium salt of MG-255) compared to Daptomycin and Ciproflaxin (all units in μM).

| | A. baumannii ATCC 17961 | A. baumannii ARC 3486 | A. baumannii ISR 14-0061 | Ps. aeruginosa 01 | Burkholderia multivorans AU0100 | S. Aureus ISR 14-001 | S. Aureus ISR-002 | E. coli DCO |
|---|---|---|---|---|---|---|---|---|
| HT-10 | 3 | 3 | 3 | >100 | >100 | 6 | 6 | >100 |
| Daptomycin | >100 | >200 | >100 | >100 | >100 | 0.8 | 0.8 | >100 |
| Cipro | 0.2 | >5 | >5 | 0.2 | >5 | 0.2 | >5 | 0.2 |

FIG. 7 shows in vivo activity of HT-10 (tetrasodium salt of MG-255) against *Acinetobacter baumannii* in mice. Y-axis is percent surviving; x-axis is days after inoculation. Note: 5/5 Vehicle and 5/5 daptomycin treated mice were all dead at Day 1; 6 to 0.8 wk old female ICR mice; IP needed for synthesizing proposed sideromycins 21 and 29. An NHS (N-hydroxysuccinimide) active ester mediated coupling, of diamino acid 22 with commercially available ampicillin afforded the desired sideromycin 21 (HKI9924116/HKI9924154-the corresponding, more soluble, sodium salt) in 41% yield.

Scheme 4. Chemical Synthesis of Sideromycin 21 and Siderophore Components.

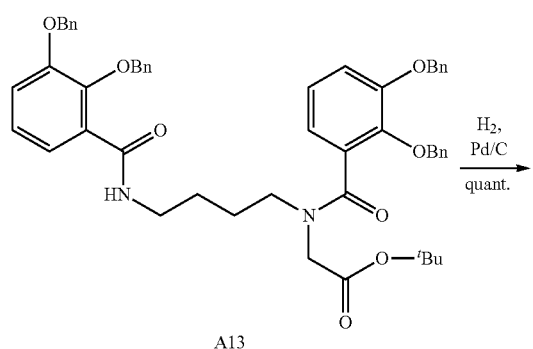

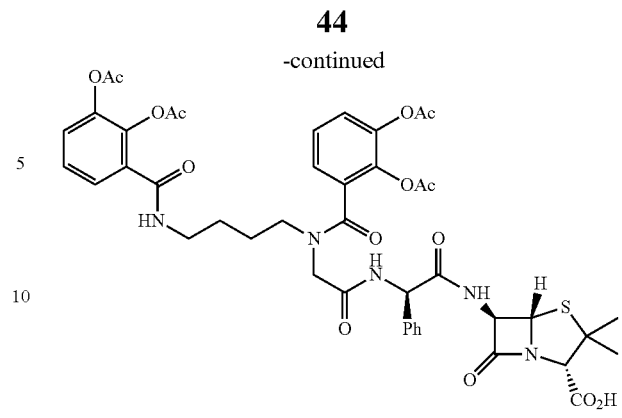

21, HKI9924154 (Na salt)
(PrC-YML-1-18, free acid)

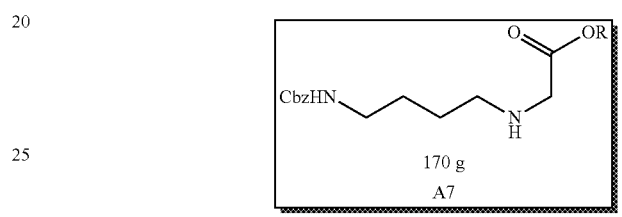

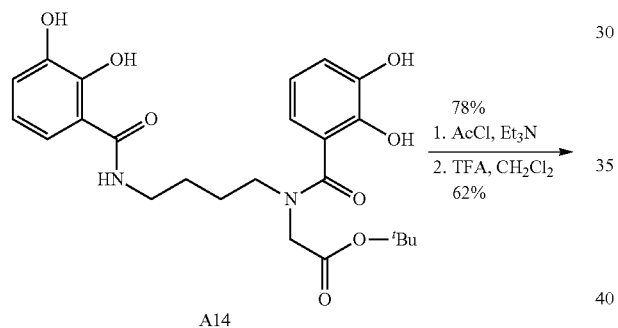

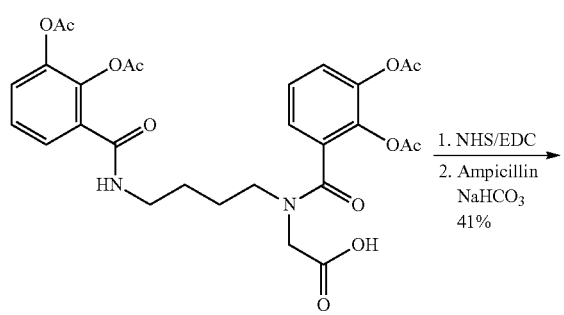

22, diamine core
(in FIG. 10 of the original proposal)

The re-synthesis of sideromycin 21 was carried out on multi-milligram scale, and larger, multi-gram scale syntheses of non-proprietary siderophore components A7 (170 g) and A11 (200 g) needed for this project were carried out.

The newly synthesized sideromycin 21, a conjugate, of our synthetic siderophore with ampicillin, was found to be remarkably active when assayed against several strains of P. aeruginosas, displaying a 16000 fold increase in antibiotic activity over ampicillin itself (entries 1 and 2, Table 3). Most excitingly, when sideromycin 21 was tested against other Gram-negative bacteria, including *E. coli* and *Acinetobacter baumannii* ATCC17961, we discovered that sideromycin 21 (resynthesized HKI-9924116) and the corresponding sodium salt (HKI-9924154) are extremely potent with MIC values of <0.005 μg/mL against representative strains of *E. coli* (entries 4-5, Table 3) and against the specifically targeted pathogen, *A. baumannii* with, an MIC of 0.156-0.313 μg/mL (0.34 μM) whereas the MIC of ampicillin against the same strain was again >250 μM (entry 3, Table 3). This novel finding is significant to the project because *Acinetobacter* is responsible for severe skin wound infections, and is one of the major organisms of concern in this project. As expected, these sideromycins were not active against representative Gram-positive bacteria (M. vaccae, *M. luteus, B. subtilis, S. aureus*, entries 6-9). Thus, preliminary studies already verify our hypothesis that we can design microbe-selective antibiotics, based on sideromycins.

TABLE 3

Antibacterial activity of synthetic sideromycins relative to ampicillin.

| Bacteria | Compound | | | |
|---|---|---|---|---|
| | 21, YML-1-18 | HKI-9924116 | HKI-9924154 (Na salt of 116) | ampicillin |
| | MIC in Fe(−)MHII Media[a] | | | |
| 1 P. aeruginosa-KW799/wt | 0.0156 μM | 0.02-0.06 μg/ml (0.0156 μM) | 0.04-0.052 μg/ml | 250 μM |
| 2 P. aeruginosa-KW799/61 | | 0.052 μg/ml | 0.13 μg/ml | 0.4 μM |
| 3 A. baumannii ATCC- 17961 | 0.156 μM | 0.34 μM 0.313 μg/ml | 0.34 μM 0.313 μg/ml | 250 μM |
| 4 E. coli DC0 | | <0.005 μg/ml | <0.005 μg/ml | |
| 5 E. coli DC2 | | <0.005 μg/ml | <0.005 μg/ml | |
| 6 M. vaccae IMET-10760 | | >10 μg/ml | >10 μg/ml | |
| 7 M. luteus ATCC-10240 | | >10 μg/ml | >10 μg/ml | |
| 8 B. subtilis ATCC-6633 | | >10 μg/ml | >10 μg/ml | |
| 9 S. aureus SG511 | | >10 μg/ml | >10 μg/ml | |

Note:
[a]Iron deficient media to mimic infection models;
wt = wild type;
61 and DC2 = permeability mutants Example 4 Section 2: Scale up synthesis of the first active sideromycin 21 for more extensive assays and hydrogel studies was initiated. Schemes 5-11 summarize syntheses of new sideromycins in protected form, prodrug form and final conjugate form.

As shown in Scheme 5, we were able to use a protected diamine-based bis-catechol, deprotect the methyl ester, activate the resulting carboxylic acid as an NHS (N-hydroxysuccinimide) ester and directly couple it to unprotected antibiotics, ampicillin and a carbacephalosporin, loracarbef. These tetra-benzyl protected conjugates (YML-1-51, loracarbef conjugate, YML-1-52, ampicillin conjugate) were subjected to antibiotic assays to serve as controls. Since these benzyl protected forms cannot efficiently bind iron, they should not have activity comparable to the prodrug or fully deprotected forms of the proposed sideromycins. Once deprotected, these compounds were submitted to our antibiotic assays for comparison with the expectation that the fully deprotected conjugates (sideromycins) should have selective Gram-negative antibacterial activity similar to, but perhaps with different selectivity than, the first synthetic sideromycin 21. (See Example 4 Section 3 for results)

Scheme 5. Syntheses of fully protected sideromycins based on the diamine bis-catechol siderophore.

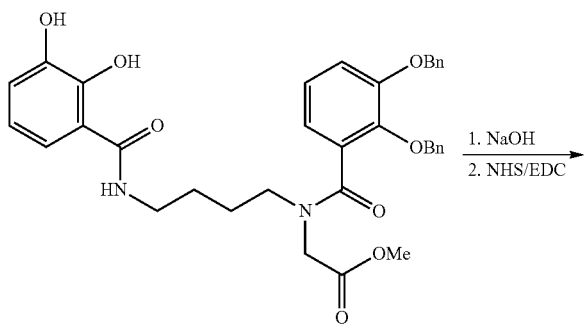

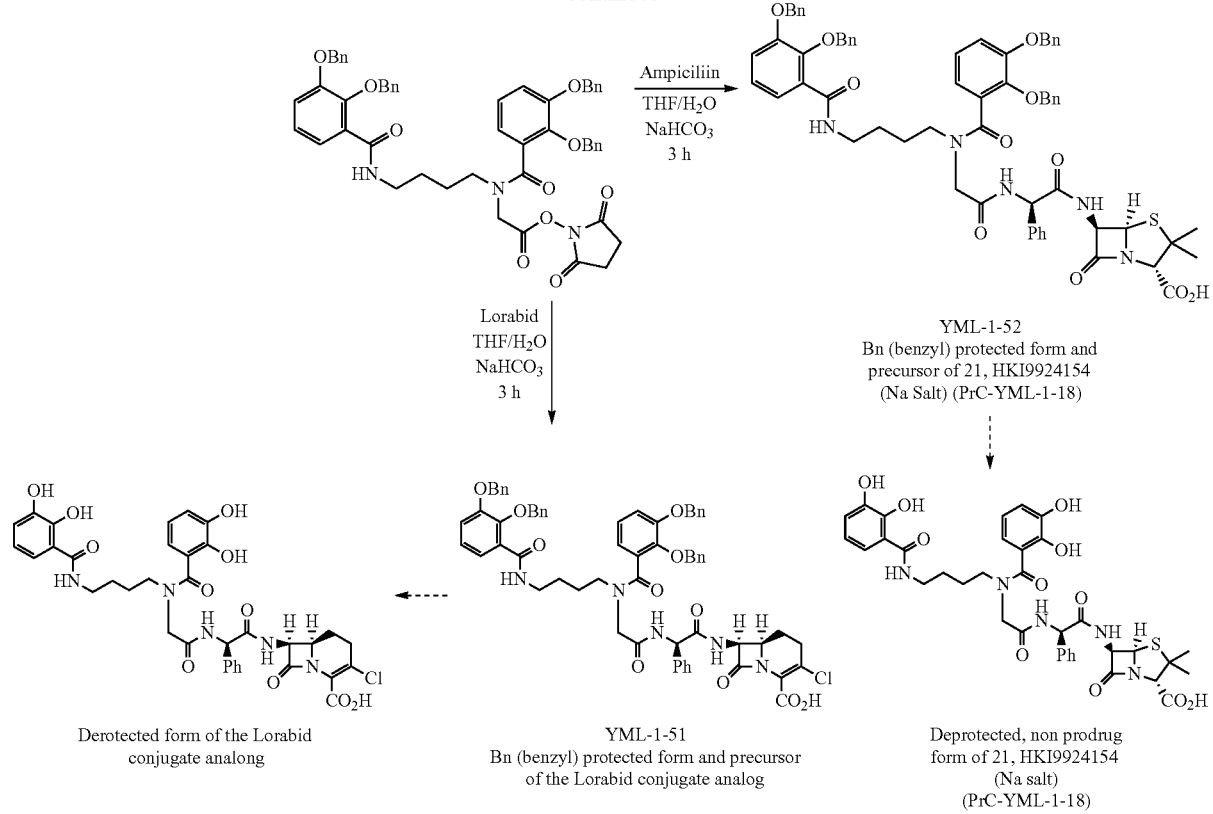

Meanwhile, the same bis-catechol diamine core (22) that was used to prepare the very active conjugate 21 described in the first Example 4 section, was coupled to the carbacephalosporin, loracarbef, to produce a new sideromycin in its acetylated prodrug form (YML-1-45, Scheme 6). Although loracarbef itself is not known to be active against *Pseudomonas*, the carbacephalosporin derived sideromycin YML-1-45 produced a sizable zone of inhibition against *Pseudomonas* in the classical Kirby-Bauer Petri dish assay (shown in FIG. 8). Even more exciting was the assay against *Acinetobacter baumannii*, that showed zones comparable to or even larger than our first sideromycin, 21 (YML-1-18). A full MIC determination against our standard panel (shown in Table 3) of bacteria was subsequently performed.

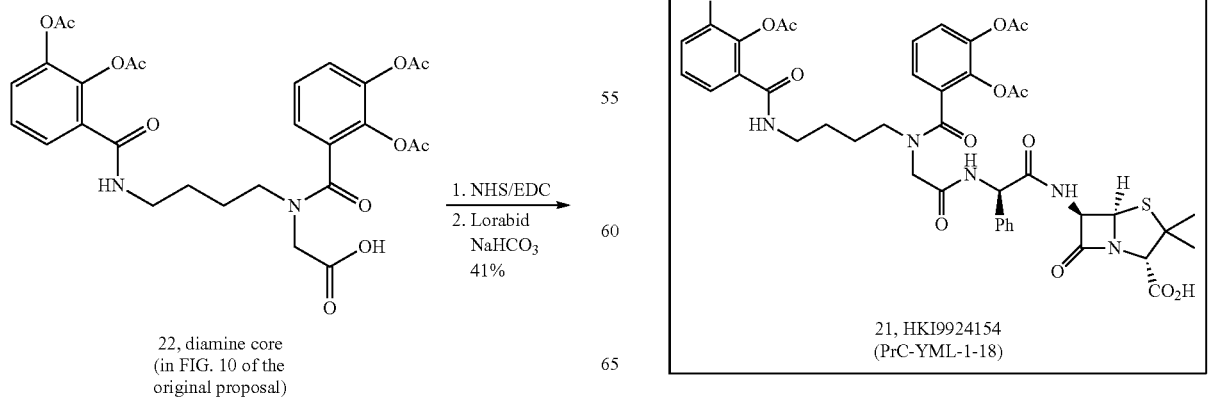

FIG. 8 presents preliminary biological analysis of YML-1-45. (See also Scheme 6)

With ample quantities of dihydroxybenzoic acid and its dibenzyl protected and diacetylated (prodrug) forms obtained from the scale up syntheses in Example 4 Section 2, we were able to carry out syntheses of the proposed triamine core based siderophore as shown in Scheme 7 below. Using the same methodology as described in Scheme 6 for preparation of sideromycins YML-1-18 and YML-1-45 based on the diamine core, we were able to synthesize the first examples of the peracetylated prodrugs of two additional siderophore-antibiotic conjugates, sideromycins YML-1-34 and YML-1-50. Preliminary agar diffusion assays are also shown in FIG. 8 with inclusion of the diamine based conjugates YML-1-18 and YML-1-45 and the parent antibiotics, ampicillin and loracarbef for direct comparison. Again, YML-1-18 and YML-1.45 showed impressive zones of inhibition against wild type *Pseudomonas* (FIG. 9 left panel) and *Acinetobacter* (FIG. 9 right panel) while ampicillin and loracarbef are inactive as expected, Interestingly, the triamine-based ampicillin conjugate, YML-1-34, is very active against wild type *Pseudomonas*, but much less active against *Acinetobacter*. The loracarbef conjugate of the crude product (YML-1-50) was not active against both wild type *Pseudomonas* and *Acinetobacter* but this will need to be verified after additional purification and complete characterization. Taken together, these results indicate that, as proposed, appropriate combinations of siderophore and antibiotic can lead to development of microbe selective antibiotics.

Our bacterial panel/library also includes *Pseudomonas aeruginosa* K799/61, an outer membrane permeable mutant that we use as a control to determine if active transport is being effective in the wild type strain, *Pseudomonas aeruginosa* K799/WT bearing the strong outer membrane permeability barrier. As shown in the center panel, all of our conjugates and ampicillin itself are extraordinarily active against the permeable mutant, whereas loracarbef exhibited a very small zone of inhibition against the permeable mutant, suggesting that by itself it does not have an accessible target in this strain of *Pseudomonas*. Yet, the siderophore conjugate of loracarbef based on the diamine core, YML-1-45, has significant activity against both the wild type and permeability mutant, again suggesting that novel combinations of siderophores and antibiotics can produce remarkably selective anti-bacterial agents that can target specific multi-drug resistant organisms (MDROs).

We determined that the MIC of YML-1-34 against wild type *Pseudomonas aeruginosa* K799/WT was <0.78 µM, further, demonstrating its potent activity against this particular and important MDRO.

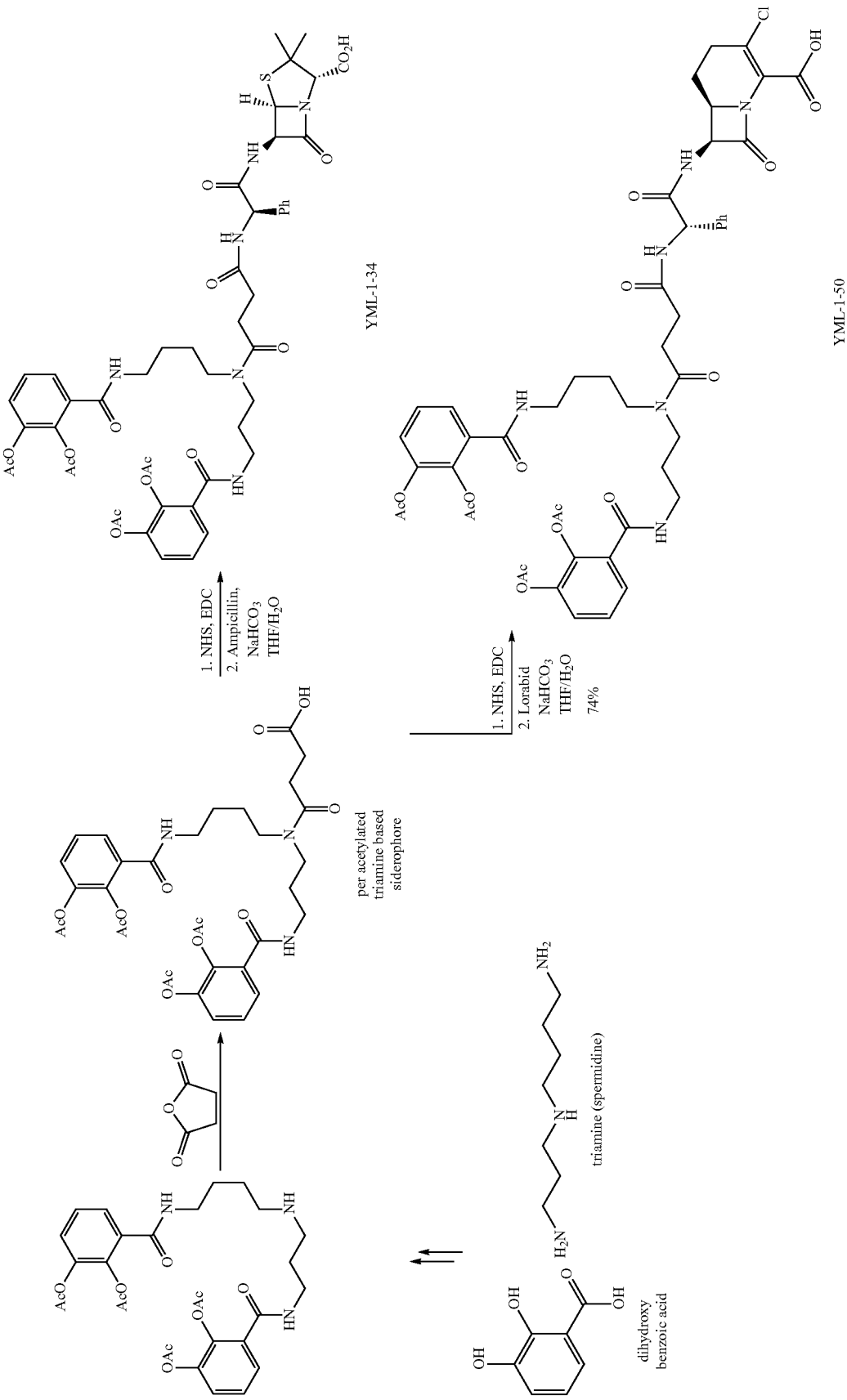
Scheme 7. Syntheses of new sideromycins based on the bis-catechol triamine core. (See also FIG. 9)

FIG. 9 shows zones of inhibition against wild type *Pseudomonas* (FIG. 9 left panel) and *Acinetobacter* (FIG. 9 right panel).

As we previously indicated, a "mixed-ligand" bis-catechol-monohydroxamate based loracarbef conjugate 18 (original numbering) was previously shown to have remarkably selective and potent activity against *Acinetobacter baumannii*. Since we synthesized the bis-catechol triamine core for preparation of conjugates shown in Scheme 7, we used it to prepare the mixed ligand hexadentate siderophore for use in re-synthesis of the corresponding loracarbef conjugate (Scheme 8). While the syntheses was effective, we found that purification of the final mixed ligand loracarbef conjugate required use of reverse phase HPLC, making it less effective for appropriate scale up. We plan to overcome this obstacle by instead preparing the acetylated prodrug forms to facilitate purification while also serving as prodrugs of the new sideromycins. We have initiated gel studies of YML-1-60.

Scheme 8. Synthesis of the mixed ligand-loracarbef conjugate and prodrug to target Acinetobacter.

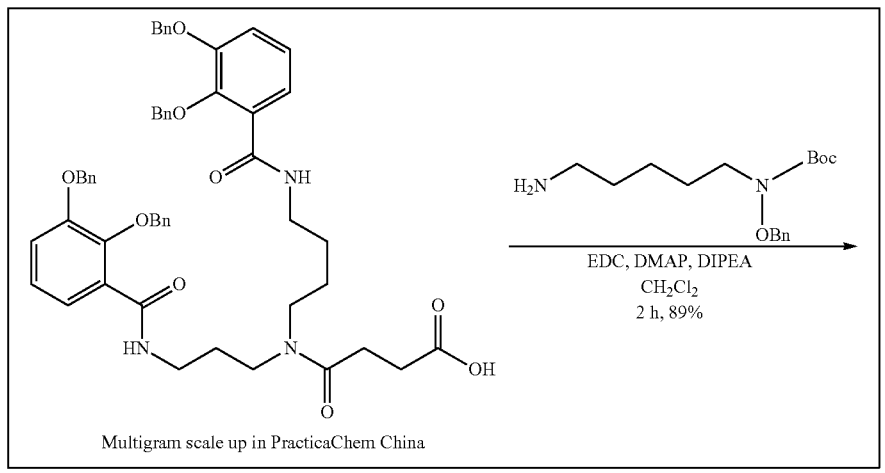

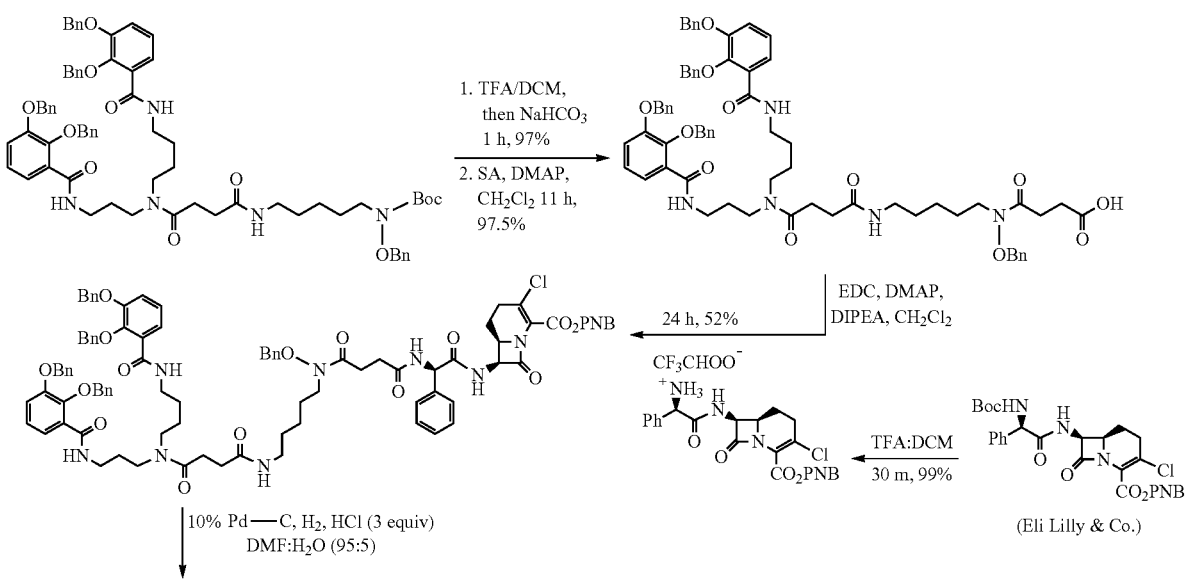

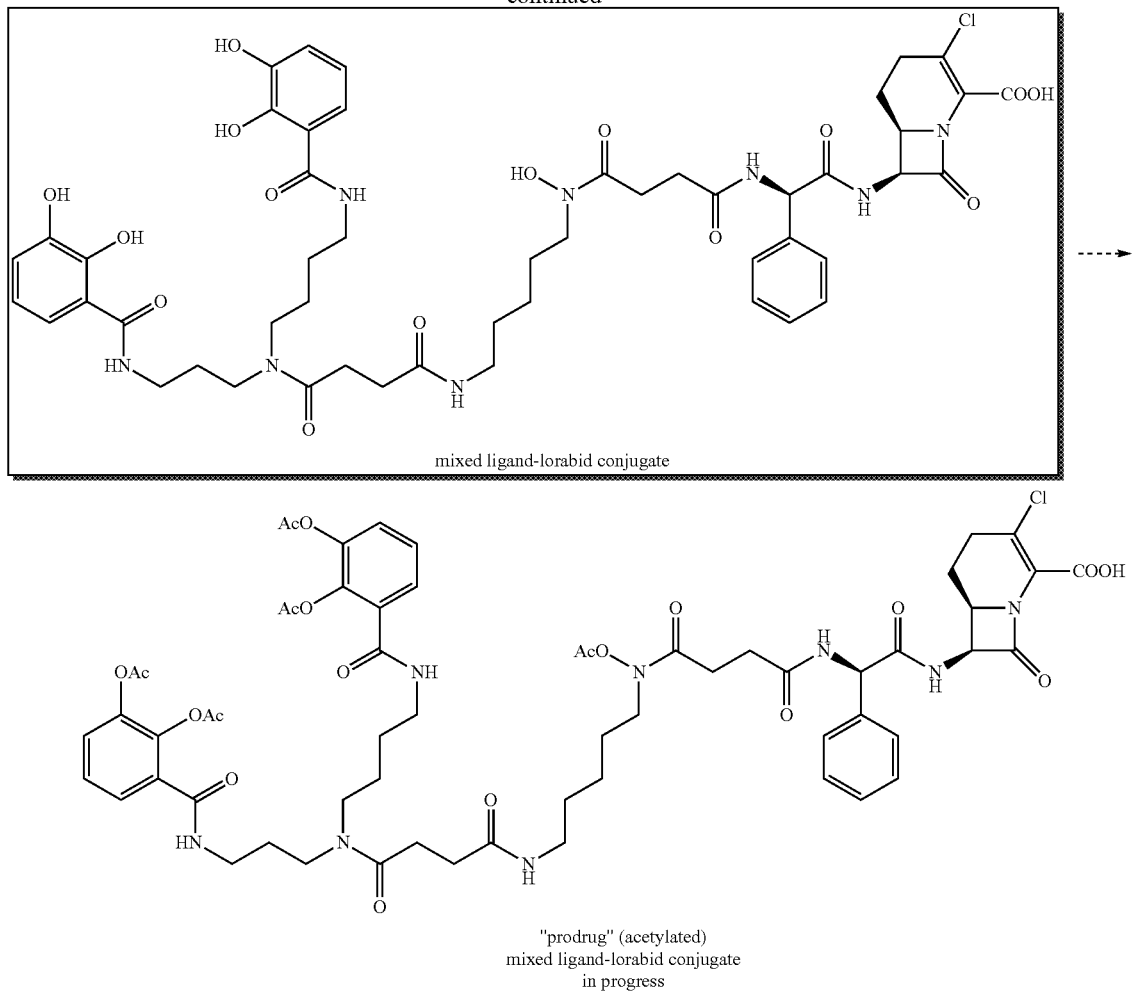

While, as described above, we have been able to prepare testable quantities of several of the proposed sideromycins, scale up syntheses of the non-proprietary components are ongoing. The following schemes depict the optimized, scaleable processes being used. As noted in Scheme 9, significant progress is being made for the scaleup synthesis of the non-proprietary protected forms (ie, 1-10) of the bis-catechol diamine siderophore scaffold and very large quantities are being prepared for continuous production.

Scheme 9. Scale up synthesis of the bis-catechol diamine core.

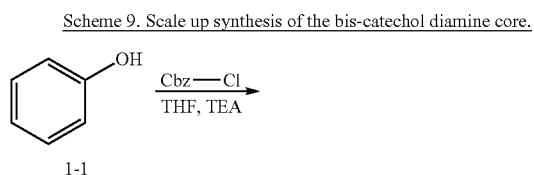

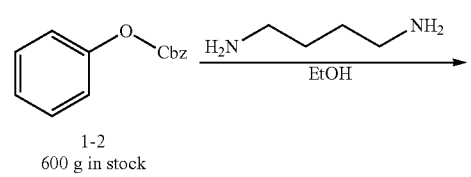

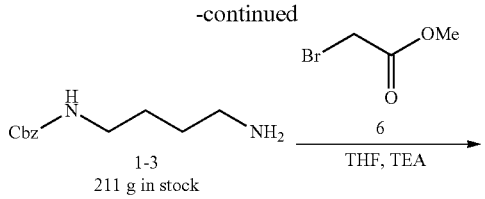

-continued

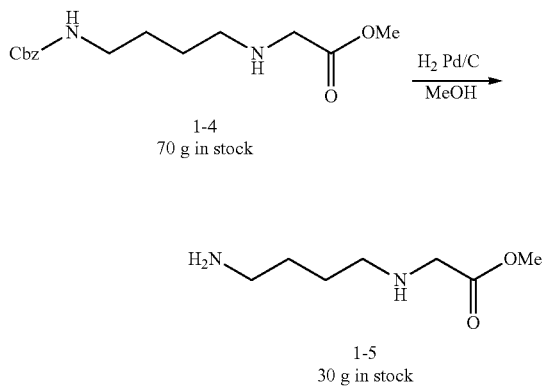

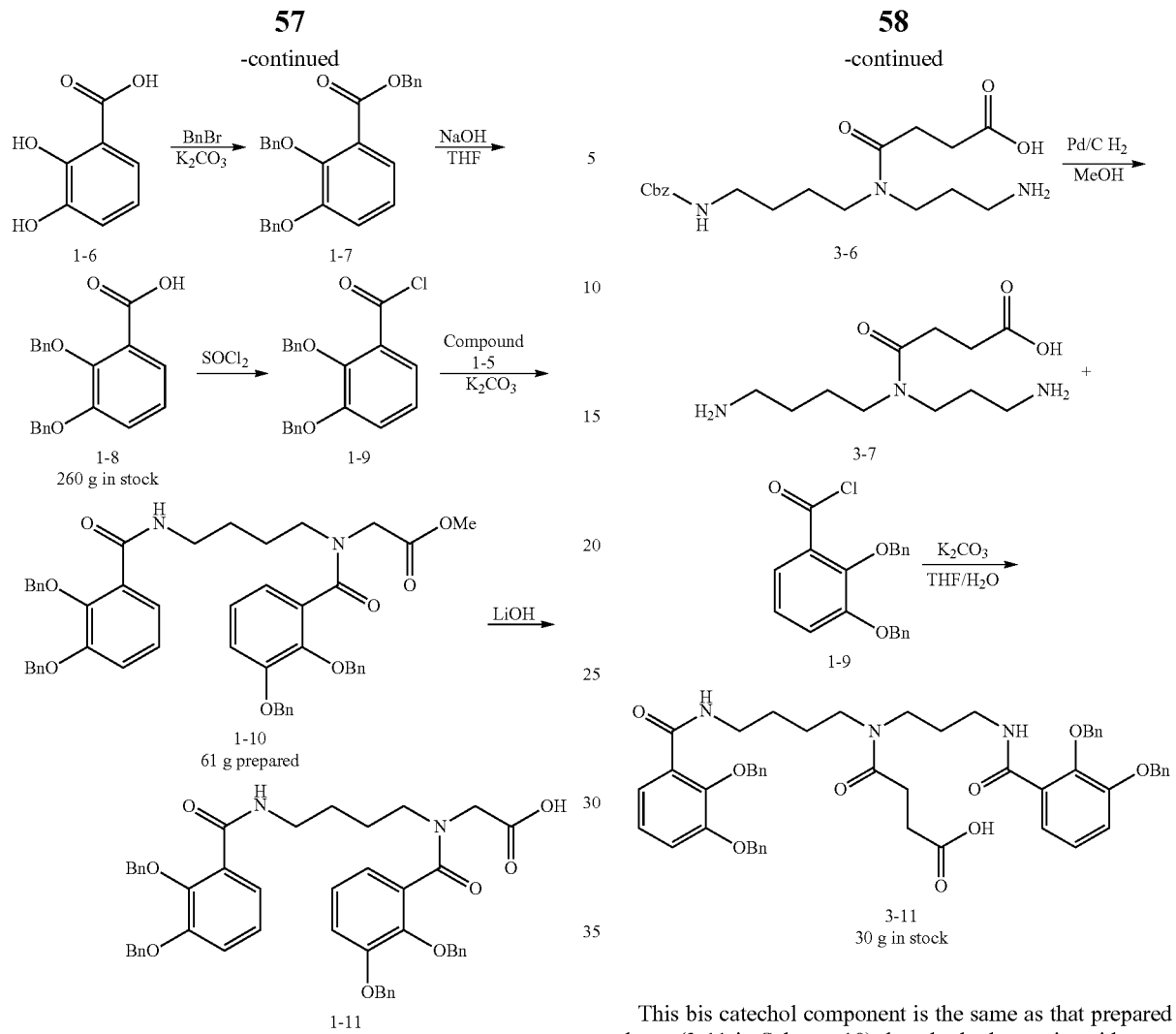

Also noteworthy is that precursors used for synthesis of the bis-catechol diamine core are the same as needed for the triamine based siderophore components. Scheme 10 describes the scale-up synthesis.

This bis catechol component is the same as that prepared above (3-11 in Scheme 10), but the hydroxamic acid component requires separate synthesis which is being performed as shown in Scheme 11.

Scheme 10. Scale up synthesis of the bis-catechol triamine core.

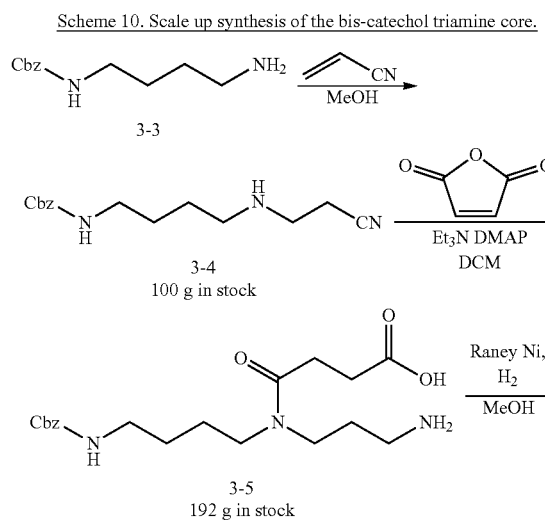

Scheme 11. Synthesis of hydroxamic acid component of mixed ligand siderophore.

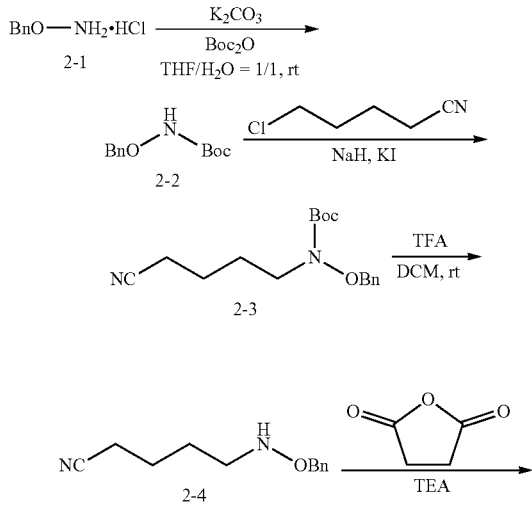

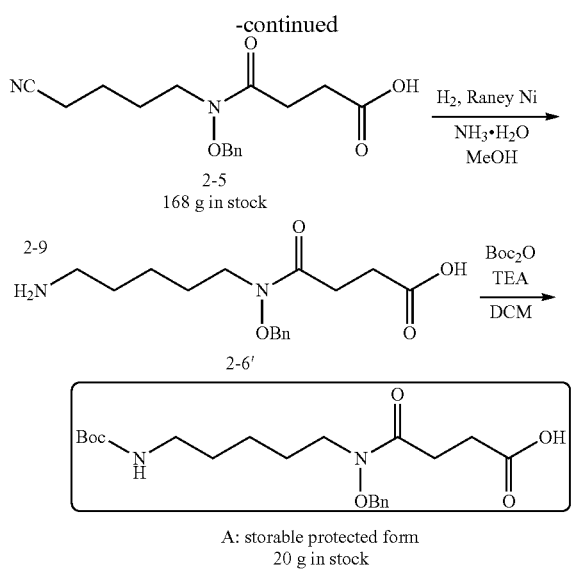

Example 4 Section 3:

This section is organized according to the type of siderophore components used in preparation of the synthetic siderophore-antibiotic conjugates (sideromycins), with emphasis first on the bis-catecholates, then the mixed catechol-hydroxamates. The syntheses and antibiotic assays will be described.

Bis-catechol diamine antibiotic conjugates.

As described in the earlier Example 4 sections, our first synthetic targets were based on the bis-catecholate diamine core 22 As shown below (Scheme 12), we found that we could make active esters (NHS=N-hydroxysuccinimide) of the benzyl protected bis catechol, the acetyl protected bis catechol and, most interestingly, the unprotected bis catechol. While the first two protected versions will be appropriate for coupling to a variety of antibiotics to create new sideromycins, the benzyl protected versions of the final products will require deprotection using reductive conditions that might not be compatible with some potential drug candidates. Since the acetate protected bis catechol is essentially a prodrug for the unprotected bis catechol, as demonstrated earlier based on the activity of YML-1-45 (Scheme 6), we will react the NHS active ester directly with unprotected loracarbef to prepare larger quantities of YML-1-45. Interestingly, under the slightly modified conditions, one of the acetates was removed to reveal the free phenol. YML-1-57. Control studies indicate that the deacetylation reaction is promoted by reactions with nucleophilic solvents during chromatographic purification and or storage in nucleophilic solvents. As expected, this monodeacetylated compound has anti-bacterial activity comparable to the fully acetylated version, YML-1-45.

Related studies on the chemical compatibility of the drug conjugations with the fully deprotected bis catechol siderophore component during the coupling reactions was most gratifying. Indeed, reaction of the unprotected bis catechol active ester with a representative beta-lactam antibiotics, the carbacephalosporin called loracarbef, and ampicillin produced the final conjugates YML-1-60 and YML-1-62 without the need of any subsequent deprotection steps. This new synthetic protocol offers an advantage over our previous synthetic plan, depicted in Scheme 5, by improving the overall synthetic efficiency. As shown in Table 5, the products have outstanding activity against strains of *Pseudomonas aeruginosa* (MIC=0.0156-0.025 μM) and *Acinetobacter baumannii* (MIC=0.03-0.25 μM). YML-1-60 has been studied for impregnation into hydrogels.

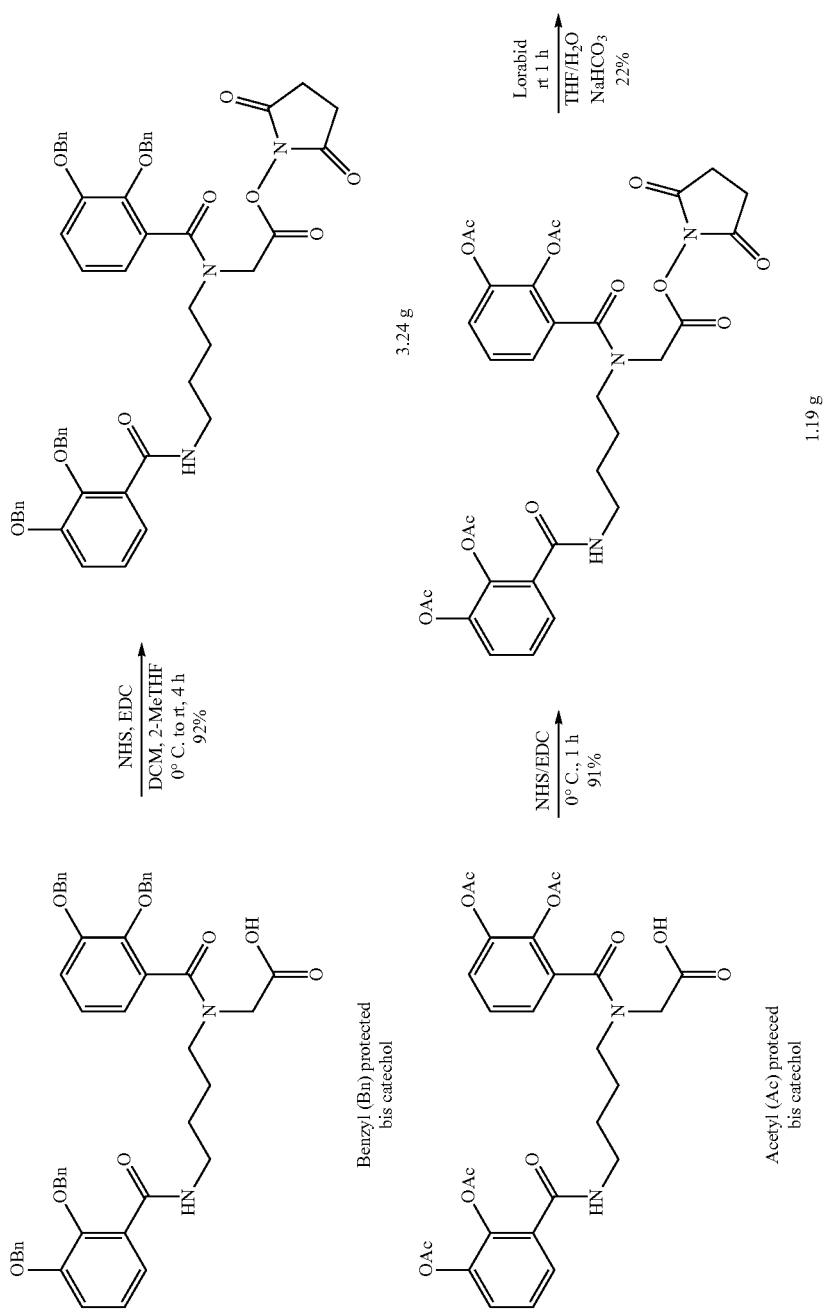
Scheme 12. Generation of bis catechol active esters and direct coupling to antibiotics.

-continued
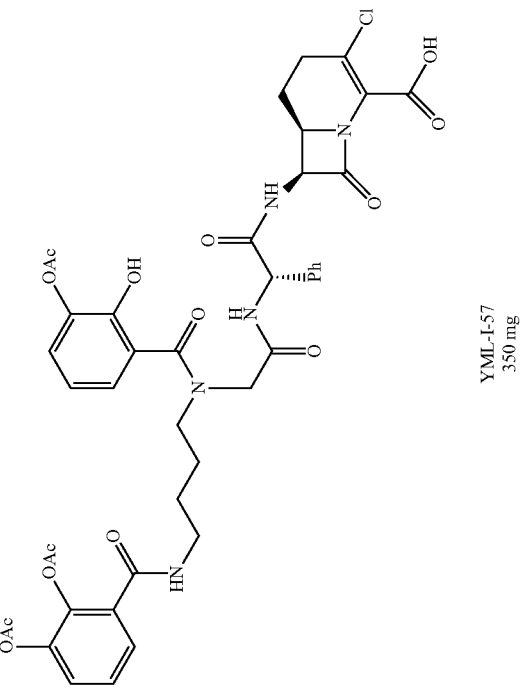
YML-I-57
350 mg
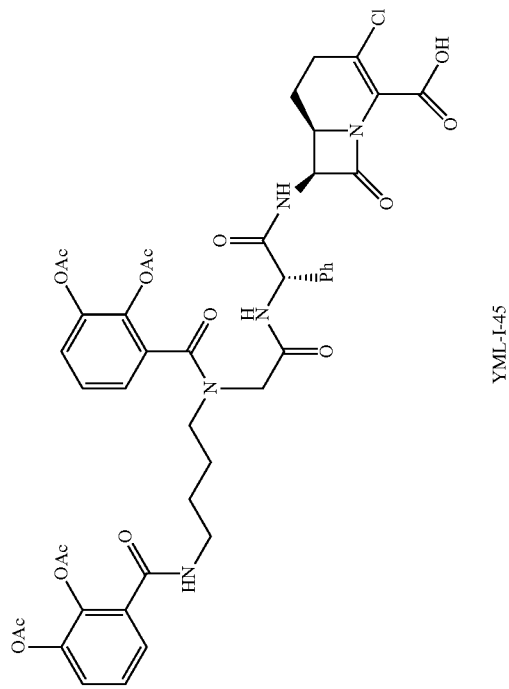
YML-I-45

-continued
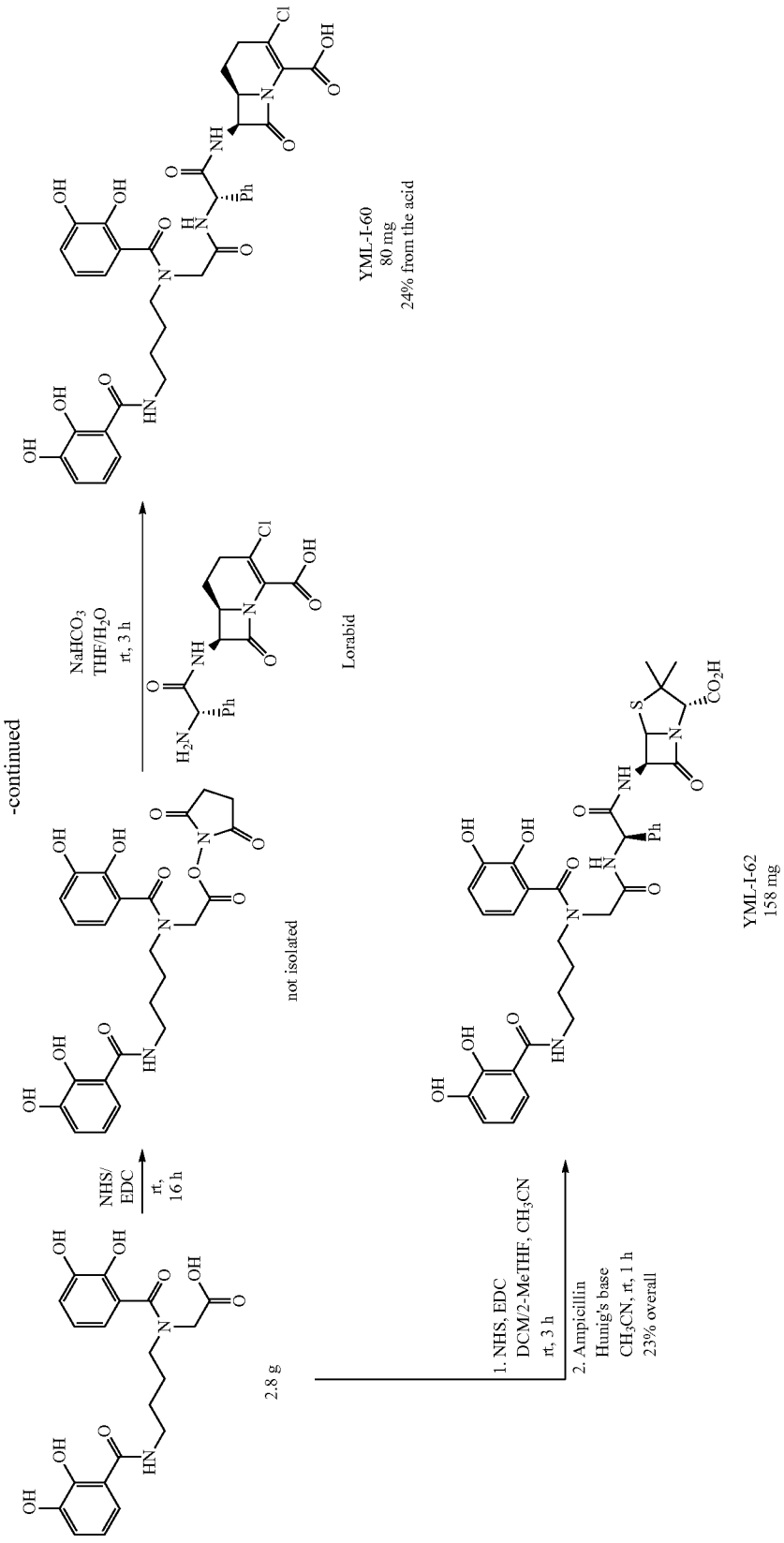

With the successful syntheses of potential sideromycins YML-1-45, YML-1-57, YML-1-60 and YML-1-62 in hand, and related antibacterial studies ongoing, we turned our attention to synthesize potential conjugates with a representative monobactam antibiotic, specifically aztreonam, which is commercially available. Since aztreonam contains a more complex side chain and both a carboxylic acid and sulfonate that might cause compatibility problems with direct coupling reactions of the unprotected bis catecholates, we decided to first study model reactions with the more easily handled benzyl protected bis catechols. Scheme 13 summarizes our very encouraging synthetic results. As shown, the carboxyl and sulfonic acid groups of aztreonam were first neutralized by conversion to their Hunig's base (HB) salts. The bis-ammonium salt was then reacted directly with the NHS active ester of the benzyl protected bis-catechol siderophore described earlier. Though the amine of the aminothiazole component of aztreonam is known to not be very nucleophilic, we found that the coupling reaction proceeded in reasonable yields (63% on a small scale, 50% on a larger scale).

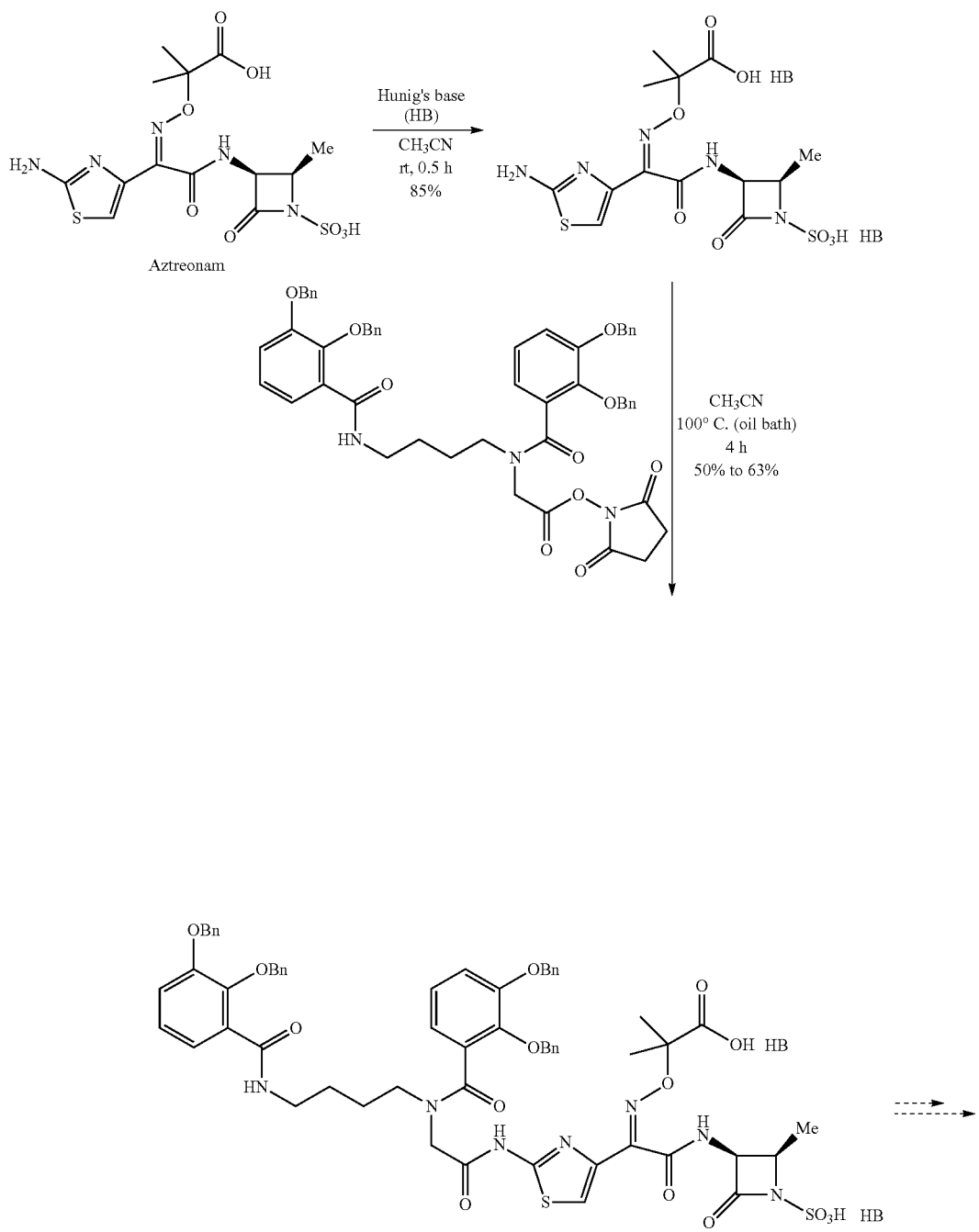

Scheme 13. Preliminary studies of coupling of bis catechol siderophore with aztreonam.

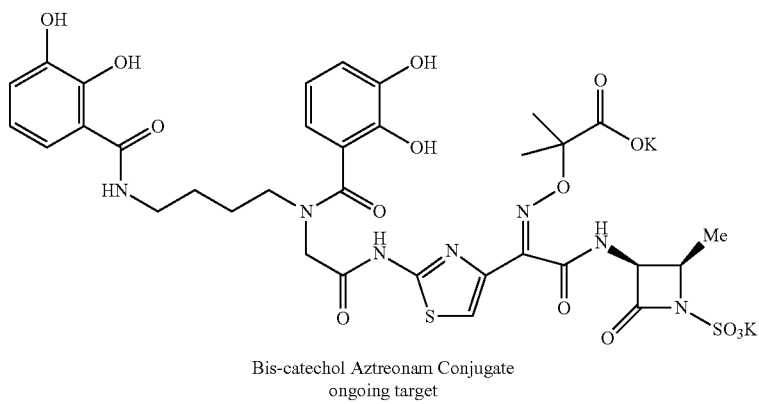

Bis-catechol Aztreonam Conjugate
ongoing target

Bis-catechol triamine antibiotic conjugates.

The syntheses of bis-catechol triamine based ampicillin and loracarbef conjugates YML-1-34 and YML-1-50 are described earlier along with preliminary agar diffusion (Kirby-Bauer) Petri dish assays. (Scheme 7). The results are included in Table 5 which is provided after the chemical syntheses discussion.

Mixed ligand (bis-catechol mono-hydroxamate) siderophore components and antibiotic conjugates.

In Example 4 section 2 we described small scale resynthesis of a mixed ligand-loracarbef conjugate with outstanding activity against *Acinetobacter baumannii*. Slightly modified syntheses were proposed to circumvent purification problems associated with potential scale up of the original route (Scheme 8). The improved synthesis is shown in Scheme 14 below. The numbering system in Scheme 14 (MG-#) is used for convenience. The synthetic routes to the siderophore components of the proposed synthetic sideromycins starts from readily available starting materials, and the synthetic steps are concise and amenable to scale up. Briefly, Boc protection of aminopentanol (MG-1) followed by coupling with troc-O-benzyl hydroxylamine (MG-S), provided the protected hydroxamate component MG-6. Subsequently, deprotection of Boc of the hydroxamate component, and EEDQ-mediated coupling with siderophore MG-7 followed by simultaneous deprotection/succinoylation (Zn/succinic anhydride) provided the biscatechol hydroxamate siderophore core MG-9 (the fully benzyl protected mixed ligand siderophore).

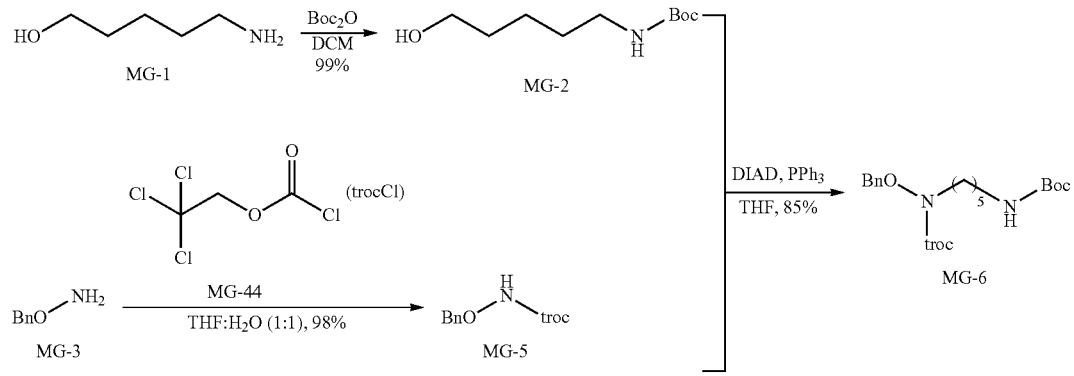

Scheme 14. Improved synthesis of benzyl protected mixed ligand siderophore.

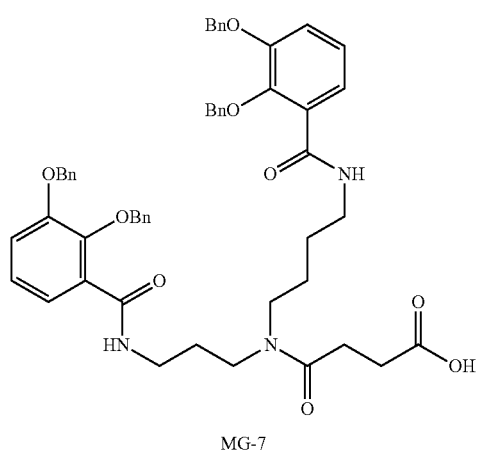

MG-7

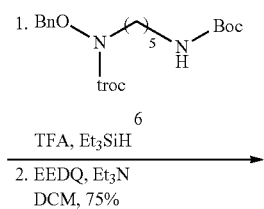

1. BnO-N(CH₂)₅-NH-Boc, troc
   6
   TFA, Et₃SiH
2. EEDQ, Et₃N
   DCM, 75%

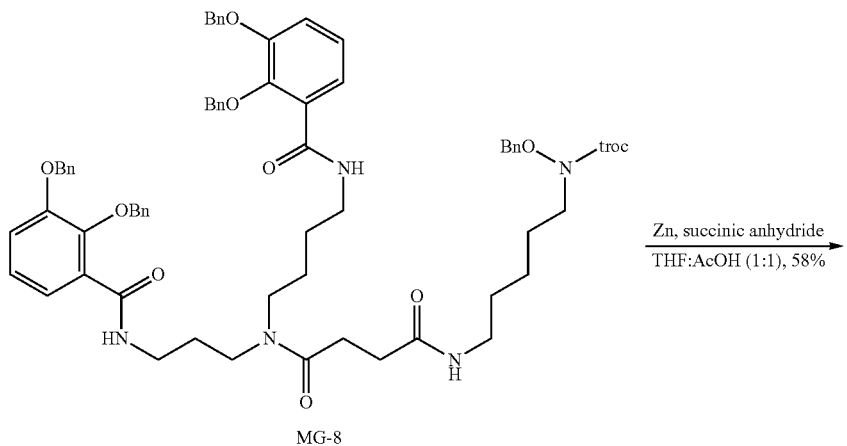

MG-8

Zn, succinic anhydride
THF:AcOH (1:1), 58%

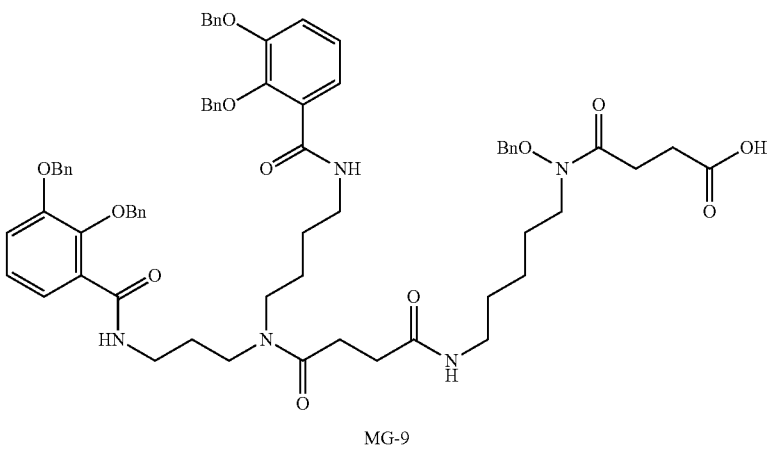 [SMILES: O=C(O)CCC(=O)N(CCCCCNC(=O)CCC(=O)N(CCCCNC(=O)c1cccc(OCc2ccccc2)c1OCc1ccccc1)CCCNC(=O)c1cccc(OCc2ccccc2)c1OCc1ccccc1)OCc1ccccc1]

MG-9

To avoid the problem during global debenzylation of antibiotic conjugates, to Minimize problem during purification and isolation of the desired conjugates, and mostly since it has been demonstrated that acetate "protected" conjugates serve effectively as a prodrug of the free catechol form, the acetyl-protected conjugates were made for further evaluation. Thus, the benzyl-protected mixed ligand catechol-hydroxamate siderophore MG-9, after deprotection under hydrogenolytic conditions (MeOH, 10% Pd—C, H₂, 1 atm, RT), was subjected to exhaustive acylation (AcCl, Et₃N, DMAP, THF, 0° C. to RT, 18 h) as shown in Scheme 15. The crude pentaacetyl siderophore was purified by reverse phase (C-18) column chromatography eluting with CH₃CN/H₂O gradient containing 0.1% HCO₂H modifier, to obtain MG-18b as an amorphous white solid (Scheme 15).

Scheme 15. Synthesis of the acetyl protected mixed ligand siderophore.

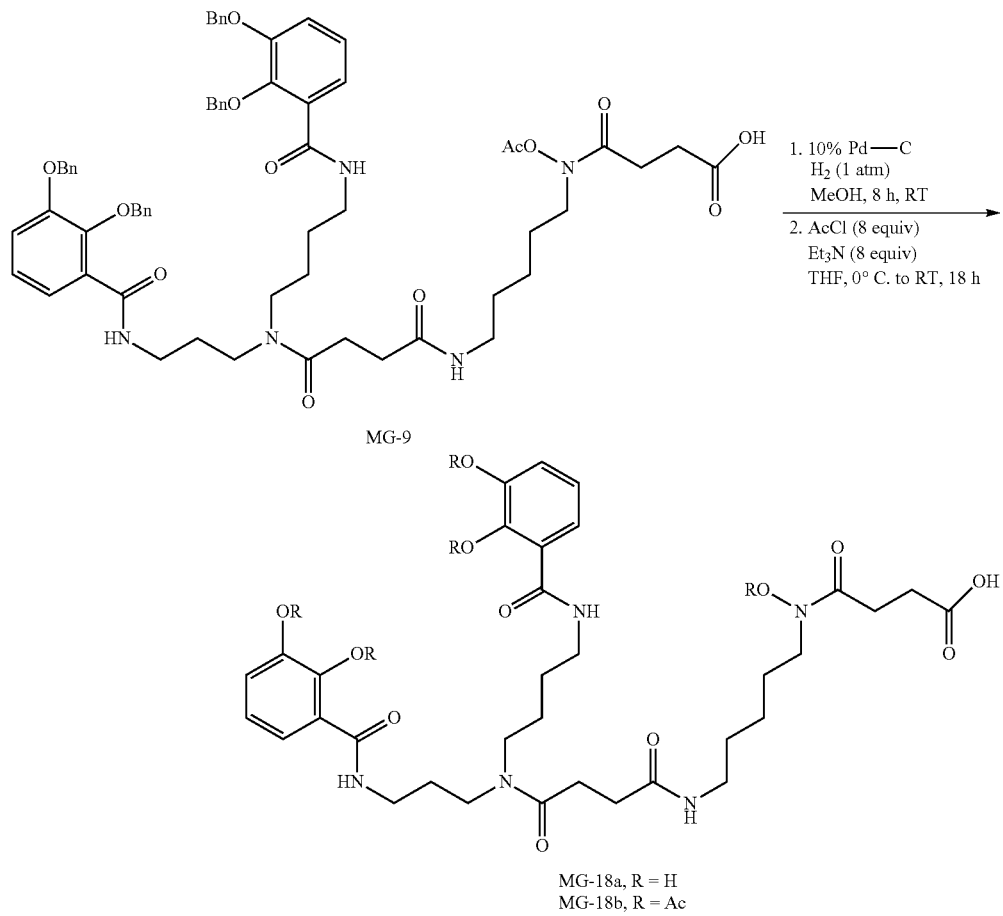

With, both the benzyl and acetyl protected mixed ligand siderophores successfully prepared, we will initiate coupling reactions with representative antibiotics (loracarbef, ampicillin, aztreonam) to produce new sideromycins in an effort to determine structure-activity-relationships. If the activities are as outstanding as anticipated against *acinetobacter*, we will attempt to shorten the syntheses by eliminating the use of protecting groups as we have done in the previously described syntheses of the bis-catechol conjugates.

We determined that the synthetic mixed-ligand loracarbef conjugate (Scheme 8) is extremely potent against *Acinetobacter*. It was known since 1994 that *Acinetobacter* produced and utilized a mono catechol-mono hydroxamate siderophore initially called acinetobactin, but recently structurally reassigned as shown in Scheme 16 below, and although it is a mixed ligand system, it was not a bis-catechol mono-hydroxamate.

Scheme 16. Natural siderophores produced by Acinetobacter and our closely related antibiotic conjugate.

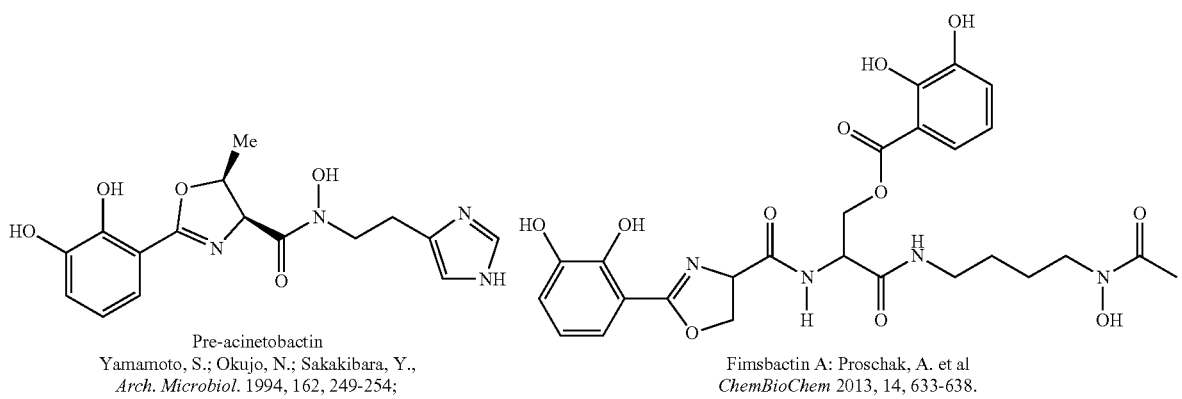

Pre-acinetobactin
Yamamoto, S.; Okujo, N.; Sakakibara, Y.,
*Arch. Microbiol.* 1994, 162, 249-254;

Fimsbactin A: Proschak, A. et al
*ChemBioChem* 2013, 14, 633-638.

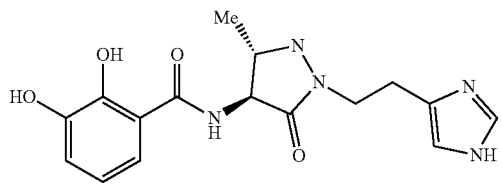

Acinetobactin
Microbiology 2004, 150, 3657-3667;
Microbiology 2004, 150, 2587-2597;
*J. Am. Chem. Soc.* 2008, 130, 12282-12284;
*J. Am. Chem. Soc.* 2009, 131, 5056-5057;
*Chem. Pharm. Bull.* 2010, 58, 1552-1553.

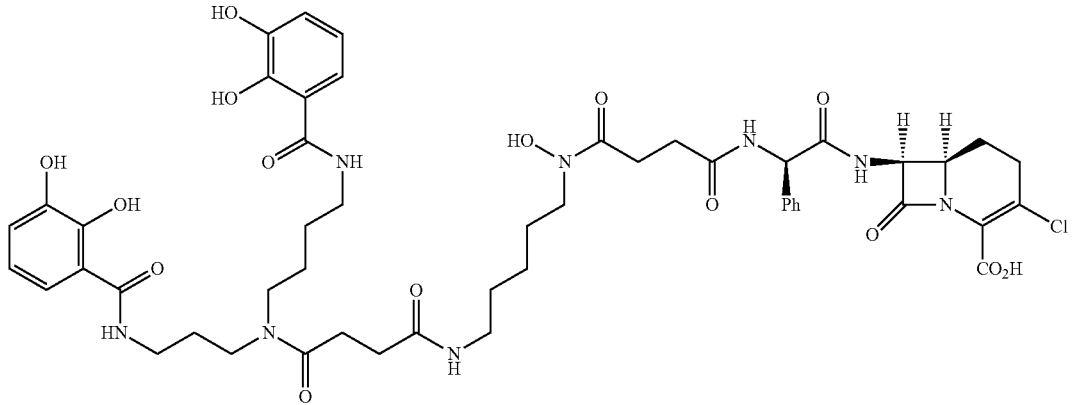

Synthetic siderophore-antibiotic conjugate with selective
anti-acinetobacter activity. Resynthesis & retest: MIC = 0.0078 μMl
Wencewicz, T. A.; Miller, M. J. *J. Med. Chem.* 2013, 56, 4044-52.

Multihydroxamate siderophore components.

We expect that multi-hydroxamate based siderophore-antibiotic conjugates could have activity against bacteria that rely on hydroxamic acid containing siderophores. We synthesized representative catechol and mixed catechol-hydroxamate siderophore components and related conjugates. With the extensive results obtained on those two first classes of compounds, we have initiated scale up synthesis of representative multi-hydroxamates. We initiated production of 100 g of the protected bis-hydroxamate labeled as DOD-2-9 in the following table (Table 4).

Scale up syntheses.

Synthetic schemes (Schemes 9-11 above) have been provided for scale up syntheses of several of the siderophores and components, Table 4 below, summarizes the scale up results. The chemistry is amenable to scale up to multi to hundred gram amounts so that ample amounts of materials are available for syntheses of targeted sideromycins. Also, a suitably protected form of the protected catechol oxazoline component (DOD-B-6) is prepared in anticipation of synthesis of fimsbactin and related sideromycins. We have obtained 40 grams of the oxazoline. The synthesis of mixed ligand DOD-MG-9-A has been scaled up and 10.5 grams are now available.

TABLE 4

| | Scale up syntheses. | | | |
|---|---|---|---|---|
| Compound ID | Structure | requirements | Delivered | In stock |
| DOD-1-10 | 1-10 | 100 g | 40 g + <br> 21 g + <br> 40 g | 0 <br> All <br> delivered |

TABLE 4-continued

Scale up syntheses.

| Compound ID | Structure | requirements | Delivered | In stock |
|---|---|---|---|---|
| DOD-1-4 | 1-4 | 50 g | 15.8 g + 70 g | 5 g |
| DOD-1-7 | 1-7 | 50 g | 50 g | 0 |
| DOD-2-9 | 2-9 | 100 g | 0 | 60 g |
| DOD-3-11 | 3-11 | 100 | 27.5 g + 50.5 g | 30 g |
| DOD-3-20 | 3-20 | 100 g | 0 | 0 |
| DOD-B-6 | B-6 | 40 g | 40 g | 0 |

TABLE 4-continued

Scale up syntheses.

| Compound ID | Structure | requirements | Delivered | In stock |
|---|---|---|---|---|
| DOD-MG-9-A | 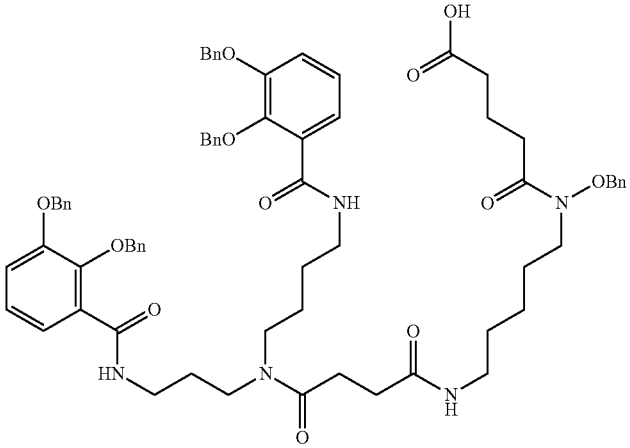<br>MG-9-A | 10 g | | 10.5 g in stock |

Biological Assays.

Antibacterial studies.

Table 3 that was included in the first Example 4 section provides antibacterial data for the first synthetic sideromycins we prepared and studied. The second Example 4 section elaborated and expanded on that data with inclusion of representative antibacterial data in the text and associated pictures of Petri dish assays. Table 5, below provides a summary of antibacterial activity of some embodiments of the conjugates. MIC (minimum inhibition concentration) is given in μM and AD (agar diffusion zones of inhibition are given in mm from Kirby-Bauer Petri dish growth inhibition studies).

Clinical isolates:

Clinical isolates of strains of *Pseudomonas* and *Acinetobacter* from wounded soldiers are available for bioactivity studies with our synthetic sideromycins. Positive results against these clinical isolates will validate that we are able to target the specific strains found to be so detrimental to wounded warriors.

We obtained a clinical isolate of *Pseudomonas* from a cystic fibrosis patient. We typed the clinical isolate and confirmed it to be *Pseudomonas* as expected. Preliminary tests indicate that this clinical strain is indeed a "super bug" that is resistant to all antibiotics tested so far, including ampicillin, amoxicillin, loracarbef and ciprofloxacin. However, two of our his catechol ampicillin conjugates YML-1-18 and YML-1-62 were potent against the same strain with MIC values of 0.4-0.75 μM. The results are included in Table 5 under "Pa-Da-1304 CF patient isolate". Thus, our "Trojan Horse" approach shows tremendous promise for treatment of severe clinically relevant pseudomonal infections.

TABLE 5
Antibacterial assay results for synthetic siderophore-antibiotic (synthetic sideromycins).
| Compound | Structures | MIC in μM, AD = agar diffusion inhibition zones in (mm) | | | | | | | |
|---|---|---|---|---|---|---|---|---|---|
| | | Pa PaO1 | Pa KW799/wt | Pa KW799/61 | Pa4 | Pa6 | Pa-Da-1304 CF patient isolate | A. baumannii | E. coli DC0 | E. coli DC2 |
| YML-I-18 | 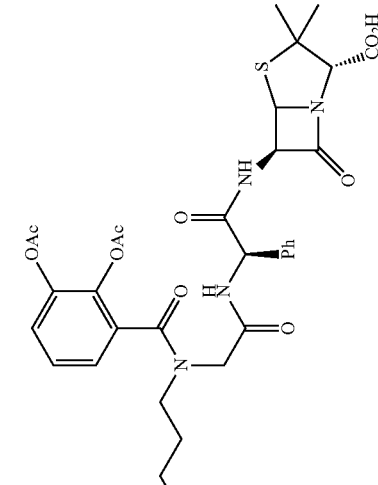 | 0.0156 | 0.0156-0.0313 | 0.03 | 0.03 | >100 | 0.4-0.75 | 0.156-0.1250 (AD = 32) | (AD = 40) |
| YML-I-27 | 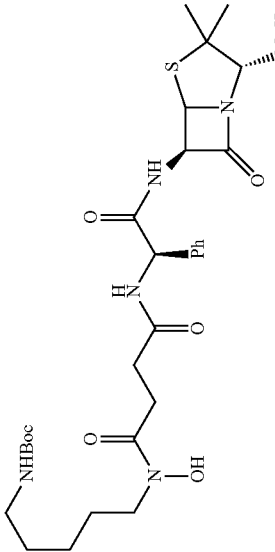 | | (AD = 0) (AD = 16) | (AD = 24) (AD = 24) | | | | (AD = 17) | (AD = 0) | (AD = 26) |

TABLE 5-continued
Antibacterial assay results for synthetic siderophore-antibiotic (synthetic sideromycins).
| Compound | Structures | MIC in μM, AD = agar diffusion inhibition zones in (mm) | | | | | | | |
|---|---|---|---|---|---|---|---|---|---|
| | | Pa01 | Pa KW799/wt | Pa KW799/61 | Pa4 | Pa6 | Pa-Da-1304 CF patient isolate | A. baumannii | E. coli DC0 | E. coli DC2 |
| YML-I-57 | 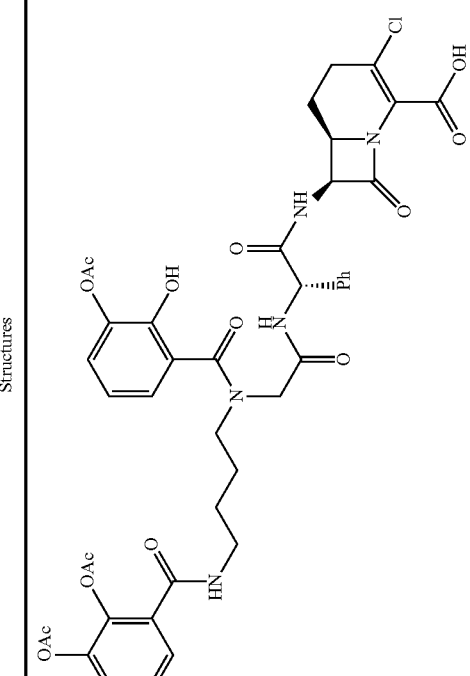 | 0.78 | 0.025 | 0.125 | 12 | 1.56 | >100 | 0.02-0.0625 | 0.006 | 0.006 |
| YML-I-60 | 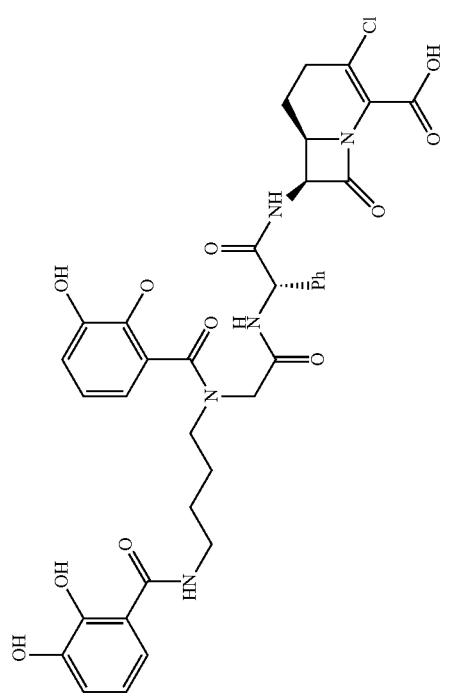 | 1.5 | 0.025 | 0.125-0.025 | 12 | 6 | >100 | 0.03-0.06 | | |

TABLE 5-continued

Antibacterial assay results for synthetic siderophore-antibiotic (synthetic sideromycins).

MIC in μM, AD = agar diffusion inhibition zones in (mm)

| Compound | Structures | Pa01 | Pa KW799/wt | Pa KW799/61 | Pa4 | Pa6 | Pa-Da-1304 CF patient isolate | A. baumannii | E. coli DC0 | E. coli DC2 |
|---|---|---|---|---|---|---|---|---|---|---|
| YML-I-45cr | (structure) | | | (AD = 18) | | | | (AD = 18) | (AD = 31) | (AD = 38) |
| YML-I-62 | (structure) | 0.0156 | 0.0156 | 0.0078 | 0.0156 | 0.78 | 0.25 | | | |
| Lorabid | | >200 | >200 | 50 | >200 | >200 | | | | |
| Ampicillin | | >200 | 200 | 3.13 | >200 | >200 | | | | |

TABLE 5-continued
Antibacterial assay results for synthetic siderophore-antibiotic (synthetic sideromycins).
| | | MIC in µM, AD = agar diffusion inhibition zones in (mm) | | | | | | |
|---|---|---|---|---|---|---|---|---|
| Compound | Structures | Pa01 | Pa KW799/wt | Pa KW799/61 | Pa4 | Pa6 | Pa-Da-1304 CF patient isolate | A. baumannii | E. coli DC0 | E. coli DC2 |
| YML-1-34cr | 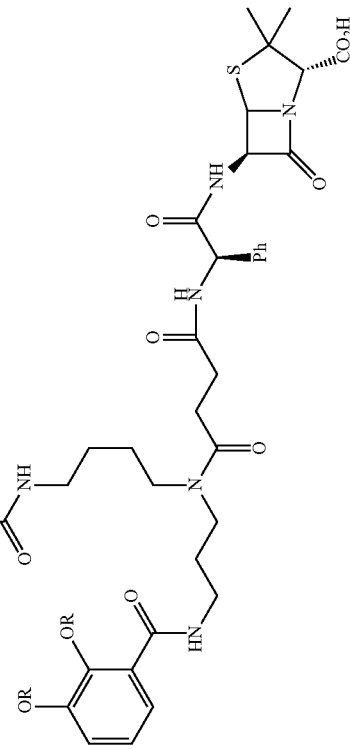 R = H, Ac | | 0.78 | | | | | 6 | | |

TABLE 5-continued
Antibacterial assay results for synthetic siderophore-antibiotic (synthetic sideromycins).
| Compound | Structures | MIC in μM, AD = agar diffusion inhibition zones in (mm) | | | | | | | |
|---|---|---|---|---|---|---|---|---|---|
| | | Pa01 | Pa KW799/wt | Pa KW799/61 | Pa4 | Pa6 | Pa-Da-1304 CF patient isolate | A. baumannii | E. coli DC0 | E. coli DC2 |
| YML-1-50cr | 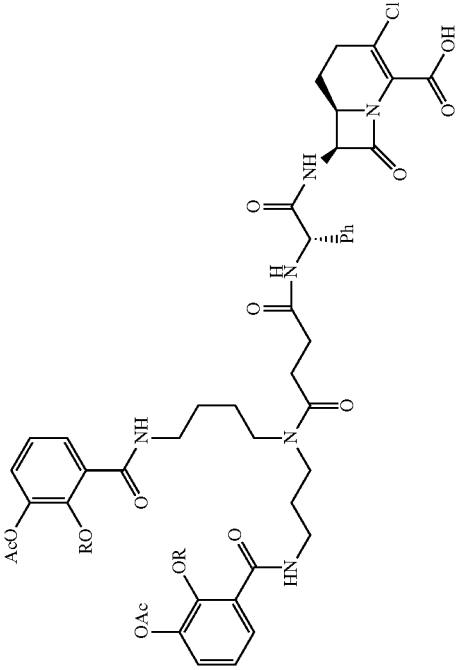 R = H, Ac | | >200 | | | | | 100 | | |

Example 4 Section 4:

Syntheses: As indicated by the antibacterial studies shown in Table 5 above, we have prepared several compounds with remarkably potent activity against targeted MDROs, especially against forms of *Pseudomonas aeruginosa* and *Acinetobacter baumannii*. We initiated scale up syntheses of two conjugates, YML-1-60, the bis catechol-loracarbef conjugate with outstanding activity against *A. baumannii* and YML-1-62, the bis catechol ampicillin conjugate with outstanding activity against *P. aeruginosa*. The bis catechol siderophore component was chosen since the corresponding conjugates are very active, and we obtained 100 g of the protected precursor (DOD-1-10, shown in Table 4). Full deprotection was performed on gram scale, and the resulting diamine based bis catechol free carboxylic acid was converted to the corresponding N-hydroxysuccinimide active ester and directly separately coupled to loracarbef and ampicillin to give gram amounts of YML-1-60 and YML-1-62, respectively (Scheme 17).

Hydrogel impregnated sideromycins and antibacterial studies:

We considered gels of varying viscosity prepared from a solid starting material and water. We prepared gels with varying amounts of water and water/DMSO with and without the synthetic sideromycins YML-1-60 and YML-1-62.

Experimentally, it was determined that predissolving the sideromycins in 10% DMSQ/water and mixing with 10% gel (weight to volume) in water provided clear homogeneous gels. The viscosity was ideal for transfer by syringe onto agar diffusion plates that had been inoculated with the target bacteria.

We investigated whether the sideromycin absorbed in the gel be able to diffuse out of the gel and into the agar to effect antibacterial growth. As a control, the sideromycin alone, without gel, was added in a separate 9 mm well, as usual. As shown in the upper left agar plate of the set of four plates pictured in FIG. 10, inoculation of the agar with *A. baumannii* (ATCC 17961) and immediate standard incubation at Scheme 17. Scaleup synthesis of representative sideromycins.

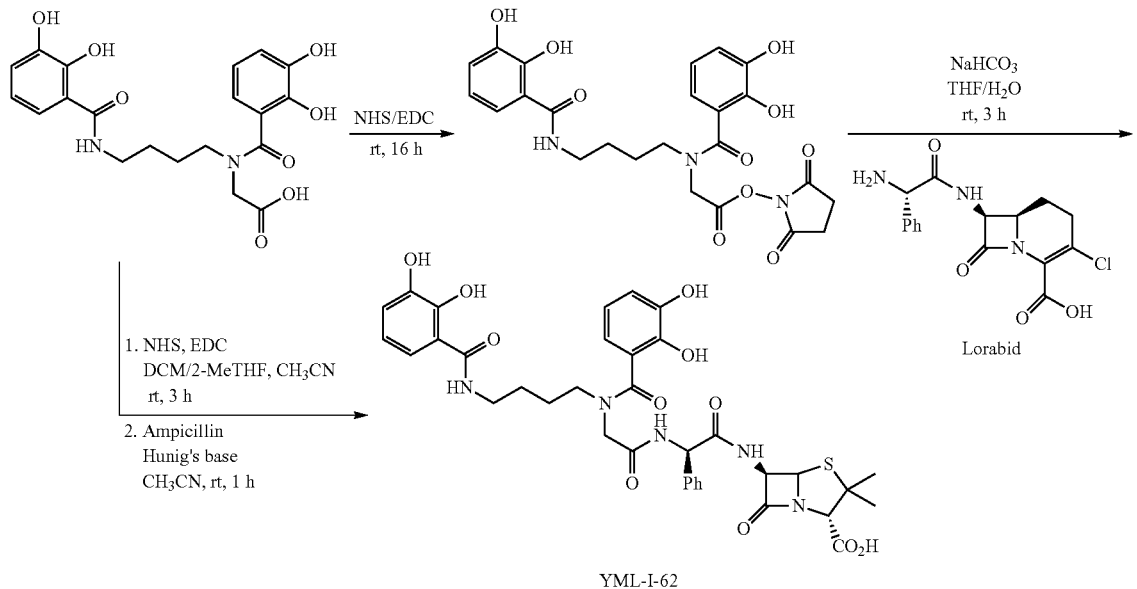

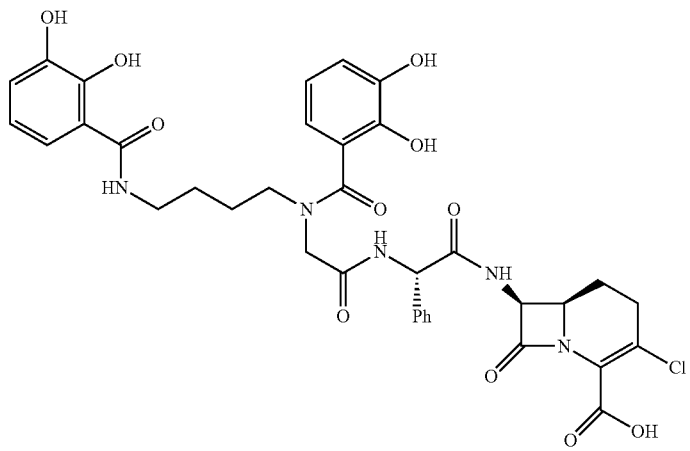

37° C. for 22 hours revealed zones of inhibition around the sideromycin-containing gel and the sideromycin itself, while no inhibition was seen for the antibiotic, loracarbef, itself since it cannot be actively transported into the bacteria without the siderophore component. This first day incubation demonstrated that the sideromycin was effectively released by diffusion into the agar as desired.

The second question was whether the sideromycin continue to be released and be able to effect bacterial growth inhibition over extended periods. Thus, additional identical agar plates were prepared and stored at 4° C. for 24, 48 and 72 hours to allow diffusion of the sideromycin (control and gel forms) into the agar before allowing the bacteria to grow in an incubator. Then after each time period, the Petri dishes were incubated at 37° C. for 20 hours to promote bacteria growth in the agar. We observed that not only did the sideromycin YML-1-60 retain activity, but the zones of inhibition increased dramatically after each day. From these results it is believed that the sideromycin is stable and continuously diffuses out of the gel and into the agar over several days while effectively inhibiting bacterial growth. The study has been extended to as long as 168 hours (one week) with retention of antibiotic effectiveness.

FIG. 10 presents gel studies.

As a further demonstration and to mimic application to a wound surface, the gel and YML-1-60 impregnated gel were separately streaked/swabbed onto the surface of a Petri dish that had been inoculated with the same strain of *A. baumannii* and incubated at 37° C. under the standard conditions. As shown in FIG. 11, no bacterial growth inhibition was induced by the gel alone, but the sideromycin impregnated gel induced clear inhibition. These results suggest that sideromycin gels may provide effective controlled release antibiotic delivery systems for the topical treatment of MDRO infected wounds.

FIG. 11 presents structure and gel studies.

Encouraged by the success with *A. baumannii* and sideromycin YML-1-60, described above and shown in FIG. 11, we extended the studies to *P. aeruginosa* using the ampicillin conjugate YML-1-62 and its prodrug (acetyl protected) form YML-1-18, described in Example 4. It is important to recall that the antibiotic components of the conjugates (ampicillin in YML-1-62 and loracarbef in YML-1-60) themselves have no activity against the targeted bacteria. In studies with *P. aeruginosa* KW799 wild type, it was surprising to find that not only are the sideromycins and sideromycin-containing hydrogels potently active against *P. aeruginosa*, but are stable over a multi-day incubation period while demonstrating continuously increased zones of inhibition. See FIG. 12.

FIG. 12 shows multi-day studies Extended studies with additional strains of *Pseudomonas* (Pa01, Pa4, and even Pa-DA1304, the clinical isolate from a cystic fibrosis patient) gave results (data not shown) that were essentially the same as shown above for *P. aeruginosa* KW799/wt.

Thus, we have successfully demonstrated proof of principle for sideromycins and their antibacterial activity with and without gel impregnation.

Example 4 Section 5:

Scale up of YML-I-60 for extended hydrogel and animal burn wound model studies:

Because of the outstanding activity of YML-I-60, itself and as formulated in the hydrogel, we focused on scaling up the synthesis for the next two studies: 1. Detailed studies of the kinetics of release from the hydrogel. 30 mg YML-I-60 were prepared for a full study on gel absorption and release kinetics.

2. Initiation of the first animal burn wound model studies. The first studies will use the rat model described and, if promising, will advance to, the swine burn wound model study. The studies will require several hundred mg of compound, and we now have synthesized, purified, fully characterized and confirmed the activity of a new lot (more than 1 gram) of YML-I-60.

Additional antibacterial studies of YML-I-62:

As illustrated by the data shown in Table 5, the carbacephalosporin conjugate YML-I-60 and its analogous ampicillin conjugate YML-I-62, have potent activity against *Acinetobacter baumannii* and against most strains of *Pseudomonas aeruginosa* (Pa). However, as also shown in Table 5, YML-I-62 was not active (MIC>100 µM) against strain Pa6. We have determined that Pa6 is a beta-lactamase producer so, as expected, being an ampicillin conjugate, YML-I-60, is deactivated by the beta-lactamase. To counter that problem, we retested it in the presence of potassium clavulanate, a known beta-lactamase inhibitor. With the added inhibitor the MIC changed from >100 µM to 0.0625 µM. Thus, the combination of YML-I-62 and clavulanic acid is extremely potent against the highly virulent strain Pa6. This is especially notable since augmentin, the marketed combination of amoxicillin (a penicillin) and clavulanic acid (a beta-lactamase inhibitor) is not active against *Pseudomonas*, because the amoxicillin antibiotic either cannot permeate the Gram-negative outer membrane or/and is susceptible to efflux.

Syntheses and antibacterial studies of an expanded set of mixed ligand siderophore-antibiotic conjugates:

Described is the synthesis of mixed catechol and hydroxamate containing siderophore—antibiotic conjugates to target *Acinetobacter baumannii*. As described earlier (see Scheme 8), we repeated the synthesis of the conjugate of a bis-catechol, mono-hydroxamate loracarbef (carbacephalosporin) (MG-I-112) and confirmed its activity against A. baumanni. The synthesis of the siderophore components was optimized (see Schemes 14 and 15). The improved syntheses allowed us to prepare additional quantities of the initial conjugate, now labeled as new lot MG-I-189/MG-I-112. With the details of the chemistry, purification and characterization worked out, we extended the chemistry to preparation of four additional conjugates. The structures of these five mixed ligand sideromycins are shown below.

Scheme 18. Five mixed ligand sideromycins.
Bis-catechol monohydroxamate conjugates
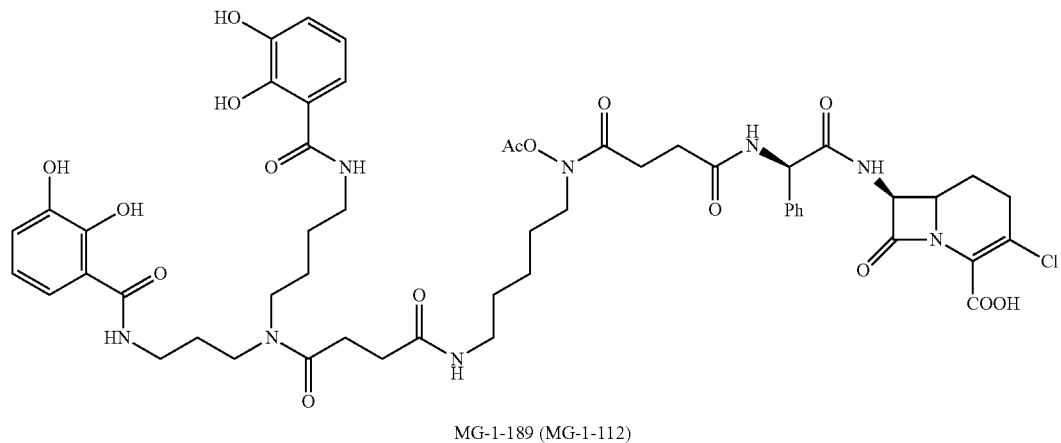
MG-1-189 (MG-1-112)
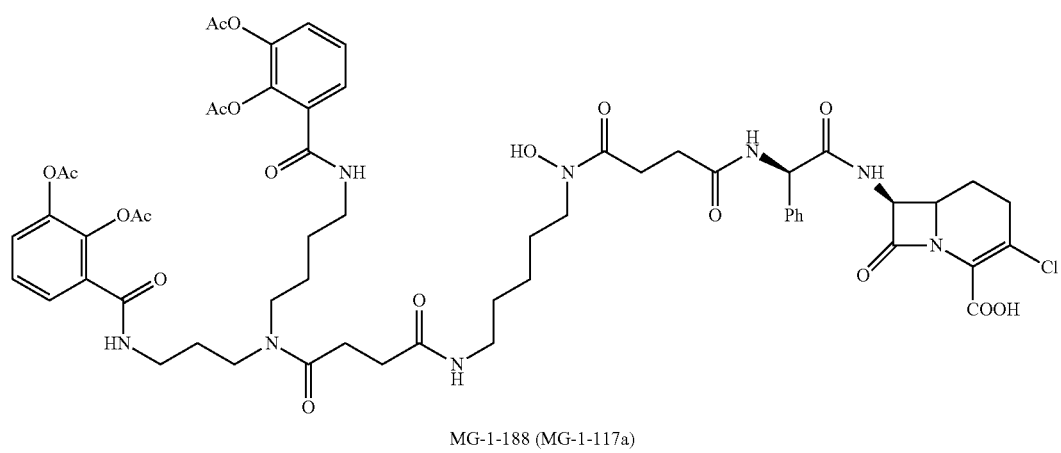
MG-1-188 (MG-1-117a)
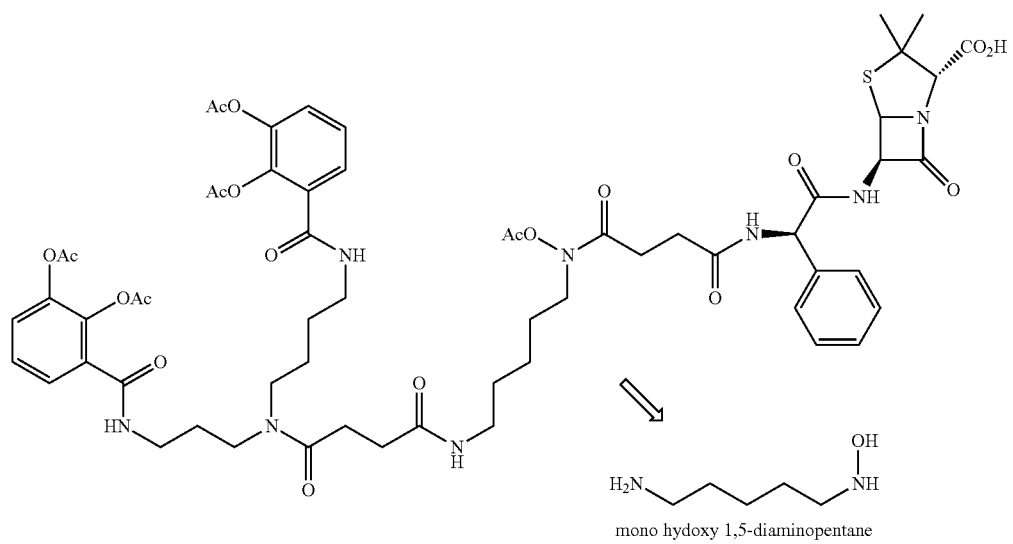
mono hydoxy 1,5-diaminopentane
MG-1-121

-continued
Bis-catechol amino acid based monohydroxamate conjugates

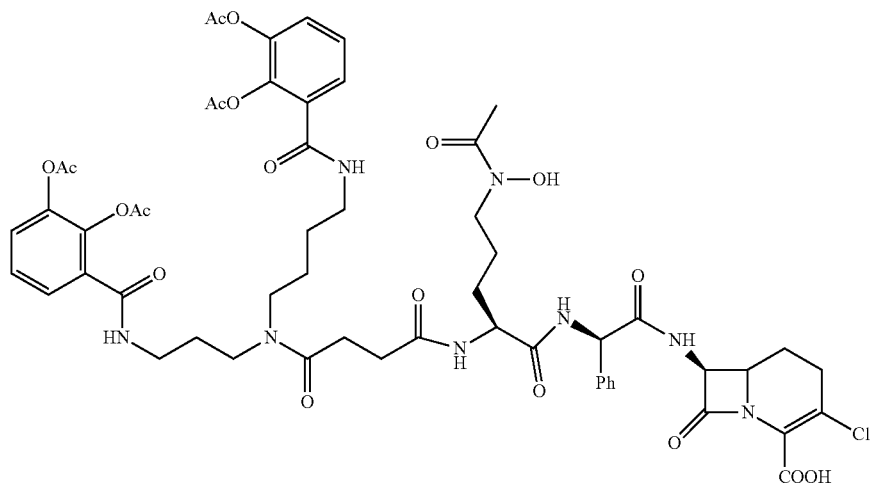

MG-1-185

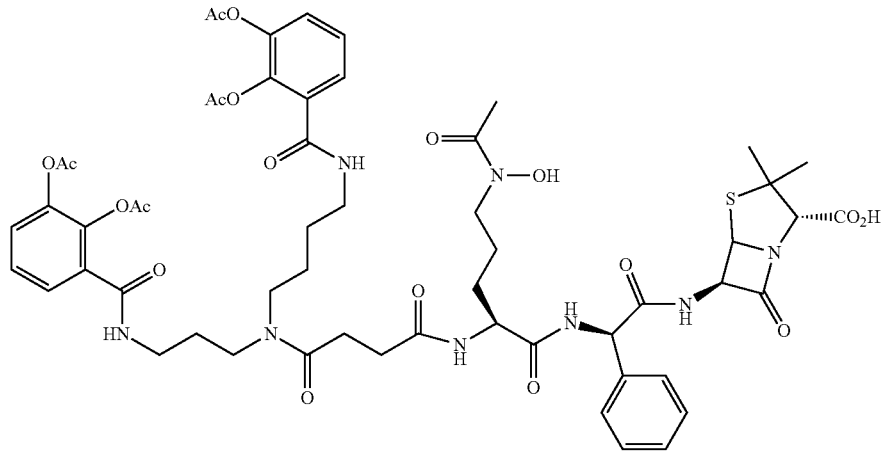

MG-1-186

⇩

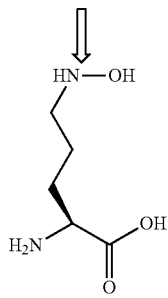

δ-N-hydroxy-L-ornithine

The set of mixed ligand-antibiotic conjugates (mixed ligand sideromycins) is based on the bis-catechol triamine core, but appended with either of two types of hydroxamic acids to complete the mixed ligand system capable of binding iron (III) stoichiometrically. As shown in the structures above, one of the hydroxamates is derived from simple, non-chiral N-hydroxy diamino pentane (as in MG-1-121, 188 & 189) and the other is derived from δ-N-hydroxy-L-ornithine (as in MG-1-185 &186). The latter introduces chirality in the iron binding siderophore. Both of these types of hydroxamic acids are components of a number of natural siderophores.

As shown in Table 6, below, all of the synthetic mixed ligand sideromycins had notable activity against *Acinetobacter* baumanni, perhaps reflecting their structural similarity to fimsbactin, the natural mixed ligand siderophore biosynthesized and utilized selectively by *Acinetobacter* baumanni. Interestingly, the loracarbef conjugates of either type of mixed ligand siderophore were less active against strains of *Pseudomonas* relative to the ampicillin conjugates which were very active (sub micromolar).

TABLE 6

Antibacterial assay results for synthetic siderophore-antibiotic (synthetic sideromycins) prepared and studied in Example 4 Section 5. MIC data given in μM.

| Compound | Pa01 | Pa KW799/wt | Pa4 | Pa6 | Pa-Da-1304 | A. baumannii |
|---|---|---|---|---|---|---|
| MG-1-121 | 0.39-0.55 | 0.14-0.2 | <25 & >0.2 | >50 | <25 & >3 | <12.5 & >0.78 |
| MG-1-185 | >50 | 1.56 | >50 | >50 | >50 | 0.2 |
| MG-1-186 | <25 & >0.2-0.4 | <50 & >0.1 | <50 & >0.4 | >50 | <50 & >0.4 | <12.5 & >0.8 |
| MG-1-188 | >50 | >50 | >50 | >50 | >50 | 0.2 |
| MG-1-189 | >50 | >50 | >50 | >50 | >50 | 0.05 |

Example 4 Section 6:

Scale up syntheses:

Because of the successful demonstration of targeted antibacterial activity of our bis catechol sideromycins and mixed ligand (bis-catechol, mono-hydroxamate), we have designed improved synthesis of the bis-catechol siderophore mimic and the alkylaminohydroxamate components and initiated scale up syntheses (500 grams and 100 grams, respectively) using the schemes shown below.

Scheme 19. Scale up syntheses of bis-catechol and monohydroxamate siderophore component.

Suggested new and shorter route:

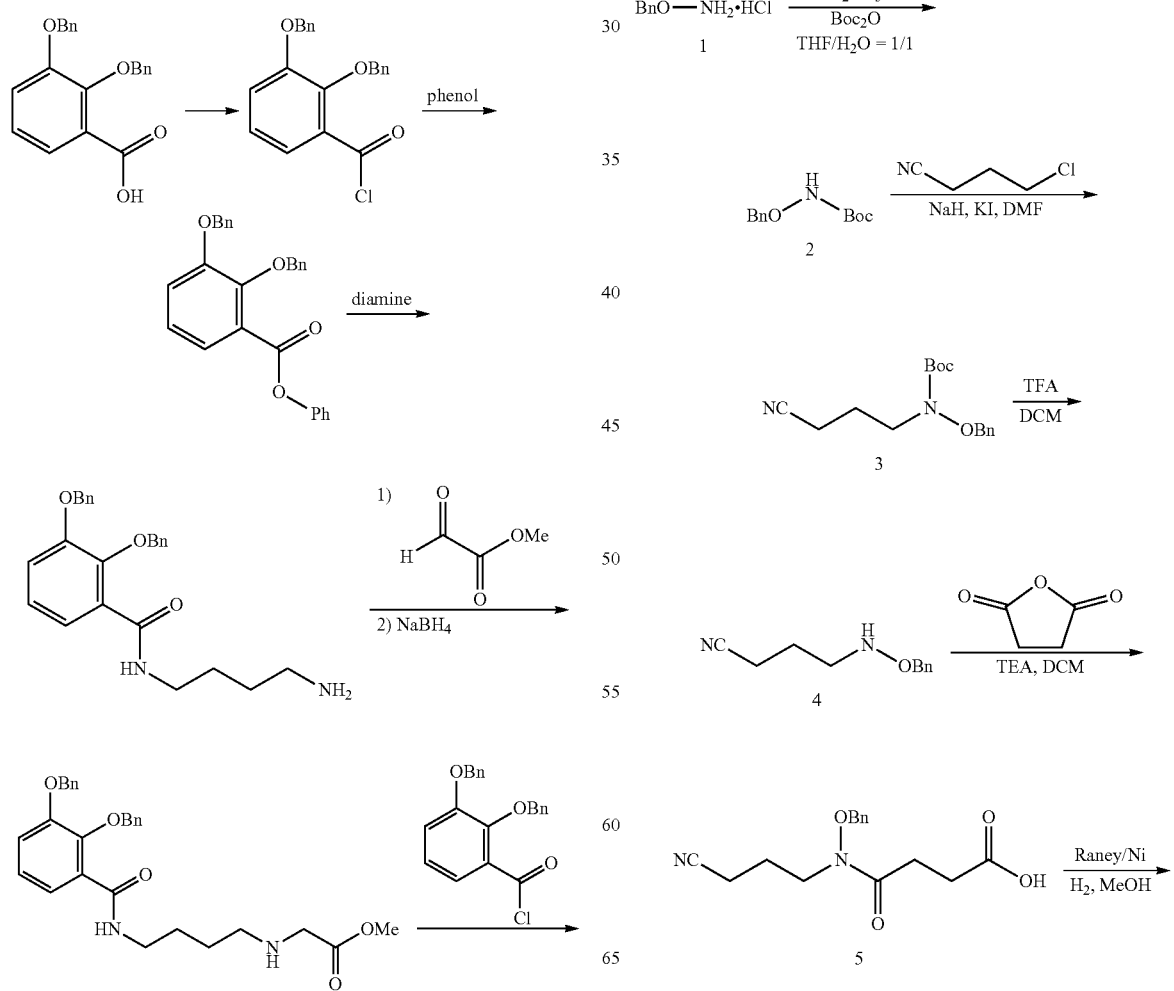

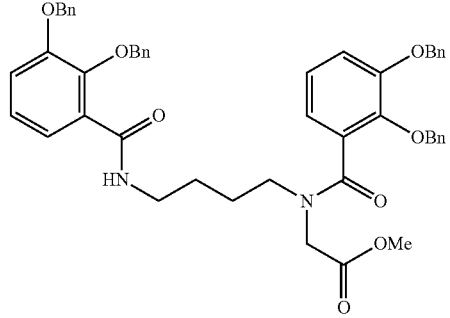

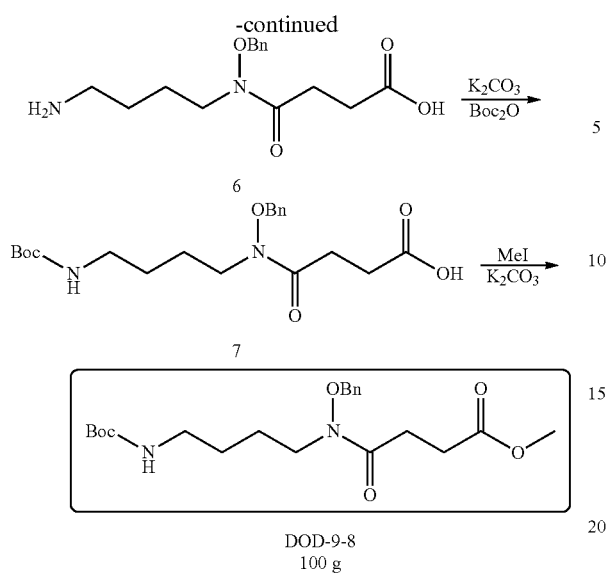

DOD-9-8
100 g

Samples and protocols:

We selected an additional set of compounds for screening in the hydrogel release studies. The compounds, shown below, both sideromycins and control antibiotic components, along with the earlier sample of YML-1-60, have been selected along with a set of bacterial strains and protocols used for assays in our labs that were used in the antibacterial studies described previously.

Selected were the following:

1. Sideromycins: YML-I-62 (ampicillin conjugate), YML-I-91 (loracarbef conjugate YML-I-60), YML-I-109 (cefaclor conjugate), and ampicillin, loracarbef and cefaclor as controls.

2. Bacteria types and activity:

TABLE 7

| Organism | MIC YML-1-62 ampicillin conjugate | MIC YML-1-91 loracarbef conjugate | MIC YML-1-109 cefaclor conjugate | MIC ampicillin | MIC loracarbef | MIC cefaclor |
|---|---|---|---|---|---|---|
| *Pseudomonas aeruginosa* 01 | 0.025 µM | 0.25 µM | 1.56 µM | >200 µM | >200 µM | >50 µM |
| *Pseudomonas aeruginosa* KW799/wt | 0.025 µM | 0.05 µM | 0.05 µM | >200 µM | >200 µM | >50 µM |
| *Acinetobacter baumannii* ATCC 17961 | 0.25 µM | 0.1 µM | 0.05 µM | >200 µM | >200 µM | >50 µM |

3. Updated protocols for anti-bacterial assays

As noted, a new cefaclor conjugate, YML-1-109, which, as shown in the table above has activity comparable to the loracarbef conjugate YML-1-91. We expected that the cefaclor and loracarbef conjugates should have similar activity since the antibiotic components also have essentially the same bacterial target. However, cefaclor is more readily available and less expensive than loracarbef. One concern was that the presence of the sulfur in cefaclor (absent in loracarbef) would create a challenge during the syntheses. However, as shown in the scheme below, the bis-catechol conjugate was synthesized. As shown in the table above, this cefaclor conjugate has excellent activity, comparable to that of the previous loracarbef conjugate against strains of *Pseudomonas* and *Acinetobacter* tested.

Scheme 20. Synthesis of new cefaclor-containing sideromycin YML-1-109.

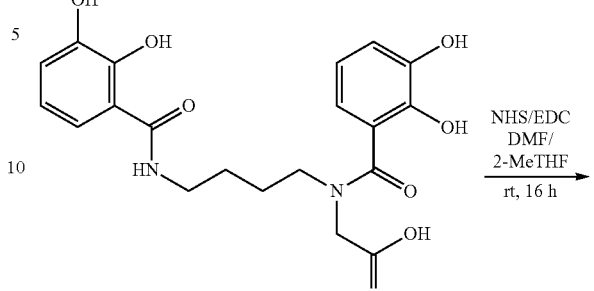

-continued

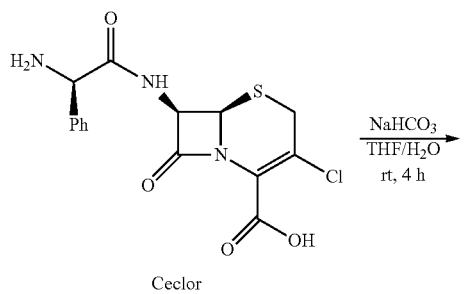

Ceclor

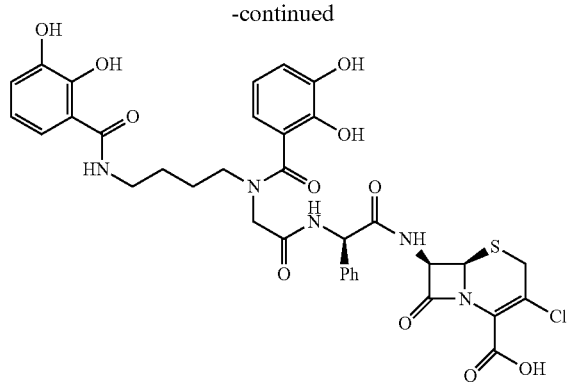

YML-I-109,
Product characterized by
H NMR and LC/MS

Table 6 presents antibacterial assay results of additional mixed ligand sideromycins with a common bis-catechol core and two types of hydroxamates (linear, as in loracarbef conjugate MG-1-189/112, the acetylated derivative MG-1-188/117a, and acetylated ampicillin analog MG-1-121, and the ornithine amino acid based analogs, partially acetylated loracarbef conjugate MG-1-185, and ampicillin conjugate MG-1-186). The initial antibacterial assay shown in Table 6 indicated activity against select strains of *Pseudomonas* and/or *Acinetobacter*. However, the reduction of activity at higher concentrations but excellent activity at lower, drug like concentrations, raised the concern that either the conjugates were unstable or some of the siderophore component remained in the final conjugate and at higher concentrations, the siderophore growth promotion would compete for the sideromycin growth inhibition. The possible instability was considered to be due to the presence of the short succinate linker that upon bacterial uptake and iron removal would promote intramolecular release of the antibiotic component and regeneration of the siderophore with subsequent growth promotion effects. Two studies were initiated to address this result. First, meticulous LC/MS studies indicated that the mixed ligand sideromycins did contain additional siderophore component but whether this was due to incomplete purification or instability needed to be ascertained. Meanwhile, the assays were repeated with intentional addition (titration with) of the siderophore component itself to the sideromycins. The assays revealed that, as expected, the additional siderophore competed for active transport with the sideromycin and created the "window" effect of apparent less activity at higher concentration and excellent activity at lower concentration of sideromycin (and thus, also siderophore component). Therefore, each of these mixed ligand sideromycins has been resynthesized and rigorously purified. Purity has been confirmed by extensive LC/MS and NMR studies that indicate that the samples are homogeneous. The mixed ligand conjugates were also incubated in media under conditions that mimic the antibacterial assays that demonstrated that the deacetylated sideromycins, such as MG-1-189, are perfectly stable, whereas, and as expected, the acetylated analogs slowly lose the acetyl "protecting" groups, as they should since they were designed to be prodrugs. MIC antibacterial assays are being repeated with the newly prepared samples. However, with the stability of MG-1-189, demonstrated, we performed a time release agar diffusion antibacterial study against *Acinetobacter* and, as with YML-1-60, found a persistent increase in zone of inhibition over four days with no growth in the inhibition zones after more than a week. Thus, the mixed ligand system has the potential to be a very potent and selective anti-*Acinetobacter* sideromycin. The mixed ligand ampicillin conjugate MG-1-121 was also resynthesized and rigorously purified to give a new lot (MG-1-239) which, based on the usual antibacterial assays shows consistent potent activity against select strains of *P. aeruginosa* (Pa01, 0.2 μM & PaKW799/wt 0.05 μM).

The second control was designed in which the succinate linker was synthetically replaced with a glutarate, which has an extra methylene spacer that would minimize intramolecular antibiotic, release mechanisms with concomitant generation of the siderophore component; The successful syntheses were similar to those used for the succinate derivatives and, final conjugation steps are shown below. Thus, we have prepared new mixed ligand sideromycins with glutamate linkers and ampicillin, loracarbef and cefaclor as the antibiotic components for direct comparison to the previous succinate analogs. Both the ampicillin and cefaclor conjugates were also prepared in the acetylated (prodrug) forms for parallel studies. Rigorous analyses indicate that the free, non-acetylated versions are rigorously pure and stable under the usual assay conditions, as again demonstrated by LC/MS studies.

Scheme 21. Syntheses of new sideromycins with glutarate linkers.

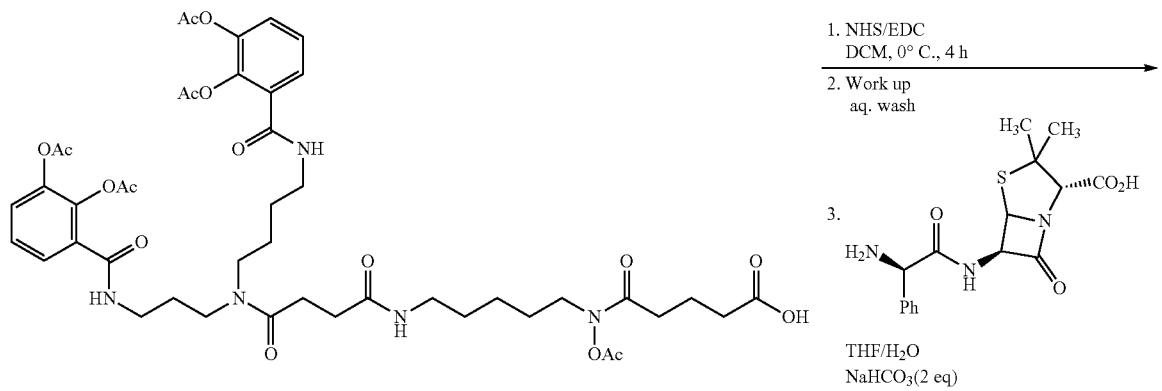

-continued
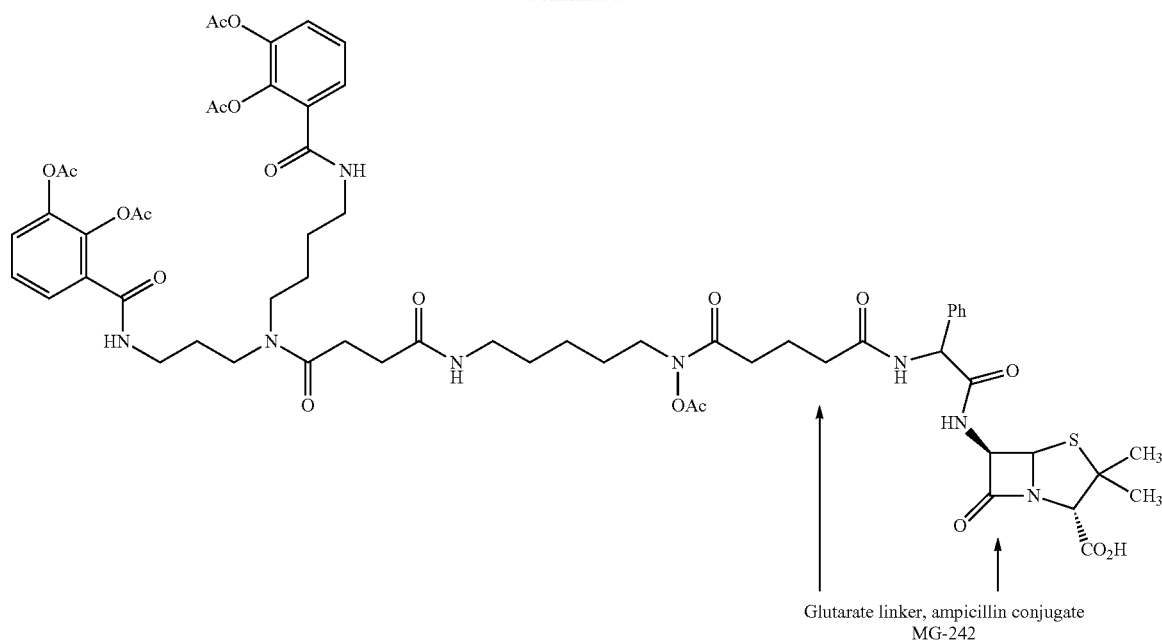
Glutarate linker, ampicillin conjugate
MG-242
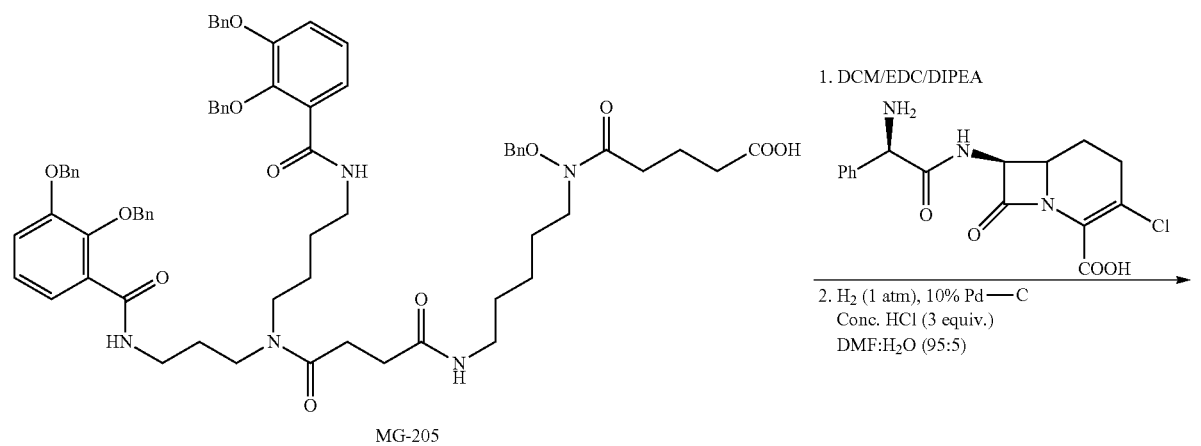
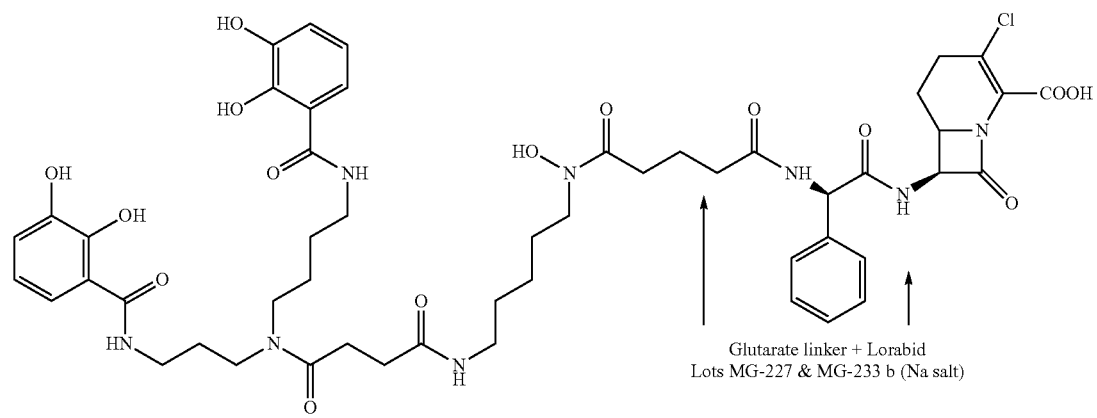
Glutarate linker + Lorabid
Lots MG-227 & MG-233 b (Na salt)

-continued
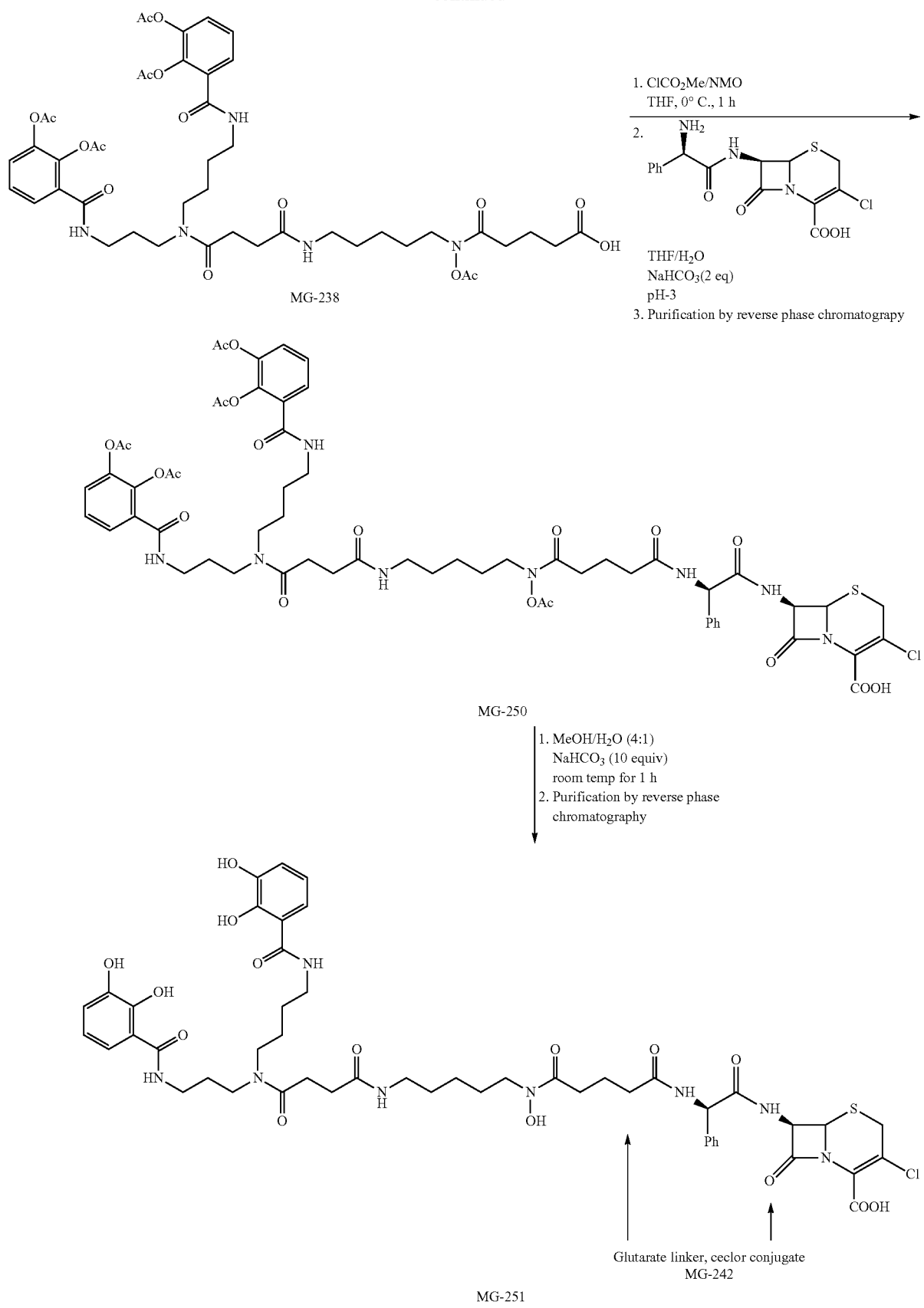

We considered establishing additional siderophore growth promotion and sideromycin growth inhibition studies, as well as providing methods to determine iron binding assays (optimization of the chrome-azural blue (CAS) assay) and siderophore biosynthesis/production assays by targeted bacteria to help continuous identification of optimal siderophore components for extended sideromycin design and syntheses.

Example 4 Section 7:

Scale up syntheses:

We reported an improved design (Scheme 19) for the synthesis of the bis-catechol siderophore mimic used in our active bis-catechol sideromycins and mixed ligand sideromycins. The improved design and scale up resulted in 472.6 grams of this key material. These results emphasize that the important bis-catechol siderophore component will be readily available for future synthetic and biological studies.

Samples and protocols:

Several synthetic sideromycins, antibacterial protocols and strains were selected to begin their assays and to perform gel incorporation and release studies. Studies were initiated on incorporation of sideromycins into hydrogels as summarized below.

Studies related to Specific Mm 2: Sideromycin incorporation into Keratin hydrogels:

This focuses on the formulation of the keratin hydrogel with various sideromycins. Release assays have been performed, quantification methods developed, and bacterial inhibition assay begun.

Methods:

Hydrogel Preparation: Stock solutions of each sideromycin in YML-1-60, YML-1-62, YML-1-91, and YML-1-109 were prepared in DMSO to a concentration of 1M. Solutions were diluted to 2 mM in water. Three-1:10 dilutions of the 2 mM solution were performed to obtain a 0.02 and 0.2 mM solution of each sideromycin.

Keratin was obtained by oxidative extraction of human haft (keratose) and purified by KeraNetics using a patented process in a 21CFR820 validated facility as described previously. The lyophilized extract was weighed using a 95:5 ▢:▢ keratin ratio and hydrated with an aqueous solution containing 2, 0.2, and 0.02 mM sideromycins to achieve a 10% and 15% weight-to-volume ratio. Hydrogels were allowed to equilibrate overnight at 37° C. prior to use.

Drug Release Assay: Two hundred fifty-μl aliquots of the keratin hydrogels containing either 2, 0.2, or 0.02 mM of each sideromycin were placed in microcentrifuge tubes and overlaid with 250 μL of PBS. PBS was collected and replaced with fresh PBS at 1.5, 3, 12, hours, 1, 2, 3, 4, 5, 6, and 7 days. Sampled PBS was analyzed for total protein using a BCA assay. Protein was extracted from 200 μL of each PBS sample by adding 1 mL acetonitrile, vortexing, then spinning for 5=minutes at 14,000 RPM on a table-top microcentifudge. The acetonitrile solution was moved to a fresh tube and placed into a heating block set to 40° C. and nitrogen blown over the sample at 2 mL/min until dry. Samples were resuspended in the mobile phase, listed in HPLC method below, and stored at −20° C. until HPLC analysis could be performed.

WIC Analysis: After a systematic development process looking at no fewer than 6 different columns of various chemistries, mobile phase optimization, and gradient development, a method for quantifying both YML-1-60 and YML-1-90 has been developed. The following conditions will be used to quantify each of the release samples prepared as described above.

Column— Agilent Zorbax SB-C18, 3.5 μm, 4.6×150 mm
Column temp— 50 deg. C.
Flow rate—1.0 mL/min
Mobile phase A—Water+0.1% formic acid
Mobile phase B—Acetonitrile+0.1% formic acid
Gradient Conditions—
0 min 10% B
8 min 100% B
9 min 10% B
10 min 10% B
Injection volume—10 μL
Run time—10 min
Wavelength of detection—254 nm
Retention time—5.3 min Agar Diffusion Inhibition Assay: Overnight cultures of clinical isolates of P. aeruginonsa (ISR14-003 and ISR14-004) were grown in TSB for 18-24 hours and standard suspensions of ~1.5×10$^6$ cfu/mL were prepared in sterile saline solution (0.9% NaCl) according to a $BaSO_4$ 0.5 McFarland Standard. Of this standardized suspension, 0.1 mL was added to 34 mL of sterile, melted, and tempered (47-50 QC) Mueller-Hinton No. 2 agar. After gentle mixing, the inoculated melted agar was poured into a sterile petri dish (145 mm×20 mm, Greiner Bio-One) and allowed to solidify. Wells of 9 mm diameter were cut from the petri dish agar and filled with 100 of the test sample solution. The petri dish was incubated at 37° C. The inhibition zone diameters were measured (mm) with an electronic caliper after 24-48 hours.

Results:

Release and Formulation: Sideromycins are readily soluble in the DMSO/water solutions described in the methods discussion. Keratin hydrogels form spontaneously and upon visual inspection during the week-long release assay, there appears to be behaving in a similar fashion to all other compounds put through the delivery platform. Protein assays for the sample are being quantified. Sideromycin quantification of these samples is in the extraction procedure described above.

The method developed to quantify the sideromycins took the largest portion of the effort. Several different column chemistries were experimented with. All produced either a peak that could not be resolve from the void volume or a peak that showed no concentration dependent response. Peak overlays are shown in FIG. 13-1 for injections made of both YML-1-60 and YML-1-90. Good separation was observed between the void volume and the sideromycins. Peak retention times were approximately 5.4 min. A Dose dependant peak area was also observed and a standard curve of both YML-1-60 and YML-1-90 show in FIGS. 13-2 and 13-3. Standards are prepared using the extraction process-described above for the samples. Linearity on both compounds is greater then 0.99.

FIG. 13-1 shows Peak overlay for both YML-1-60 and YML-1-90

FIG. 13-2 shows Standard curve for YML-1-60. FIG. 13-3. Standard curve for YML-1-90

In some embodiments, incorporation of potassium clavulanate into the hydrogel may be required. Therefore the HPLC method was investigated to determine the ability of the method to resolve both the clavulanate and the sidermycin. As shown in FIG. 13-4, the potassium clavulanate eluted in the void volume while the retention time of the sideromycin is unaltered from the standards.

FIG. 13-4. Retention of potassium clavulanate in YML-1-60

Agar Diffusion Assay: Clinical-isolated of *P. aeruginosa* were obtained from the USAISR to investigate strain-to-strain differences in susceptibility. The results indicate the 2 mM YML-1-90 is able to inhibit the growth of this strain. These results suggest that the strain is a beta-lactamase producing strain and the incorporation of potassium clavulanate will be required for inhibition in the other compounds. Zone of inhibitions statically show zones of approximately 99 mm in either 10 or 15% keratin hydrogel at this sideromycin dose.

Syntheses, antibacterial assays and Formulation studies:

Along with ongoing syntheses and antibacterial assays of sideromycins, we started to study formulation of the final compounds for administration during animal studies to study PK properties, tolerability (toxicity) and efficacy in infection models.

Formulation: Since animal studies require appropriate formulation, we made a water soluble loracarbef conjugate of our bis-catechol siderophore suitable for animal studies. The successful chemistry is shown in Scheme 22 below.

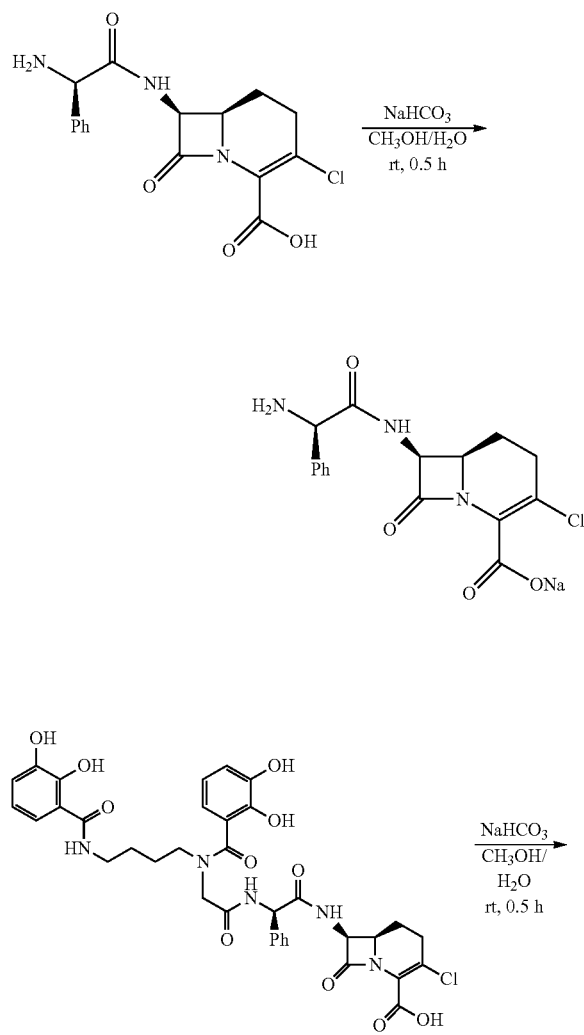

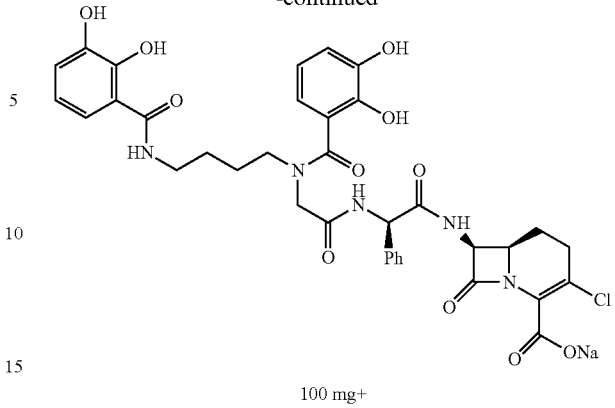

100 mg+

Conversion of the free carboxylic acid to the corresponding sodium salt greatly increased water solubility of both the parent antibiotic (loracarbef) and the sideromycin, which is very important for the initial toxicology studies in mice through IV administration of the compounds.

Animal tolerability studies:

With the easily formulated sideromycin in hand, we profiled sideromycin safety in healthy mice. Thus, sideromycin YML-I-115 was tested in healthy mice to determine its No-observed-adverse-effect level (NOAEL). We dosed the mice with YML-I-115 (the sodium salt) at 1 mg/kg, 20 mg/kg, 50 mg/kg, and 100 mg/kg through IV injection of the compound. All the mice survived and none of the mice experienced abnormal behavior during the 24 hour study. Therefore, the NOAEL of currently at 100 mg/kg, suggesting a very low toxicity of sideromycin YML-I-115. Higher dosage animal experiments have been scheduled to determine the upper limit of the NOAEL value. This initial animal toxicity study suggests that the compound will be safe as a topical medication for wound healing.

At two different time points (2 hours and 24 hours), animals were sacrificed and blood samples are collected for plasma isolation. Freshly collected animal whole blood samples were centrifuged in a refrigerated centrifuge at 2000 g for 15 minutes. The plasma supernatant was isolated using a glass pipette into a labeled Eppendorf tube. Each Eppendorf tube contained about 320 µL of mouse plasma. The plasma samples were stored in a −83° C. freezer until sample extractions could be performed. Plasma samples from the deep freezer were warmed to room temperature. To 320 µL of plasma, was added 960 µL of acetonitrile in the Eppendorf tube, which was then mixed and vortexed for 10 minutes. The Eppendorf tube was centrifuged at 1000 rmp for 5 minutes to precipitate plasma proteins. The supernatant was pipetted out to a glass vial and the solvent was removed using a rotary evaporator. The residue was dissolved in methanol (~3004) and transferred to a small glass vial. The methanol was removed to give a white Solid residue, ready for LC/MS/MS analysis.

Syntheses, resyntheses and scale up Syntheses of mixed ligand conjugates and antibiotic assays alone and in hydrogels.

The cumulative synthetic results, antibacterial assays with and without gel generated additional enthusiasm for more detailed studies of microbe targeted sideromycins. In the current Section, we, describe efforts to scale up, purify and test the previously described mixed ligand sideromycins that are designed to specifically target the MDRO (Multi-Drug Resistant Organisms) described previously. The discussion below describes details which, in summary, indicate that we can scale up the syntheses to practical amounts needed for all studies, including full antibacterial assays, gel studies and ample quantities for animal studies. The results are presented in full detail to emphasize the effort that was required, but is now successful.

A. Synthesis, Scale-up, and Biological Studies of mixed ligand-loracarbef conjugate with asuccinate linker (8), MG-1-112/MG-1-189/MG-1-281.

The mixed ligand-loracarbef (carbacephalosporin) conjugate with a succinate linker, MG-1-112/MG-1-189/MG-1-281, showed remarkable 'selective' activity against *Acinetobacter* baumanni ATCC 17961: MIC 0.05 µM, 0.025 µM (MG-1-281). Compared to ampicillin conjugates, this loracarbef conjugate displayed minimal activity against *Pseudomonas aeruginosa*: Pa01; Pa KW799/Wt; Pa4; Pa6; Pa-Da-1304: MIC>50 µM. However, with the stability of MG-1-189 demonstrated, we performed a timed release agar diffusion antibacterial study against *Acinetobacter* and, just as in the earlier studies with YML-1-60, found a persistent increase in zone of inhibition over four days with no growth in the inhibition zones after more than a week (FIG. 13-5).

FIG. 13-5. *A. baumannii* ATCC 17961+MG-1-189 time study for 96 h.

Interestingly, MG-1-189 did not show any toxicity in Cytotoxicity assay: PC3 MCF7; Hela: IC50 >20 µM.

TABLE 8

Antibacterial activity of MG-1-189 and sulbactam on different strains of *A. baumannii*.

| cmpds | *A. baumannii* BAA1710 | *A. baumannii* BAA1793 | *A. baumannii* BAA1797 | *A. baumannii* BAA1800 |
|---|---|---|---|---|
| MG-189 + sulbactam | 1.56 µM MG-189 + 0.6 µg/ml sulbactam | 0.78 µM MG-189 + 0.3 µg/ml sulbactam | 1.56 µM MG-189 + 0.6 µg/ml sulbactam | 0.78 µM MG-189 + 0.3 µg/ml sulbactam |
| MG-189 + sulbactam | 1.56 µM MG-189 + 0.6 µg/ml sulbactam | 0.78 µM MG-189 + 0.3 µg/ml sulbactam | 1.56 µM MG-189 + 0.6 µg/ml sulbactam | 0.78 µM MG-189 + 0.3 µg/ml sulbactam |
| sulbactam | 2.5 µg/ml | 1.25 µg/ml | 1.25 µg/ml | 1.25 µg/ml |
| MG-189 | >25 µM | >25 µM | >25 µM | >25 µM |
| loracarbef | >25 µM | >25 µM | >25 µM | >25 µM |
| loracarbef + sulbactam | 2.5 µg/ml | 1.25 µg/ml | 1.25 µg/ml | 1.25 µg/ml |
| amikacin | 32 µg/ml | 32 µg/ml | 64 µg/ml | 64 µg/ml |

For the hydrogel study, MG-1-189/281 was resynthesized following the synthetic scheme below (Scheme 23).

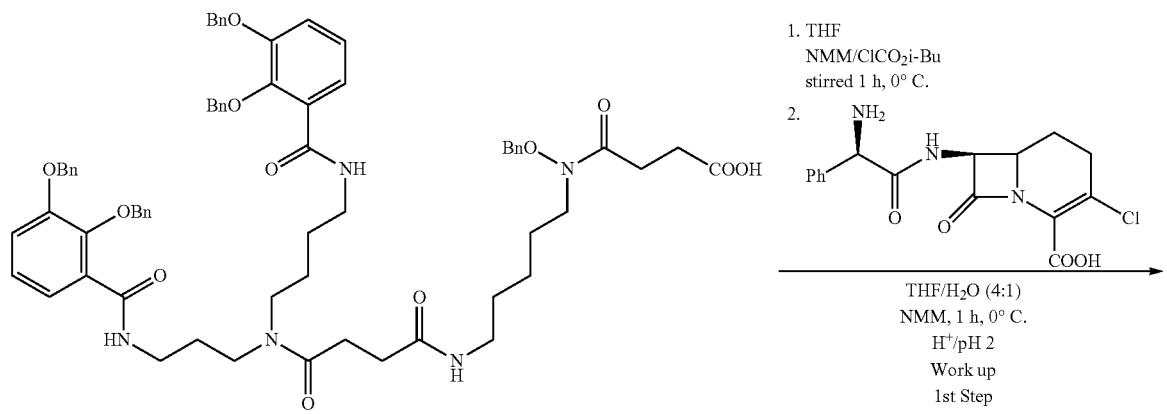

Scheme 23.

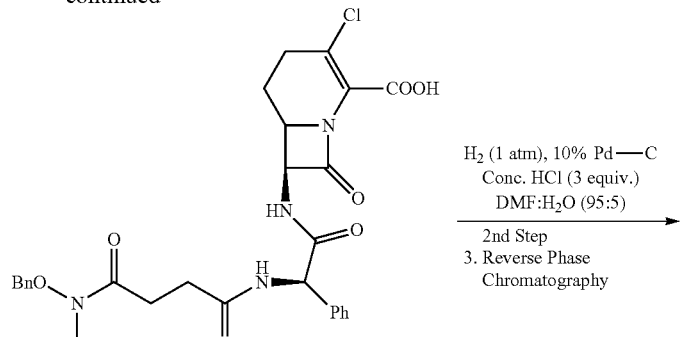
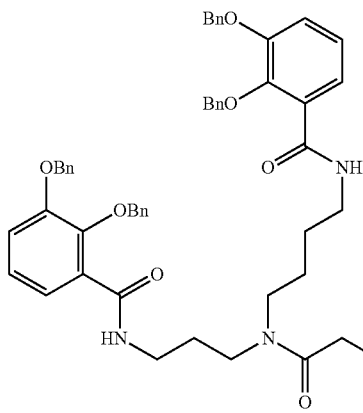

2, MG-1-257

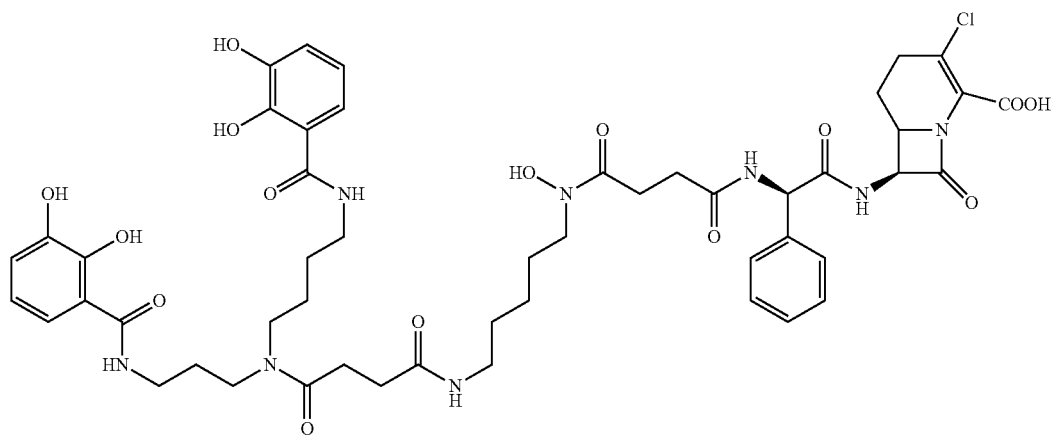

3a, MG-1-112
3b, MG-1-189
3c, MG-1-281

A relatively lower (40%) yield during scale up synthesis was attributed to the interference of the free carboxylate function of loracarbef as well as problem during hydrogenolytic removal of OBn group using aq. DMF under acidic conditions. Therefore, we will resynthesize the compound with TBDMS protection of the mixed ligand siderophore, following the scheme below (Scheme 24), following a protocol that we recently developed and successfully used for the synthesis of the mixed ligand glutaryl cefaclor conjugate (MG-1-277/285) detailed later herein. We will obtain the corresponding TBDMS-protected mixed ligand siderophore (4, P=TBDMS in Scheme 24).

Scheme 24.

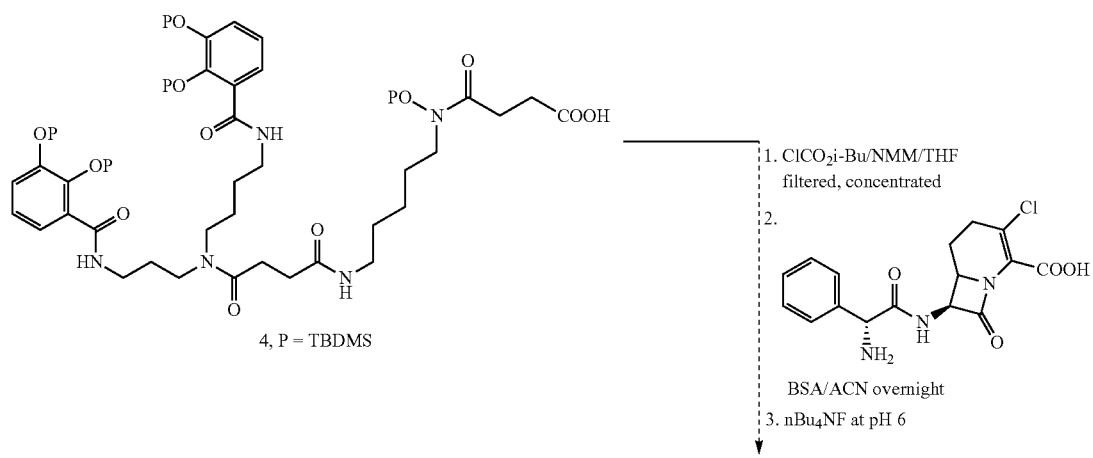

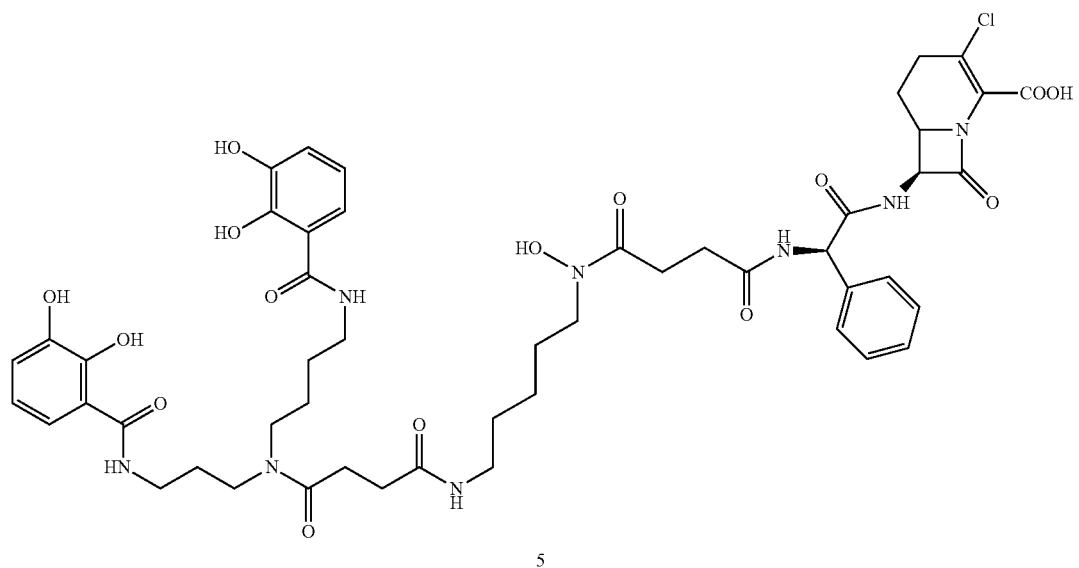

B. Synthesis of mixed ligand-loracarbef conjugate with glutarate (3-carbon) linker MG-1-227/MG-1-233b:

We designed the syntheses of the mixed ligand-loracarbef conjugates with both succinate (2-carbon) and glutarate (3-carbon) linkers in order to determine the effect of linker-flexibility on the stability that, in turn, should contribute to the PK properties and in vivo efficacy of the sideromycins. The synthesis of mixed ligand-loracarbef conjugate with glutarate (3-carbon) linker, 8, MG-1-227 and MG-1-233b, was accomplished following the chemical sequence shown in Scheme 25.

Scheme 25.
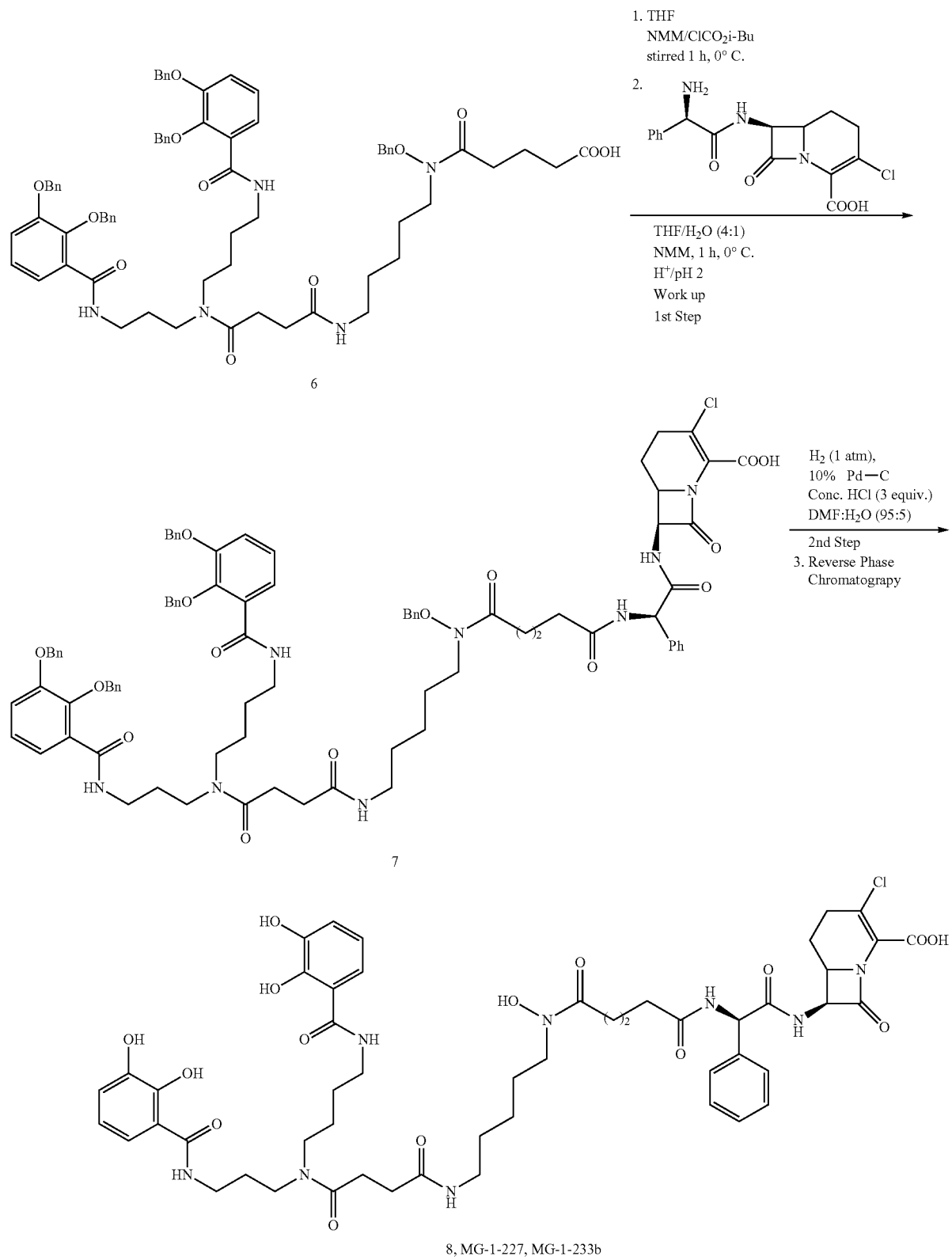
MG-1-227/MG-1-233b showed minimal activity against *Pseudomonas aeruginosa* Pa KW799/Wt: MIC 0.2 μM; Pa4; Pa6; Pa-Da-1304: MIC>50 μM and, as planned and anticipated, showed selective activity against *Acinetobacter* baumanni ATCC 17961: MIC 0.025 μM. The conjugate showed no toxicity in Cytotoxicity assay, $IC_{50}$ (μM): PC3 (15); MCF7 (11); Hela (>20), and showed the desired stability in the stability assay.

C. Synthesis and scale-up of mixed ligand-cefaclor conjugate with a 2-carbon (succinate) linker (13), MG-1-237b:

Since loracarbef is less available than its sulfur analog, cefaclor, we wanted to make conjugate of another cephalosporin derivative (cefaclor) to see if the desired antibacterial activity could be retained. Once again, the mixed ligand-cefaclor conjugate, MG-237b, showed 'selective' antibacterial activity against *Acinetobacter* baumanni ATCC 17961: MIC <0.025 μM and minimal activity against *Pseudomonas aeruginosa* Pa01; Pa KW799/Wt; Pa4; Pa6; Pa-Da-1304: MIC >50 μM.

The mixed ligand-cefaclor conjugate, MG-1-237b, has also been considered for gel studies.

For scale up synthesis of MG-1-237b we will be using the synthetic scheme shown below (Scheme 26).

123 124
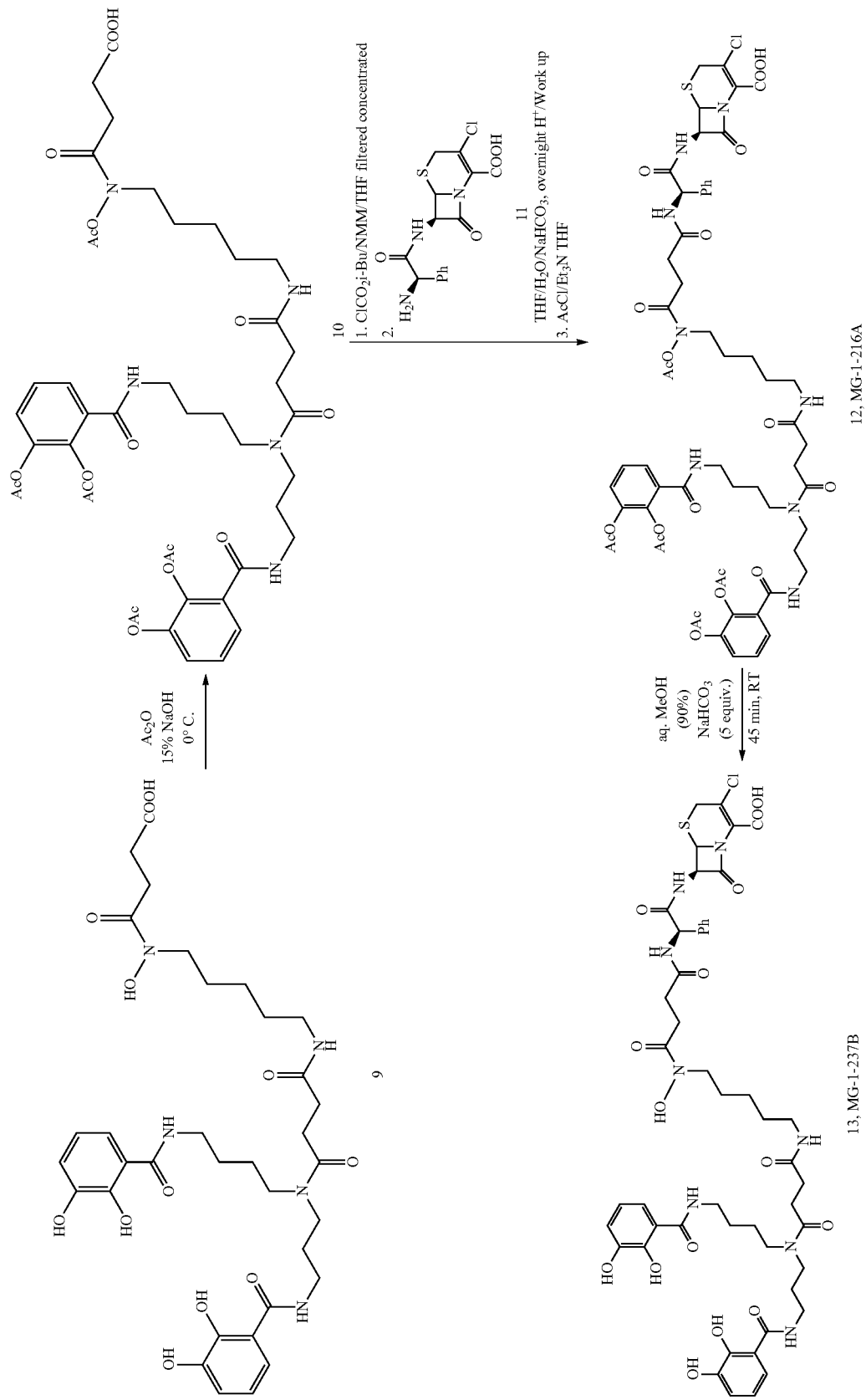
Scheme 26.

D. Synthesis of mixed ligand-cefaclor conjugate with a glutarate (3-carbon) linker MG-1-285, MG-1-299.

The mixed ligand-cefaclor conjugate with glutarate (3-carbon)linker, MG-1-285, showed excellent potency and highly selective activity against *Acinetobacter* baumanni ATCC 17961: MIC 0.025 µM.

Development of a New Method for Scale up synthesis of Conjugates: A new protocol involving the TBDMS protection of catechol/hydroxamate hydroxyl groups proved superior compared to previously described benzyl or acetyl protection protocols. For tox, in vivo antibacterial assay and PK studies, we made a 400 mg batch of the mixed ligand-cefaclor conjugate with a glutarate (3-carbon) Further purification of this batch has been completed, which should provide sufficient quantities of the conjugate for sodium salt formation and formulation for tox studies and gel studies. This chemistry is reproducible and very straight forward.

Scheme 27 shows a synthesis using the corresponding TBDMS-protected mixed ligand siderophore (15, P=TBDMS, MG-1-265).

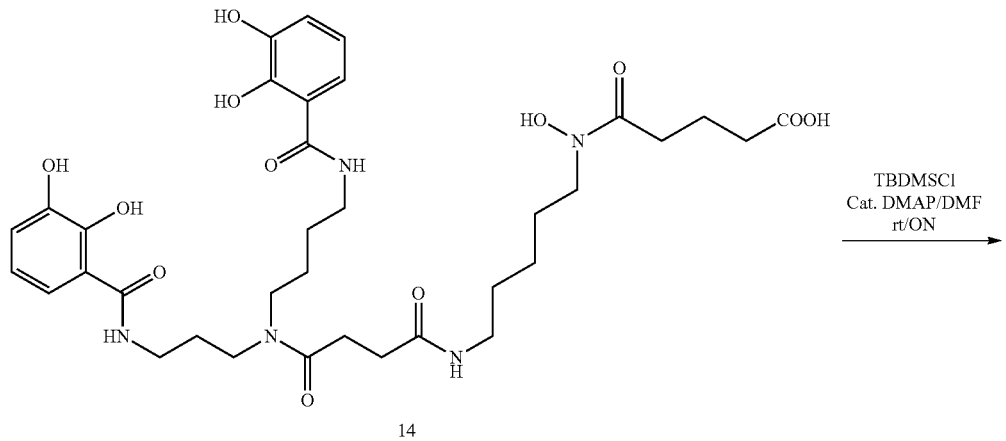

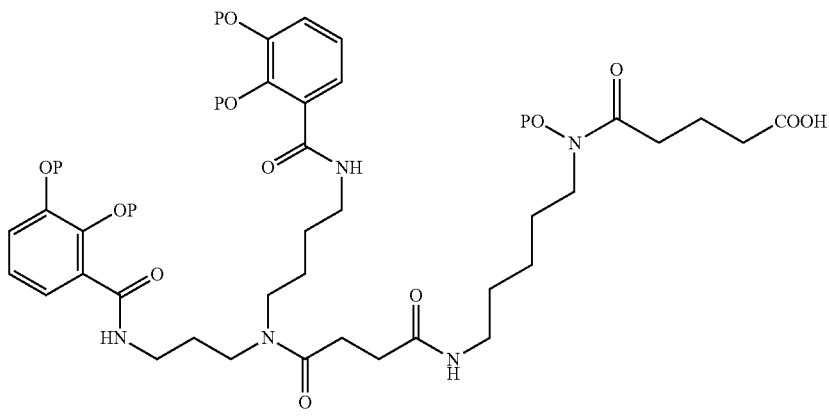

-continued

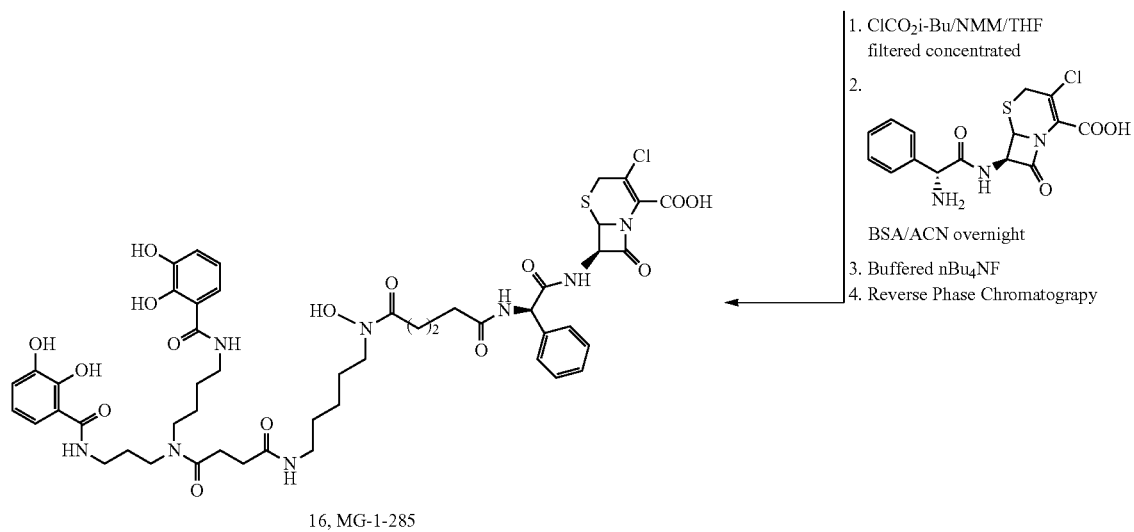

16, MG-1-285

E. Synthesis of acetate-proteced mixed ligand ampicillin conjugate, MG-1-121/MG-1-239, and deacetylated ampicillin conjugate, MG-1-294, with a succinate (2-carbon) linker.

The acetate-protected mixed ligand ampicillin conjugate MG-1-121 (MG-1-239) demonstrated a broad spectrum activity against Gram-negative bacteria tested.

*Pseudomonas aeruginosa* MIC (01): Pa01 (0.39-0.55); Pa KW799/Wt (0.14-0.2); Pa4 (<25 & >0.2); Pa-Da-1304 (>50), and *Acinetobacter baumannii* MIC (µM): ATCC 17961 (<12.5 & >0.78)

A stability assay in media showed expected loss of acetyl groups (prodrug), and in a cytotoxicity assay the compounds were clean (PC3; MCF7; Hela: IC50 >20 µM).

Scheme 28.

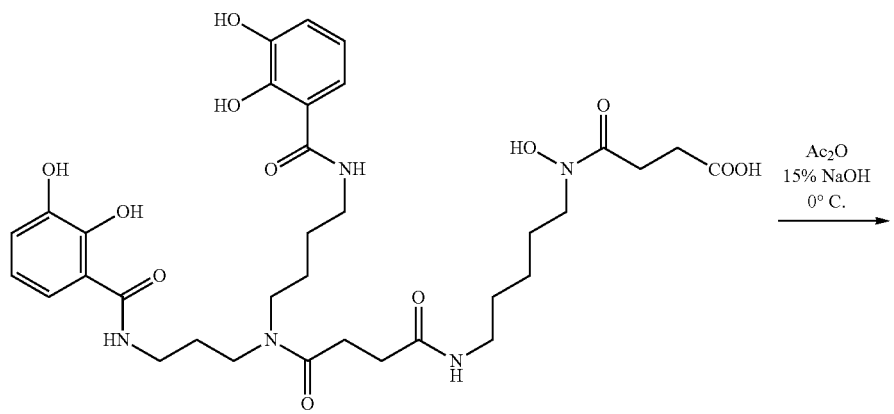

17

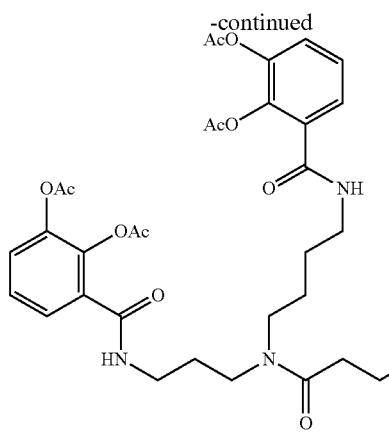

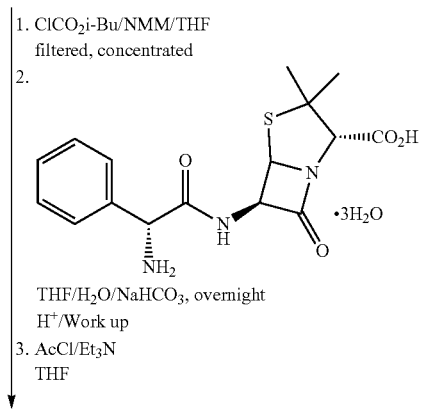

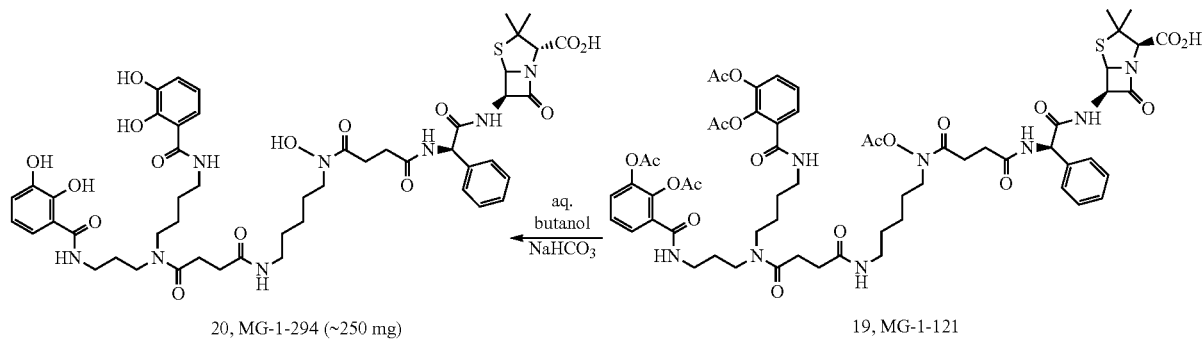

For scale up of MG-1-294, we will use the TBDMS protection protocol described above.

F. Synthesis of Mixed ligand-ampicillin conjugate with glutarate (3-carbon) linker (22), MG-1-13:

As described earlier, the Mixed Ligand loracarbef conjugate with a 3-carbon (glutarate) linker (MG-1-285) showed antibacterial activity against *Acinetobacter baumannii* with excellent MICs (0.025 µM.) and good selectivity for *Acinetobacter*. Encouraged by this result we designed the synthesis of the corresponding ampicillin conjugate with the same glutaryl-modification of the siderophore (Scheme 29). This batch of conjugate 22, MG-2-13, will be used for in vitro antibacterial studies and also for gel studies. As observed for. MG-1-121, conjugate MG-2-13 is expected to show similar broad spectrum activity. However, pending the results from the in vitro screening, we plan a scale up synthesis of MG-2-13 for other studies, e.g., tox, in vivo efficacy and PK studies.

Scheme 29.

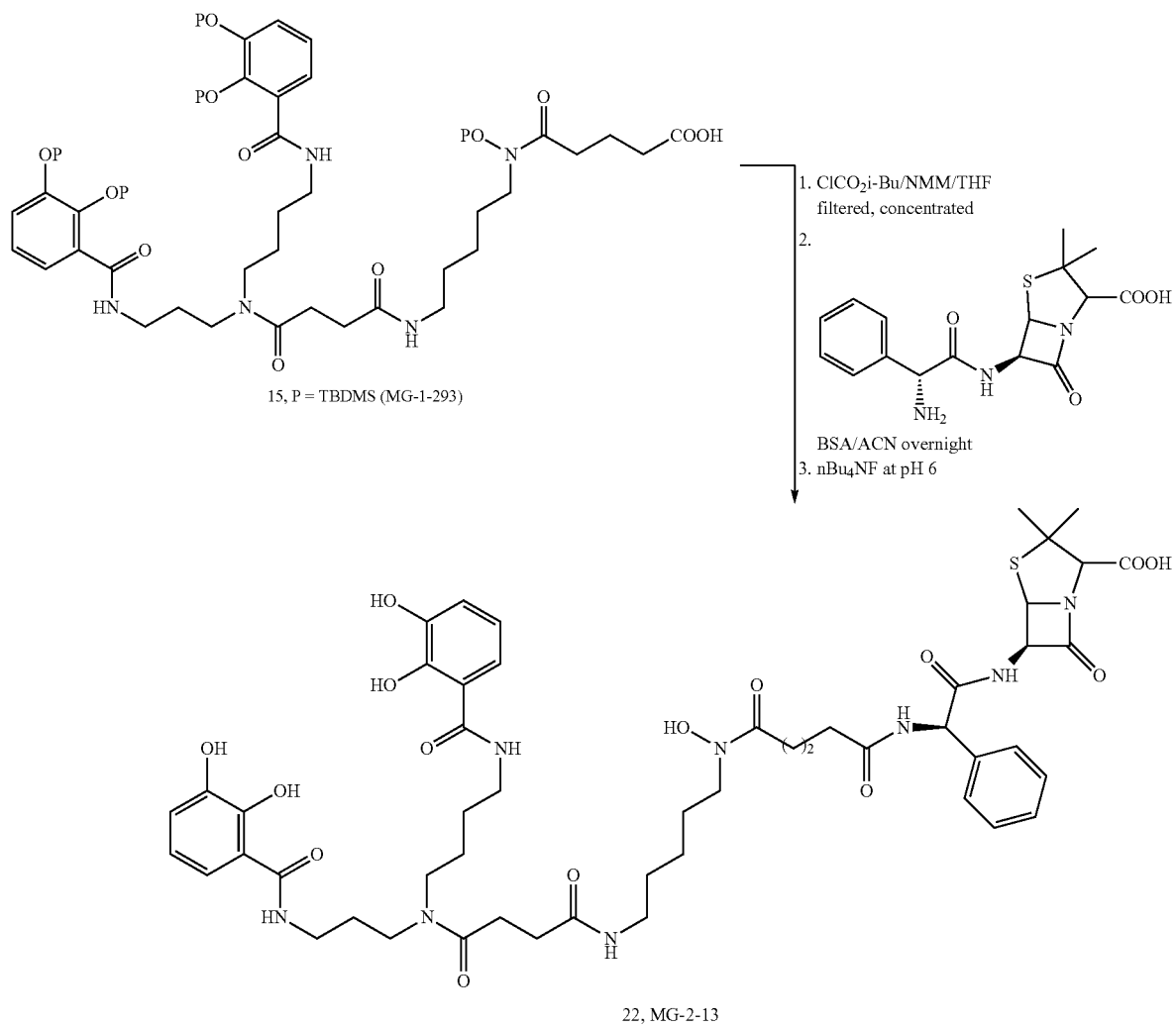

In vivo data

Murine Survival Experiment with *Acinetobacter*

FIG. 14 shows graphically the in-viva data for murine survival experiments with *acinetobacter* (See also Table 9).

In vivo data for murine survival with *Acinetobacter* is shown in Table 9 below and graphically in FIG. 14. In the experiments, $10^8$ *Acinetobacter* was administered IP at time 0 on Day 1, and antibiotic was administered twice IV at +30 min and +4 hr

TABLE 9

|  | D 1 | D 2 | D 3 | D 4 | D 5 | D 6 | D 7 |
|---|---|---|---|---|---|---|---|
| YML-115 250 mg/kg | 6.1 | 6.1 | 6.1 | 6.1 | 6.1 | 6.1 | 6.1 |
| YML-115 50 mg/kg | 6 | 6 | 6 | 6 | 6 | 6 | 6 |
| Ciprofloxacin 50 mg/kg | 5.9 | 5.9 | 5.9 | 5.9 | 5.9 | 5.9 | 5.9 |
| Loracarbef 50 mg/kg | 6 | 2 | 2 | 2 | 2 | 2 | 2 |
| Vehicle | 6 | 0 | 0 | 0 | 0 | 0 | 0 |

The specific embodiments described herein are intended to illustrate the above invention and should not be construed as to narrow its scope. One skilled in the art will readily recognize that the embodiments suggest many other ways in which the invention could be practiced. It should be understood that numerous variations and modifications may be made while remaining within the scope: of the invention.

The contents of U.S. Provisional Patent Application Ser. No. 61/894,770, filed Oct. 23, 2013, U.S. patent application Ser. No. 13/865,801, filed Apr. 18, 2013, are incorporated by reference.

All publications, patents, internet links, and patent documents mentioned herein are incorporated by reference herein as though individually incorporated by reference. No limitations inconsistent with this disclosure are to be understood therefrom. The invention has been described with reference to specific embodiments and techniques. However, it should be understood that many variations and modifications may be made while remaining within the spirit, and scope of the invention.

The invention claimed is:

1. An Fe(III)-binding or Fe(III)-bound compound having the following formula:

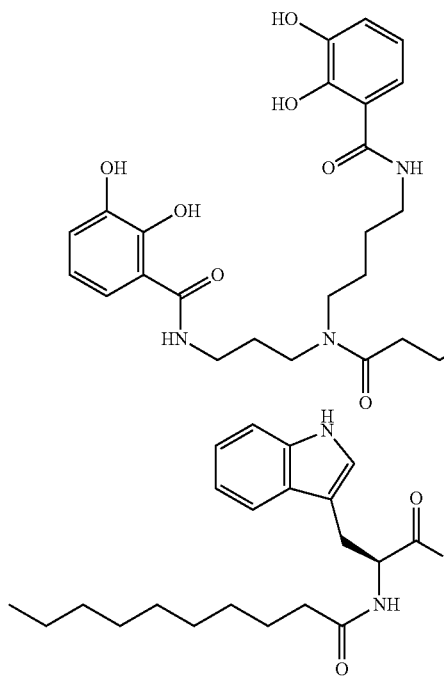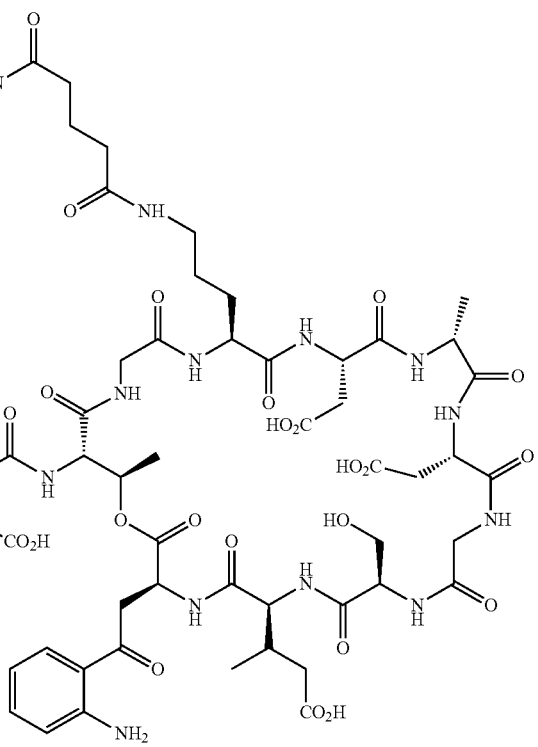

or pharmaceutically acceptable salt or solvate thereof.

2. A pharmaceutical composition, comprising the compound of claim 1, or mixture thereof and a pharmaceutically acceptable diluent or carrier.

3. The composition of claim 2, further comprising a hydrogel.

4. The composition of claim 2, further comprising a beta-lactamase inhibitor.

5. The composition of claim 2, further comprising a beta-lactamase inhibitor, wherein the beta-lactamase inhibitor is sulbactam, tazobactam, potassium clavulanate, or combination thereof.

6. A method for treating a bacterial infection in a subject, comprising administering the compound of claim 1 to the subject.

7. A method for treating a bacterial infection in a subject, comprising administering the composition of claim 2 to the subject.

8. The method of claim 7, wherein the bacterial infection is caused by an antibiotic-resistant bacterium.

9. The method of claim 7, wherein the bacterial infection is caused by a Gram-positive or Gram-negative bacterium.

10. A method for killing or inhibiting the growth of a bacterium, comprising contacting the bacterium with the compound of claim 1.

11. A method for killing or inhibiting the growth of a bacterium, comprising contacting the bacterium with the composition of claim 2.

* * * * *